United States Patent
Waterman et al.

(10) Patent No.: US 9,090,695 B2
(45) Date of Patent: Jul. 28, 2015

(54) ANTIBODIES FOR GUANYLYL CYCLASE RECEPTORS

(75) Inventors: Alisa Waterman, Ridgefield, CT (US); Daniel Rajotte, Laval (CA); Tobias Litzenburger, Planegg (DE); Alexandra Kraus, Planegg (DE)

(73) Assignee: MorphoSys AG, Martinsried/Planegg (DE)

( * ) Notice: Subject to any disclaimer, the term of this patent is extended or adjusted under 35 U.S.C. 154(b) by 526 days.

(21) Appl. No.: 13/132,493

(22) PCT Filed: Nov. 17, 2009

(86) PCT No.: PCT/US2009/064840
§ 371 (c)(1),
(2), (4) Date: Aug. 22, 2011

(87) PCT Pub. No.: WO2010/065293
PCT Pub. Date: Jun. 10, 2010

(65) Prior Publication Data
US 2012/0114659 A1    May 10, 2012

Related U.S. Application Data

(60) Provisional application No. 61/119,440, filed on Dec. 3, 2008.

(51) Int. Cl.
*C07K 16/28* (2006.01)
(52) U.S. Cl.
CPC ......... *C07K 16/2869* (2013.01); *C07K 2317/34* (2013.01); *C07K 2317/35* (2013.01); *C07K 2317/55* (2013.01); *C07K 2317/75* (2013.01); *C07K 2317/92* (2013.01); *C07K 2319/30* (2013.01)
(58) Field of Classification Search
CPC ........... C07K 16/2869; C07K 2317/55; C07K 2317/75
See application file for complete search history.

(56) References Cited

U.S. PATENT DOCUMENTS

| | | | |
|---|---|---|---|
| 2003/0099647 | A1 | 5/2003 | Deshpande et al. |
| 2004/0253242 | A1 | 12/2004 | Bowdish et al. |
| 2005/0169925 | A1 | 8/2005 | Bardroff et al. |
| 2007/0141634 | A1 | 6/2007 | Vuolteenaho et al. |
| 2008/0076670 | A1 | 3/2008 | Sivan et al. |
| 2008/0181903 | A1 | 7/2008 | Bhaskar et al. |
| 2008/0214437 | A1 | 9/2008 | Mohapatra et al. |

FOREIGN PATENT DOCUMENTS

| | | |
|---|---|---|
| WO | 20071008547 | 1/2007 |
| WO | 20101065293 | 6/2010 |

OTHER PUBLICATIONS

Deshmane et al., "Cytoplasmic domains mediate the ligand-induced affinity shift of guanylyl cyclase C," Biochemistry, 36(42):12921-12929 (1997).
Huang et al., "Localization and characterization of an orphan receptor, guanylyl cyclase-G, in mouse testis and sperm," Endocrinology, 147(10):4792-4800 (2006).
International Search Report and Written Opinion for PCT/US2009/064840 mailed Apr. 8, 2010.
List et al., "Different mechanisms are involved in the antibody mediated inhibition of ligand binding to the urokinase receptor: a study based on biosensor technology," J. Immunol. Methods, 222(1-2):125-133 (1999).
Lowe et al., "Human natriuretic peptide receptor—a guanylyl cyclase. Hormone cross-linking and antibody reactivity distinguish receptor glycoforms," J. Biol. Chem., 267(30):21691-21697 (1992).
Mumey et al., "A new method for mapping discontinuous antibody epitopes to reveal structural features of proteins," J. Comput. Biol., 10(3-4):555-567 (2003).
Extended European Search Report dated Jun. 19, 2013.
Horng et al: "Atrial natriuretic peptide modulators: Dissociation of receptor binding and particulate granulate cyclase activity" 1991.
Iwata et al: "Amiloride enhances atrial natriuretic factor stimulation of cGMP accumulation in rat glomeruli", 1989.
Parat et al: "Role of Extracellular Doman Dimerization in Agonist-Induced Activation of Natriuretic Peptide Receptor A", 2008.
Mison et al: "Structural studies of the natriuretic peptide receptor: A novel hormone-induced rotation mechanism for transmembrane signal transduction" 2005.
Yee, et al.: "Structure of the dimerized hormone-binding domain of a guanylylcyclase-coupled cyclase-coupled receptor", 2000.
Correa et al: "The role of natriuretic peptides in heart failure", 2008.

*Primary Examiner* — Ruixiang Li
(74) *Attorney, Agent, or Firm* — Paul F. Wiegel

(57) ABSTRACT

Monoclonal antibodies that act as potentiators, stimulators and agonists of guanylyl cyclase receptors are disclosed.

3 Claims, 18 Drawing Sheets

ANTIBODIES FOR GUANYLYL CYCLASE RECEPTORS

The present application is filed pursuant to 35 U.S.C. 371 as a U.S. National Phase application of International Patent Application No. PCT/US2009/064840, which was filed Nov. 17, 2009, claiming the benefit of priority to U.S. Provisional Patent Application No. 61/119,440, which was filed on Dec. 3, 2008. The entire text of the aforementioned applications is incorporated herein by reference in its entirety.

BACKGROUND OF THE INVENTION

Intracellular signaling via 3',5'-cyclic guanosine monophosphate (cGMP) plays an important role in many fundamental physiological processes including regulation of vascular tone, renal and cardiac function, immune responsiveness, thrombocyte activation, retinal phototransduction and bone growth. Because the level of endogenous cGMP modulates the aforementioned biological processes, molecules that regulate cGMP synthesis serve as natural targets for new drug discovery and therapeutic development. Guanylyl cyclases are such molecules.

More specifically, cGMP is produced by the catalysis of guanosine triphosphate (GTP) by one of two families of guanylyl cyclase enzymes: the particulate guanylyl cyclases (pGCs) and the soluble guanylate cyclases (sGCs). The pGCs generally exist as homodimers comprising an extended intracellular domain which includes the catalytic domain, membrane-spanning regions, and extracellular ligand-binding domain. In contrast, the sGCs are intracellular heterodimeric molecules containing a prosthetic heme group which can be activated by nitric oxide. Upon formation of the NO-heme complex, sGCs undergo conformational changes resulting in large increases in catalytic activity. The cGMP thus produced can regulate a number of effector molecules including protein kinases, phosphodiesterases and ion channels.

Of particular relevance to a host of therapeutic indications is the family of particulate guanylyl cyclases activated by natriuretic peptides. Natriuretic peptides are cyclic peptide hormones 28-32 amino acids long which are synthesized as longer preproproteins and processed to yield the mature peptides. Examples of natriuretic peptides include: A-type or atrial natriuretic peptide (ANP), which is released from the heart, urodilatin, the differentially processed form of ANP produced by the kidney, B-type natriuretic peptide (BNP), which is synthesized in the ventricular myocardium and C-type natriuretic peptide (CNP), which is produced by a number of cell types including endothelial cells and chondrocytes (Potter, et al *Endocrine Reviews*, 27:47, 2006).

One membrane-bound GC bound by ANP, urodilatin and BNP is the natriuretic peptide receptor A (also known as NPRA). Activation of NPRA by these hormones leads to a variety of physiological responses including vasorelaxation, natriuresis, diuresis, lipolysis, inhibition of cardiac hypertrophy and ventricular fibrosis, inhibition of the renin-angiotensin aldosterone system, and inhibition of sympathetic nerve activity. CNP, on the other hand, serves as a potent agonist for natriuretic peptide receptor B (NPRB). CNP-dependent activation of NPRB can also lead to vasodilation as well as stimulation of long bone growth. All of the natriuretic peptides have very short plasma half lives ranging from approximately 2-20 minutes. One reason for their rapid turnover is that they are degraded by proteases such as neutral endopeptidase (NEP), meprin A and dipeptidyl peptidase IV. Moreover, ANP, urodilatin, BNP and CNP also bind to the non-guanytyl cyclase clearance receptor, natriuretic peptide receptor C(NPRC). Binding to NPRC results in internalization of the peptides subsequent lysosomal degradation. See, e.g., Cohen et al., *J. Biol. Chem.*, 271:9863 1996.

NPRA has been shown to play an important role in the regulation of cardiorenal function. Activation of this receptor by ANP and BNP leads to a reduction in cardiac filling pressures, decrease in afterload, diuresis and natiuresis and inhibition of sympathetic and neurohormonal systems such as the renin-angiotensin-aldosterone pathway. Extended NPRA activation has cardiac antihypertropic and anti-fibrotic effects. ANP and BNP are produced by the heart in response to stress and stretch and are elevated in patients with heart failure. NPRA contains an intracellular GC domain and exerts its effects through the production of cGMP. However, as with many single transmembrane hormone receptors identification of small molecule agonists using conventional approaches have not been successful.

Recombinant forms of NPRA ligands have been approved for treatment of acute decompensated heart failure. However, these recombinant ligands have very short half-lives (typically 20 minutes or less) and thus must be administered by extended IV infusion. The recombinant form of BNP (Nesiritide) was approved in the U.S. in 2001 for the treatment of acute decompensated heart failure. Recombinant human ANP (Carperitide) was approved in Japan in 1995 for the same indication and recombinant urodilatin (Utaritide, renal form of ANP) is currently in clinical trials. Review of Nesiritide data submitted to the FDA during the approval process has further revealed significant safety concerns more particularly, increased mortality and reduced renal function, with the administration of recombinant BNP. While many of these safety concerns have subsequently been thought to be speculative, there remains a question as to the potential of the recombinant natriuretic peptides to induce adverse events. As such, the use of the currently approved compositions has been limited to an acute indication and there remains a need for additional therapies targeting the NPRA pathway for managing heart failure in a more chronic setting. A therapeutic intervention leading to the activation of the NPRA pathway that would allow for the treatment of both acute decompensated heart failure with a single administration and chronic heart failure with weekly or monthly injections would greatly benefit patients suffering from these serious conditions. To date such a therapy remains to be found.

Although efforts to modify natriuretic peptides and/or antagonize GC receptors have yielded some therapeutic compositions for use in acute decompensated heart failure, these efforts have failed to produce a robust therapeutic application for chronic heart failure. Thus, there is a current and continuing need to develop molecules that regulate pGCs, which are safe, have superior stability in vivo and effectively modulate the activation of the natriuretic peptide system.

BRIEF SUMMARY OF THE INVENTION

The object of the present invention addresses the above-identified need through the use of novel antibodies which act as potentiators or stimulators of guanylyl cyclase receptors. Specifically, the invention relates to isolated antibody or antigen-binding portion thereof that selectively binds to extracellular domain of a mammalian guanylyl cyclase(rGC) receptor in the presence of a ligand or an activating protein specific to the mammalian rGC such that the binding of the antibody or antigen binding portion thereof increases the apparent affinity of the ligand or activating protein for the mammalian rGC. In specific embodiments it is shown that the increased affinity of the ligand is seen as a slower off-rate of the ligand from the mammalian rGC which leads to an apparent increase in affinity. In general terms, the methods described herein result in an increase in molecular potency of the ligand making the ligand more effective in its biological response at lower concentrations. A highly potent drug evokes a larger response at low concentrations. As potency is a measure of drug's activity expressed in terms of the amount required to produce an effect of given intensity, "increased potency" of ligand using the methods of the invention generally means that less ligand or activating protein is required to produce a response in the presence of antibody or antigen-binding portion described herein as compared to the amount of ligand or activating protein that would be required to produce that level of response in the absence of said antibody or antigen-binding portion thereof that selectively binds to an extracellular domain of a mammalian guanylyl cyclase (rGC) receptor.

The mammalian rGC is preferably a human rGC, such as for example, NPRA, NPRB, NPRE or NPRF. In specific embodiments, the human rGC is NPRA.

The ligand in certain defined embodiments is an atrial natriuretic peptide (ANP), a brain natriuretic peptide (BNP), a C-type natriuretic peptide (CNP), *Dendroaspis* natriuretic peptide urodilatin (tiro), *Pseudocerastes persicus* natriuretic peptide, snake venom natriuretic-like peptide A (TNP-a), snake venom natriuretic-like peptide B (TNP-b), or snake venom natriuretic-like peptide C (INP-c) or active peptides derived from them or encompassing them.

In specific embodiments, the human rGC is NPRA and the ligand is ANP, BNP, Uro, or a mixture thereof. In other embodiments, the human rGC is NPRA and the ligand is ANP or BNP. In still other embodiments, the human rGC is NPRB and the ligand is CNP. In yet another embodiments, the human rGC is GC-C, GC-D, GC-E, GC-F or GC-G (Kuhn, *Circ Res* 93:700, 2003).

In specific aspects the increase in apparent affinity of the ligand or the activating protein to the mammalian rGC is at least 2-fold higher than it would be if the antibody or antigen-binding portion thereof was not present. In other embodiments, the $EC_{50}$ of ligand induced intracellular cGMP production is at least 2-fold lower than it would be if the antibody or antigen-binding portion thereof was not present.

In certain embodiments, the isolated antibody or antigen-binding portion thereof is such that binding of the antibody or antigen-binding portion thereof enhances or prolongs the catalytic activity associated with the mammalian rGC. The catalytic activity is seen to be enhanced or prolonged due to there being an enhanced response of the receptor to ligand such that more cGMP is produced at lower ligand concentrations. In specific embodiments, the catalytic activity is an increase in intracellular cGMP production where the rGC is NPRA or NPRB.

In specific embodiments, the antibody or antigen-binding portion thereof is a monoclonal antibody. In more specific embodiments, the antibody is an IgG antibody and more particularly an IgG4 or an IgG1 antibody.

In other embodiments, the antibody or antigen-binding portion thereof is selected from the group consisting of: a human antibody, a humanized antibody, a murine antibody, a chimeric antibody, a peptibody, a single chain antibody, a single domain antibody, a Fab fragment, a $F(ab')_2$ fragment, a Fv fragment, $scF_v$ fragment and a fusion protein.

Another aspect of the invention relates to an isolated antibody or antigen-binding, portion thereof that selectively binds to an epitope located in an extracellular domain of a mammalian receptor guanylyl cyclase (rGC) wherein the epitope forms when the rGC is bound to a ligand or activating protein specific to the mammalian rGC and wherein the antibody is not reactive with the ligand or activating protein binding site of the rGC. In specific embodiments, the antibody potentiates the activity of the ligand or activating protein through the receptor.

In certain embodiments, the antibody or antigen-binding portion thereof selectively binds an epitope located in the extracellular domain of NPRA, wherein the epitope comprises residues 7-28 (NLTVAVVLPLANTSYPWSWARV, SEQ ID NO:30), 121-129 (VKDEYALTT, SEQ ID NO:31), 313-320 (TMEDGLVN, SEQ ID NO:32), 327-333 (HDGLLLY, SEQ ID NO:33) and 347-351 (VTDGE, SEQ ID NO:34) located in the three dimensional structure of NPRA when NPRA is bound to ANP and/or BNP.

In still other embodiments, the antibody or antigen-binding portion thereof selectively binds an epitope located in the extracellular domain of NPRA, wherein the epitope comprises one or more of the sequences located in the three dimensional structure of NPRA when NPRA is bound to ANP and/or BNP. Such peptides include the pink portion shown in FIG. 22, which are produced by peptide sequences

```
                                        (SEQ ID NO: 35)
28-87 (VGPAVELALAQVKARPDLLPGWTVRTVLGSSENALGVCSDTA

APLAAVDLKWEHNPAVFL), (SEQ ID NO: 36)
96-113 (APVGRFTAHWRVPLLTAG), (SEQ ID NO: 37)
293-301 (PEYLEFLKQ), (SEQ ID NO: 38)
310-312 (FNF), 334-335 (IQ), 352-362 (NITQRMWNRSF).
```

Certain aspects of the invention relate to an isolated antibody or antigen-binding portion that selectively binds an epitope located in the extracellular domain of NPRA when the NP-A is bound to a ligand, the epitope being defined by a discontinuous region formed by the peptides shown above for NPRA.

Also contemplated is a monoclonal antibody having the same epitope specificity as monoclonal antibodies described herein wherein the monoclonal antibody is produced by host cells engineered to express nucleic acids that encode said antibody molecules.

Also contemplated is a specific isolated antibody or antigen-binding portion thereof that selectively binds to an epitope located in an extracellular domain of a mammalian receptor guanylyl cyclase (rGC) in the presence of a ligand or activating protein specific to the mammalian rGC, is not reactive with the ligand or activating protein binding site of the rGC and competes for binding to said epitope with a monoclonal antibody selected from the group consisting of an antibody comprising a VH and VL chain, each VH and VL chain comprising hypervariable regions CDR1, CDR2 and CDR3 separated by framework amino acid sequences, the hypervariable regions having amino acid sequences in each VH and VL wherein $VH^{CDR1}$ of said antibody has a sequence of SEQ ID NO:3;

$VH^{CDR2}$ of said antibody has a sequence selected from the group consisting of SEQ ID NO:4, 13 and 10, $VH^{CDR3}$ of said antibody has a sequence of SEQ ID NO:13, $VH^{CDR1}$ of said antibody has a sequence of SEQ ID NO:14, VL$^{CDR2}$ of said antibody has a sequence of SEQ. ID NO:15; and VL$^{CDR3}$ of said antibody has a sequence selected from the group consisting of SEQ ID NO: 16, 17 and 18 or an antibody shown in Tables 1 and 2.

Another aspect of the invention relates to an isolated antibody or antigen-binding portion thereof that binds to an epitope that is essentially the same epitope bound by an antibody comprising a VH and VL chain, each VH and VL chain comprising hypervariable regions CDR1, CDR2 and CDR3 separated by framework amino acid sequences, the hypervariable regions having amino acid sequences in each VH and VL wherein VH$^{CDR1}$ of said antibody has a sequence of SEQ ID NO:3;
VH$^{CDR2}$ of said antibody has a sequence selected from the group consisting of SEQ ID NO:4 and 10,
VH$^{CDR3}$ of said antibody has a sequence of SEQ ID NO:13,
VL$^{CDR1}$ of said antibody has a sequence of SEQ ID NO:14,
VL$^{CDR2}$ of said antibody has a sequence of SEQ ID NO:15; and
VL$^{CDR3}$ of said antibody has a sequence selected from the group consisting of SEQ ID NO:16, 17 and 18.

Other specific isolated antibody or antigen-binding portion thereof contemplated are those that bind to an epitope in an extracellular domain of a mammalian receptor guanylyl cyclase (rGC) in the presence of a ligand or activating protein specific to the mammalian rGC, wherein said epitope is bound by an antibody comprising a heavy chain variable region (V$_H$) and a light chain variable region (V$_L$), each V$_H$ and V$_L$ comprising hypervariable regions CDR1, CDR2 and CDR3 separated by framework amino acid sequences, the hypervariable regions having amino acid sequences in each V H and VL chain of each VH and VL chains of:

VH$^{CDR1}$ having a sequence of SEQ ID NO:3;
VH$^{CDR12}$ having a sequence selected from the group consisting of SEQ ID NO:4 and 10,
VH$^{CDR3}$ having a sequence of SEQ ID NO:13,
VL$^{CDR1}$ having a sequence of SEQ ID NO:14,
VL$^{CDR2}$ having a sequence of SEQ ID NO:15; and
VL$^{CDR3}$ having a sequence selected from the group consisting of SEQ ID NO:16, 17 and 18.

Other preferred antibodies are those specific for NPRA, comprising: a) a heavy chain variable region having the following amino acid sequences for complementarity determining regions, respectively: GDSVSSNSAAWS (SEQ ID NO:39); RTYYR-SHWYFEYAVSVKS (SEQ ID NO:40) and MDVPSFRYFDV (SEQ ID NO:41) and; b) a light chain variable region having the following amino acid sequences for complementarity determining regions, respectively: RASQSVRS- - - -NYLA (SEQ ID NO:42), GASNRAT (SEQ ID NO:43) and QQISNP-V (SEQ ID NO:44), wherein said antibody binds NPRA in the presence of an NPRA ligand and increases the affinity of said ligand for said NPRA as compared to the affinity of said ligand for said NPRA in the absence of said antibody.

Also contemplated are cell lines that produce an antibody or antigen-binding portion of an antibody described herein. Specific cell lines include those that produce an antibody wherein said antibody has a heavy and light chain CDRs 1, 2 and 3, wherein VH$^{CDR1}$ of said antibody has a sequence of SEQ ID NO:3;
VH$^{CDR2}$ of said antibody has a sequence selected from the group consisting of SEQ ID NO:4 and 10,
VH$^{CDR3}$ of said antibody has a sequence of SEQ ID NO:13,
VL$^{CDR1}$ of said antibody has a sequence of SEQ ID NO:14,
VL$^{CDR2}$ of said antibody has a sequence of SEQ ID NO:15; and
VL$^{CDR3}$ of said antibody has a sequence selected from the group consisting of SEQ ID NO:16, 17 and 18, Also contemplated is an isolated nucleic acid molecule comprising a sequence encoding an antibody or antigen-binding portion thereof which binds to natriuretic peptide receptor A (NPR-A), wherein said antibody or antigen-binding portion thereof comprises a heavy chain hypervariable region CDR2 having a sequence selected from the group consisting of SEQ ID NO:4 and 10.

Other embodiments describe an isolated nucleic acid molecule comprising a sequence encoding an antibody or antigen-binding portion thereof which binds to natriuretic peptide receptor A (NPRA), wherein said antibody or antigen-binding portion thereof comprises a light chain hypervariable region CDR3 having a sequence selected from the group consisting of SEQ ID NO:16, 17 and 18.

Yet another embodiment relates to an isolated nucleic acid molecule comprising a sequence encoding an antibody or antigen-binding portion thereof which binds to natriuretic peptide receptor A (NPRA), wherein said antibody or antigen-binding portion thereof comprises a heavy chain hypervariable region CDR2 having a sequence selected from the group consisting of SEQ ID NO:4 and 10 and a light chain hypervariable region CDR3 having a sequence selected from the group consisting of SEQ ID NO:16, 17 and 18.

Another aspect of the invention describes a nucleic acid molecule comprising a sequence encoding an antibody or antigen-binding portion thereof which binds to natriuretic peptide receptor A (NPRA), wherein said antibody or antigen-binding portion thereof comprises a heavy chain variable domain (V$_H$), wherein the V$_H$ comprises hypervariable regions VH$^{CDR1}$ having a sequence of SEQ ID NO:3; VH$^{CDR2}$ having a sequence selected from the group consisting of SEQ ID NO:4 and 10, and VH$^{CDR3}$ of said antibody has a sequence of SEQ ID NO: 13, wherein the hypervariable regions are separated by framework amino acid sequences. Also contemplated are isolated nucleic acid molecules comprising a sequence encoding an antibody or antigen-binding portion thereof which binds to natriuretic peptide receptor A (NPRA), wherein said antibody or antigen-binding portion thereof comprises a light chain variable domain (V$_L$), wherein the V$_L$ comprises hypervariable regions VL$^{CDR1}$ having a sequence of SEQ ID NO: 14; VL$^{CDR2}$ having a sequence of SEQ ID NO:15; and VL$^{CDR3}$ having a sequence selected from the group consisting of SEQ ID NO:16, 17 and 18, wherein the hypervariable regions are separated by framework amino acid sequences. In specific embodiments, the hypervariable regions are provided in a human framework region.

The present invention also relates to isolated nucleic acid molecule comprising a sequence encoding an antibody or antigen-binding portion thereof which binds to natriuretic peptide receptor A (NPRA), wherein said antibody or antigen-binding portion thereof is selected from the group consisting of: Ab1, Ab2, Ab3, Ab4 and Ab5, wherein Ab1-Ab5 comprises a VH and VL chain, each VH and VL chain comprising hypervariable regions CDR1, CDR2 and CDR3 separated by framework amino acid sequences, the hypervariable regions having amino acid sequences in each VH and VL chain of Ab1-Ab5 selected according to the following table:

Ab1: VH<sup>CDR1</sup>       VH<sup>CDR2</sup>       VH<sup>CDR3</sup>
     (SEQ ID NO: 3) (SEQ ID NO: 4) (SEQ ID NO: 13)

VL<sup>CDR1</sup>        VL<sup>CDR2</sup>        VL<sup>CDR3</sup>
     (SEQ ID NO: 14)(SEQ ID NO: 15)(SEQ ID NO: 16)

Ab2: VH<sup>CDR1</sup>       VH<sup>CDR2</sup>       VH<sup>CDR3</sup>
     (SEQ ID NO: 3) (SEQ ID NO: 4) (SEQ ID NO: 13)

VL<sup>CDR1</sup>        VL<sup>CDR2</sup>        VL<sup>CDR3</sup>
     (SEQ ID NO: 14)(SEQ ID NO: 15)(SEQ ID NO: 17)

Ab3: VH<sup>CDR1</sup>       VH<sup>CDR2</sup>       VH<sup>CDR3</sup>
     (SEQ ID NO: 3) (SEQ ID NO: 4) (SEQ ID NO: 13)

VL<sup>CDR1</sup>        VL<sup>CDR2</sup>        VL<sup>CDR3</sup>
     (SEQ ID NO: 14)(SEQ ID NO: 15)(SEQ ID NO: 18)

Ab4: VH<sup>CDR1</sup>       VH<sup>CDR2</sup>       VH<sup>CDR3</sup>
     (SEQ ID NO: 3) (SEQ ID NO: 10)(SEQ ID NO: 13)

VL<sup>CDR1</sup>        VL<sup>CDR2</sup>        VL<sup>CDR3</sup>
     (SEQ ID NO: 14)(SEQ ID NO: 15)(SEQ ID NO: 17)

Ab5: VH<sup>CDR1</sup>       VH<sup>CDR2</sup>       VH<sup>CDR3</sup>
     (SEQ ID NO: 3) (SEQ ID NO: 10)(SEQ ID NO: 13)

VL<sup>CDR1</sup>        VL<sup>CDR2</sup>        VL<sup>CDR3</sup>
     (SEQ ID NO: 14)(SEQ ID NO: 15)(SEQ ID NO: 18).

Also contemplated are vectors comprising and capable of expressing the nucleic acid molecule encoding an antibody or antigen-binding portion described herein and host cells transformed with such vectors. Such host cells may be bacterial host cells or mammalian host cells. Also contemplated is a method of producing an isolated antibody or antigen-binding portion thereof comprising the steps of culturing such a host cell. In specific embodiments, the nucleic acid molecule encoding the heavy and light chain hypervariable regions separated by framework amino acid sequences is coexpressed in the host cell under suitable conditions and recovering the antibody or antigen-binding portion thereof.

Also contemplated is a pharmaceutical composition comprising the purified antibody or antigen-binding portion thereof according to any one of claims 1-36 and a pharmaceutically acceptable carrier or excipient thereof.

The pharmaceutical composition of claim 50, wherein the antibody is monoclonal anti-natriuretic peptide receptor A antibody comprises a VH and VL chain, each VH and VL chain comprising hypervariable regions CDR1, CDR2 and CDR3 separated by framework amino acid sequences, the hypervariable regions having amino acid sequences in each VH and VL chain of Ab1-Ab5 selected according to the following table:

Ab1: VH<sup>CDR1</sup>       VH<sup>CDR2</sup>       VH<sup>CDR3</sup>
     (SEQ ID NO: 3) (SEQ ID NO: 4) (SEQ ID NO: 13)

VL<sup>CDR1</sup>        VL<sup>CDR2</sup>        VL<sup>CDR3</sup>
     (SEQ ID NO: 14)(SEQ ID NO: 15)(SEQ ID NO: 16)

Ab2: VH<sup>CDR1</sup>       VH<sup>CDR2</sup>       VH<sup>CDR3</sup>
     (SEQ ID NO: 3) (SEQ ID NO: 4) (SEQ ID NO: 13)

VL<sup>CDR1</sup>        VL<sup>CDR2</sup>        VL<sup>CDR3</sup>
     (SEQ ID NO: 14)(SEQ ID NO: 15)(SEQ ID NO: 17)

Ab3: VH<sup>CDR1</sup>       VH<sup>CDR2</sup>       VH<sup>CDR3</sup>
     (SEQ ID NO: 3) (SEQ ID NO: 4) (SEQ ID NO: 13)

VL<sup>CDR1</sup>        VL<sup>CDR2</sup>        VL<sup>CDR3</sup>
     (SEQ ID NO: 14)(SEQ ID NO: 15)(SEQ ID NO: 18)

Ab4: VH<sup>CDR1</sup>       VH<sup>CDR2</sup>       VH<sup>CDR3</sup>
     (SEQ ID NO: 3) (SEQ ID NO: 10)(SEQ ID NO: 13)

VL<sup>CDR1</sup>        VL<sup>CDR2</sup>        VL<sup>CDR3</sup>
     (SEQ ID NO: 14)(SEQ ID NO: 15)(SEQ ID NO: 17)

Ab5: VH<sup>CDR1</sup>       VH<sup>CDR2</sup>       VH<sup>CDR3</sup>
     (SEQ ID NO: 3) (SEQ ID NO: 10)(SEQ ID NO: 13)

VL<sup>CDR1</sup>        VL<sup>CDR2</sup>        VL<sup>CDR3</sup>
     (SEQ ID NO: 14)(SEQ ID NO: 15)(SEQ ID NO: 18).

Also contemplated is a method for increasing the apparent affinity of a ligand or an activating protein to an extracellular domain of a mammalian receptor guanylyl cyclase (rGC), comprising contacting the mammalian rGC with the purified antibody or antigen-binding portion thereof according to any one of claims 1-36 in the presence of the ligand or activating protein. The potentiation may be performed in vivo or in vitro.

Also contemplated herein are methods of treating a disorder or condition associated with a decreased level of catalytic activity of a mammalian rGC in a subject comprising administering to the subject in need thereof an effective amount of a purified antibody or antigen-binding portion described herein.

Other treatment methods include methods of treating a disorder or condition associated with a decreased level of catalytic activity of a mammalian rGC in a subject comprising administering to the subject in need thereof an effective amount of the pharmaceutical composition described herein.

The disorders to be treated include but are not limited to a disorder selected from the group consisting of heart failure, hypertension, resistant hypertension, pulmonary hypertension, atherosclerosis, diabetes, diabetic nephropathy, stroke, atrial fibrillation, ventricular arrythmias, deep vein thrombosis, myocarditis, valvular heart disease, pulmonary embolism, pericardial disease, coronary vasopasm, metabolic syndrome X, renal insufficiency (CKD, ESRD), obesity, asthma and allergic rhinitis.

The heart disease may be selected from the group consisting of non-ischemic chronic heart failure, post myocardial infarction heart failure (ischemic CHF), acute myocardial infarction, reperfusion injury, left ventricular dysfunction, cardiac fibrosis, diastolic heart failure, hypertrophic cardiomyopathy, acute decompensated heart failure and ischemic heart disease.

In specific embodiments, the invention involves treating acute decompensated heart failure in a subject comprising administering to the subject in need thereof an effective amount of the pharmaceutical composition according to the invention.

Other methods involve treating hypertension resistant hypertension or pulmonary hypertension in a subject comprising administering to the subject in need thereof an effective amount of a purified antibody or antigen-binding portion or a pharmaceutical composition comprising such an antibody or antigen binding portion thereof.

Other methods involve treating atherosclerosis in a subject comprising administering to the subject in need thereof an effective amount of a purified antibody or antigen-binding portion or a pharmaceutical composition comprising such an antibody or antigen binding portion thereof.

Other methods involve treating a disease in a subject, the disease being selected from the group consisting of Type 1 diabetes, Type 2 diabetes, diabetic nephropathy, stroke, atrial fibrillation/ventricular arrhythmias, deep vein thrombosis, myocarditis, valvular heart disease, pulmonary embolism, pericardial diseases, coronary vasospasm, metabolic syndrome X, renal insufficiency, allergic rhinitis, asthma, inflammatory disease, septic shock, obesity and cancer, comprising to the subject in need thereof an effective amount of a purified antibody or antigen-binding portion thereof described herein or a pharmaceutical composition comprising such an antibody or antigen binding portion thereof.

Also contemplated are methods of treating heart failure in a patient comprising administering a therapeutically effective amount of a purified antibody or antigen-binding portion thereof according to present invention and a second therapeutic agent for the treatment of heart failure. For example, the second agent may be selected from the group consisting of ARB/ACEi, ADP inhibitors, aldosterone antagonists, natieuretic peptides, anti-arrhythmic agents, HMG-CoA inhibitors, beta blockers, cardiac glycosides, calcium channel blockers, diuretics, fibrates, GPIIb/IIIa inhibitors, heparins, nicotinic acid derivatives, nitrates and nitrites, oral anticoagulants, thrombolytics, TZDs, cholesterol absorption inhibitors, acetyl salicylic acid, diapyridamole, phosphodiesterase inhibitors, CETP inhibitors/apoA1 mimetics, thrombin inhibitors, Factor Xa inhibitors, renin inhibitors, chymase inhibitors, RhoK inhibitors, LpPLA2 inhibitors, Endothelin receptor antagonists, HDAC inhibitors, nuclear receptor agonists, nuclear receptor antagonists, vasopeptidase inhibitors, fatty acid oxidation inhibitors, ACAT inhibitors, microsomal triglyceride transfer protein inhibitors, adenosine receptor modulators, AGE/RAGE interaction modulators, gene therapy, cell therapy.

In specific embodiments, the second agent is ANP, BNE or urodilatin. More specifically, the second agent is selected from the group consisting of Nesiritide, Carperitide, Ularitide, and combinations thereof.

Other methods of the invention comprise prolonging or increasing the therapeutic efficacy of an NPRA ligand in a patient comprising administering the NPRA ligand in combination with an antibody described herein or antigen binding portion of such an antibody. In specific aspects, the patient is suffering from heart failure. More specifically, the patient is suffering from acute decompensated heart failure. In other aspects, the patient is suffering from chronic heart failure, The NPRA ligand may be selected from the group consisting of is selected from the group consisting of Nesiritide, Carperitide, Ularitide, and combinations thereof. In specific aspects, co-administering the antibody with the NPRA ligand prolongs the effect of the NPRA ligand by at least two-fold the time of the NPRA ligand activity seen in the absence of the antibody. In specific embodiments, the antibody is administered concurrently with, prior to, or after administration of the NPRA ligand.

BRIEF DESCRIPTION OF THE DRAWINGS

FIG. 2A and FIG. 2B: Binding of 5064 in Fab and Fab-dHLX formats +/−ANP or BNP to HEK NPR A is determined by FACS. An irrelevant Fab or Fab-dHLX are utilized as a negative controls. FIG. 2C: Binding of 5064 in IgG format is compared to 5064 Fab binding by FACS.

Figure 1A:
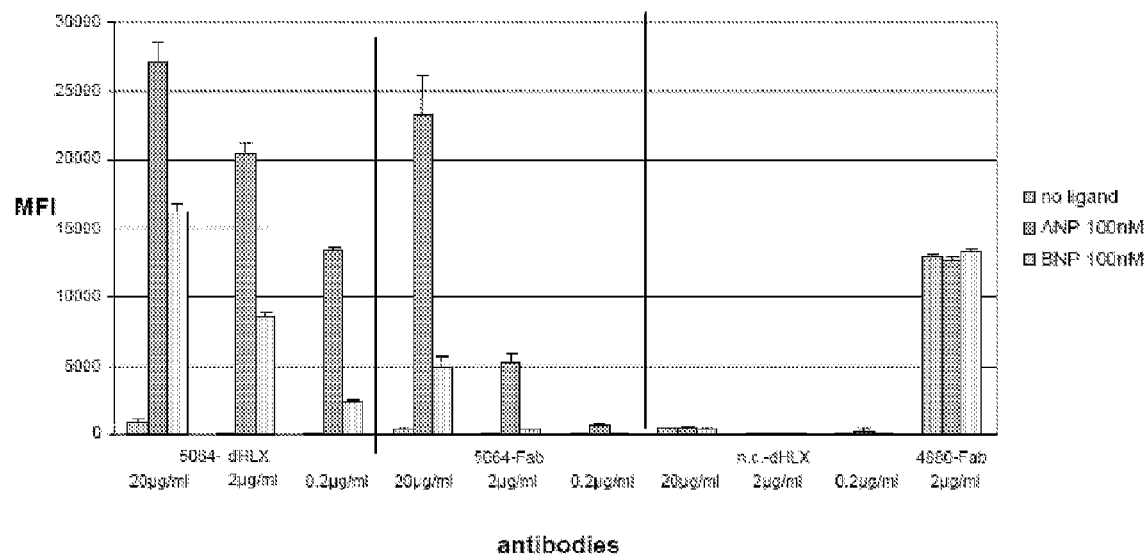
FIG. 1A and FIG. 1B: Binding of 5064 to HEK NPRA cells (FIG. 1A) and non-transfected HEK cells (FIG. 1B) in presence or absence of ANP or BNP. 5064 Fab, 5064 Fab-dHLX, a negative control Fab-dHLX (n.c.dHLX) and 4880 Fab are tested at 20, 2 and 0.2 µg/ml for binding to HEK NPRA cells and untransfected cells by FACS. 4880 Fab serves as a positive control as it is a Fab that binds to NPRA in the absence or presence of ANP or BNP. MFI—mean fluorescent intensity

```
                                            (SEQ ID NO: 35)
28-87   (VGPAVELALAQVKARPDLLPGWTVRTVLGSSENALGVCSDTA
APLAAVDLKWEHNPAVFL), (SEQ ID NO: 36)
96-113  (APVGRFTAHWRVPLLTAG), (SEQ ID NO: 37)
293-301 (PEYLEFLKQ), (SEQ ID NO: 38)
310-312 (FNF), 334-335 (IQ), 352-362 (NITQRMWNRSF).
```

DETAILED DESCRIPTION OF THE INVENTION

Heart failure remains a common and growing public health concern in the industrialized world. With currently available therapies approximately 50% of patients with heart failure die within 5 years of their diagnosis. The inadequacies of the currently approved therapies for heart failure have led to a continued search for robust and efficient therapeutic compositions that can be used in the treatment of acute decompensated heart failure as well as management of chronic heart failure. The present disclosure provides methods and compositions for potentially meeting this unmet need.

In general, the invention provides novel antibody compositions and methods of using therapeutically effective amounts of the same, either alone or in combination with other therapeutic agents, for the treatment or prevention of disease. The term "guanylyl cyclase or GC" refers to a family of enzymes (lyases) that catalyze the conversion of guanosine triphosphate (GTP) to 3',5'-cyclic guanosine monophosphate (cGMP) and pyrophosphate. GCs are subdivided into two forms: (1) soluble GCs and (2) particulate GCs. The soluble GCs can be activated by nitric oxide, whereas particulate GCs can be activated by peptide hormones, including natriuretic peptides. Particulate GCs are also referred to as receptor guanylyl cyclases (rGCs).

The term "natriuretic peptide receptors" as used herein refers to membrane-bound receptors that are bound by natriuretic peptides. Guanylyl cyclase A (GC-A isoform) or natriuretic peptide receptor A (NPRA) acts as the receptor for the natriuretic peptides ANP, urodilatin and BNP. The sequence of human NPRA is known to those of skill in the art. For example, a human NPRA nucleic acid sequence has been deposited at Genbank accession No. NM_000906. The nucleic acid sequence for NPRA is reproduced herein as SEQ ID NO:1. The amino acid sequence of NPRA is reproduced herein as SEQ ID NO:2. Guanylyl cyclase B (GC-B) or natriuretic peptide receptor B (NPRB) serves as the receptor for the natriuretic peptide CNP. Additionally, natriuretic peptide receptor C(NPRC) acts as a receptor for ANP, urodilatin, BNP and CNP. The clones of these various receptors may readily be purchased from OriGene Technologies, Inc. (Rockville, IMDI).

The term "natriuretic peptides or ligands" refers to a family of peptide hormones each containing a 17-amino acid long ring that is closed by a disulfide bond between two cysteine residues. A "ligand" is any molecule that binds to another molecule via non-covalent bonds. In biological processes, a ligand, binds specifically to another molecule, such as an enzyme or protein receptor, and is either transformed into something else or initiates a cellular process. ANP, urodilatin, BNP and CNP represent peptide hormones ligands that bind to pGCs. As mentioned above, ANP, urodilatin, and BNP bind to and activate NPRA. As used herein, the term "natriuretic peptide receptor A (NPRA) or guanylate cyclase A (GC-A)" may be used interchangeably with the following terms and/or acronyms: atrionatriuretic peptide receptor A, ANPa, ANP-A, ANPRA, Atrial natriuretic peptide A-type receptor, Atrial natriuretic peptide receptor A precursor, GUC2A, GUCY2A and NPR-A.

The biological activities associated with NPRA activation include, but are not limited to, vasodilation, diuresis, natriuresis, inhibition of cardiac remodeling, anti-fibrotic effects, anti-inflammatory effects, lipolysis and decreased sympathetic nervous system activity (see, e.g., Levin et al., *NEJM*, 339:321, 1998; Kuhn, *Circulation Res.*, 93:700, 2003; and Denus et al., *Chest*, 125:652, 2004). The compositions of the invention may be used in the treatment of a variety of diseases that involve these cGMP-mediated biological activities. Such diseases include but are not limited to disorders such as hypertension, resistant hypertension, pulmonary hypertension, chronic heart failure, acute decompensated heart failure, myocardial infraction, stable, unstable and variant (Prinzmetal) angina, atherosclerosis, cardiac edema, renal insufficiency, nephrotic edema, hepatic edema, stroke, asthma, bronchitis, chronic obstructive pulmonary disease (COPD), cystic fibrosis, dementia, immunodeficiency, premature labor, dysmenorrhea, benign prostatic hyperplasias (BPH), bladder outlet obstruction, incontinence, conditions of reduced blood vessel patency, e.g., postpercutaneous transluminal coronary angioplasty (post-PTCA), peripheral vascular disease, allergic rhinitis, cystic fibrosis, and glaucoma, and diseases characterized by disorders of gut motility, e.g., irritable bowel syndrome (IBS). In these methods, the antibody compositions and/or the additional therapeutic agents can be administered separately or as components of the same composition in one or more pharmaceutically acceptable carriers.

Particular aspects described herein relate to the treatment of various heart conditions, including chronic heart failure, hypertension, unstable angina, sudden cardiac death, and acute myocardial infarction, and particularly, acute decompensated heart failure. As described herein, natriuretic peptides such as ANP, and BNP are elevated in biological samples from patients with failing hearts but are at low levels in biological samples from control patients. BNP and ANP are ligands for the receptor NPRA. The antibodies of the present invention specifically recognize the activated ligand-receptor complex. Indeed, studies presented herein show little or no binding by the antibodies to either the receptor alone or to either of the ligands alone. Thus the antibodies of the invention are powerful and specific potentiators of the ligands only in the activated receptor complex. As these antibodies potentiate the effects of the activated complex (e.g., by prolonging the effect or by increasing the magnitude of the effect), these antibodies present a significant advance over the currently available recombinant peptide based therapies which are short lived.

Thus, it is contemplated that the antibody compositions described herein can be used in the therapeutic intervention of any disorder in which it is desired to increase, potentiate, or otherwise upregulate the production of cGMP mediated through the activated NPRA-ligand complex. While the antibodies alone have been shown to be effective in potentiating the effects of the NPRA receptor, it is contemplated that the antibody compositions also will be useful when used in combination with existing therapeutic compositions for the treatment of heart failure. In particular, it is contemplated that the antibody compositions will be used in combination with recombinant natriuretic peptides or derivatives thereof. Intravenous therapy with recombinant BNP (Nesiritide, Natrecor®.) significantly decreases pulmonary capillary wedge pressure and systemic vascular resistance and increases cardiac index. BNP is not pro-arrhythmic and has no effect on heart rate. Burger and Burger, *Curr. Opin. Investig. Drugs* 2:929 2001. It is contemplated that the antibody compositions will be administered in combination with Nesiritide. It is contemplated that such a combination therapy administration will result in decreased pulmonary capillary wedge pressure and systemic vascular resistance and increased cardiac index in an amount and manner that the therapeutic effect is longer than the effect typically observed in the use of Nesiritide alone. Thus, one embodiment described herein is a method of increasing the time and/or magnitude of one or more of decreases of pulmonary capillary wedge pressure and systemic vascular resistance and increased cardiac index observed on the treatment with recombinant natuiretic peptide.

Thus in some embodiments, the antibody compositions provided herein can be used to stimulate cGMP and/or vasodilate arteries in a mammal. In addition, the antibody compositions provided herein can be used to treat hypertension, pulmonary hypertension, resistant hypertension, acute decompensated heart failure and/or chronic heart failure. In other embodiments, the antibodies particularly are useful in increasing diuresis and/or natriuresis in a mammal. For example, an antibody composition described herein can be administered to a mammal to increase urinary flow and urinary excretion of sodium. In addition, the antibodies can be used to treat a fluid overload state (e.g., chronic heart failure, liver failure, and kidney failure) and/or to treat a sodium overloaded state (e.g., chronic heart failure and kidney failure).

Antibody Compositions

The present invention relates to antibody compositions that specifically bind the activated NPRA-ligand complex and potentiate the effects of the ligand of that receptor.

Typically, the term "agonist" refers to a ligand that binds to a receptor and activates it biological activity. "Agonistic activity" is defined as activation of a pGC leading to the production of cGMP. In some narrower and specific aspects, the term "NPRA agonist" is used to refer to an agent that causes an activation of an NPRA in the absence of its ligands ANP or BNP.

The term "potentiator" refers to a molecule(s) that affects the "on-rate" or "off-rate" of a ligand binding to its receptor and causes an increase in the effectiveness and/or duration of the agonistic activity. "Potentiating activity" is defined as an enhanced activation of a pGC in the presence of suboptimal concentrations of its ligands.

The following table provides exemplary CDR 1, CDR 2, CDR3 regions of the heavy and light chains of preferred antibodies of the present invention.

TABLE 1

| HEAVY CHAIN | | | |
|---|---|---|---|
| Antibody | VH CDR 1 | VH CDR 2 | VH CDR 3 |
| 5064 | GDSVSSRSASWS (SEQ ID NO: 3) | RIYYRSKWYN DYAVSVKS (SEQ ID NO: 4) | MDVPSFRYFDV (SEQ ID NO: 13) |
| 5503 | GDSVSSRSASWS (SEQ ID NO: 3) | RTYYRSHWYF EYAGSVKS (SEQ ID NO: 5) | MDVPSFRYFDV (SEQ ID NO: 13) |
| 5515 | GDSVSSRSASWS (SEQ ID NO: 3) | RTYYRSHWYW EYADSVKS (SEQ ID NO: 6) | MDVPSFRYFDV (SEQ ID NO: 13) |
| 5505 | GDSVSSRSASWS (SEQ ID NO: 3) | RTYYRSHWYY EYARSVKS (SEQ ID NO: 7) | MDVPSFRYFDV (SEQ ID NO: 13) |
| 5508 | GDSVSSRSASWS (SEQ ID NO: 3) | RTYYRSHWYF EYAHSVKS (SEQ ID NO: 8) | MDVPSFRYFDV (SEQ ID NO: 13) |

TABLE 1-continued

| Antibody | HEAVY CHAIN | | |
|---|---|---|---|
| | VH CDR 1 | VH CDR 2 | VH CDR 3 |
| 5509 | GDSVSSRSASWS (SEQ ID NO: 3) | RTYYRSHWYF DYAVSVKS (SEQ ID NO: 8) | MDVPSFRYFDV (SEQ ID NO: 13) |
| 5510 | GDSVSSRSASWS (SEQ ID NO: 3) | RTYYRSHWYY EYAASVKS (SEQ ID NO: 9) | MDVPSFRYFDV (SEQ ID NO: 13) |
| 5511 | GDSVSSRSASWS (SEQ ID NO: 3) | RTYYRSHWYY EYAQSVKS (SEQ ID NO: 10) | MDVPSFRYFDV (SEQ ID NO: 13) |
| 5512 | GDSVSSRSASWS (SEQ ID NO: 3) | RTYYRSHWYM EYAHSVKS (SEQ ID NO: 11) | MDVPSFRYFDV (SEQ ID NO: 13) |
| 5516 | GDSVSSRSASWS (SEQ ID NO: 3) | RTYYRSKWYY EYAHSVKS (SEQ ID NO: 12) | MDVPSFRYPDV (SEQ ID NO: 13) |
| 5502 | GDSVSSRSASWS (SEQ ID NO: 3) | RIYYRSKWYN DYAVSVKS (SEQ ID NO: 4) | MDVPSFRYFDV (SEQ ID NO: 13) |
| 5504 | GDSVSSRSASWS (SEQ ID NO: 3) | RIYYRSKWYN DYAVSVKS (SEQ ID NO: 4) | MDVPSFRYFDV (SEQ ID NO: 13) |
| 5507 | GDSVSSRSASWS (SEQ ID NO: 3) | RIYYRSKWYN DYAVSVKS (SEQ ID NO: 4) | MDVPSFRYFDV (SEQ ID NO: 13) |
| 5513 | GDSVSSRSASWS (SEQ ID NO: 3) | RIYYRSKWYN DYAVSVKS (SEQ ID NO: 4) | MDVPSFRYFDV (SEQ ID NO: 13) |
| 5514 | GDSVSSRSASWS (SEQ ID NO: 3) | RIYYRSKWYN DYAVSVKS (SEQ ID NO: 4) | MDVPSFRYFDV (SEQ ID NO: 13) |
| 5591 | GDSVSSRSASWS (SEQ ID NO: 3) | RTYYRSHWYY EYAQSVKS (SEQ ID NO: 10) | MDVPSFRYFDV (SEQ ID NO: 13) |
| 5592 | GDSVSSRSASWS (SEQ ID NO: 3) | RTYYRSHWYY EYAQSVKS (SEQ ID NO: 10) | MDVPSFRYFDV (SEQ ID NO: 13) |
| 5593 | GDSVSSRSASWS (SEQ ID NO: 3) | RTYYRSHWYY EYAQSVKS (SEQ ID NO: 10) | MDVPSFRYPDV (SEQ ID NO: 13) |
| 5594 | GDSVSSRSASWS (SEQ ID NO: 3) | RTYYRSHWYY EYAQSVKS (SEQ ID NO: 10) | MDVPSFRYFDV (SEQ ID NO: 13) |

TABLE 2

| Antibody | LIGHT CHAIN | | |
|---|---|---|---|
| | VL CDR 1 | VL CDR 2 | VL CDR 3 |
| 5064 | RASQSVRSNYLA (SEQ ID NO: 14) | GASNRAT (SEQ ID NO: 15) | QQISNPPVT (SEQ ID NO: 16) |
| 5503 | RASQSVRSNYLA (SEQ ID NO: 14) | GASNRAT (SEQ ID NO: 15) | QQISNPPVT (SEQ ID NO: 16) |
| 5515 | RASQSVRSNYLA (SEQ ID NO: 14) | GASNRAT (SEQ ID NO: 15) | QQISNPPVT (SEQ ID NO: 16) |
| 5505 | RASQSVPSNYLA (SEQ ID NO: 14) | GASNRAT (SEQ ID NO: 15) | QQISNPPVT (SEQ ID NO: 16) |
| 5508 | RASQSVRSNYLA (SEQ ID NO: 14) | GASNRAT (SEQ ID NO: 15) | QQISNPPVT (SEQ ID NO: 16) |
| 5509 | RASQSVRSNYLA (SEQ ID NO: 14) | GASNRAT (SEQ ID NO: 15) | QQISNPPVT (SEQ ID NO: 16) |
| 5510 | RASQSVRSNYLA (SEQ ID NO: 14) | GASNRAT (SEQ ID NO: 15) | QQISNPPVT (SEQ ID NO: 16) |
| 5511 | RASQSVRSNYLA (SEQ ID NO: 14) | GASNRAT (SEQ ID NO: 15) | QQISNPPVT (SEQ ID NO: 16) |
| 5512 | RASQSVRSNYLA (SEQ ID NO: 14) | GASNRAT (SEQ ID NO: 15) | QQISNPPVT (SEQ ID NO: 16) |
| 5516 | RASQSVRSNYLA (SEQ ID NO: 14) | GASNRAT (SEQ ID NO: 15) | QQISNPPVT (SEQ ID NO: 16) |
| 5502 | RASQSVRSNYLA (SEQ ID NO: 14) | GASNRAT (SEQ ID NO: 15) | QQISNSPPT (SEQ ID NO: 17) |
| 5504 | RASQSVRSNYLA (SEQ ID NO: 14) | GASNRAT (SEQ ID NO: 15) | QQISRAPAT (SEQ ID NO: 18) |
| 5507 | RASQSVRSNYLA (SEQ ID NO: 14) | GASNRAT (SEQ ID NO: 15) | QQISTNPPT (SEQ ID NO: 19) |
| 5513 | RASQSVRSNYLA (SEQ ID NO: 14) | GASNRAT (SEQ ID NO: 15) | QQISSSPAT (SEQ ID NO: 20) |
| 5514 | RASQSVPSNYLA (SEQ ID NO: 14) | GASNRAT (SEQ ID NO: 15) | QQISISPPT (SEQ ID NO: 21) |

TABLE 2-continued

LIGHT CHAIN

| | VL CDR 1 | VL CDR 2 | VL CDR 3 |
|---|---|---|---|
| 5591 | RASQSVRSNYLA (SEQ ID NO: 14) | GASNRAT (SEQ ID NO: 16) | QQISNSPPT (SEQ ID NO: 17) |
| 5592 | RASQSVRSNYLA (SEQ ID NO: 14) | GASNRAT (SEQ ID NO: 16) | QQISRAPAT (SEQ ID NO: 18) |
| 5593 | RASQSVRSNYLA (SEQ ID NO: 14) | GASNRAT (SEQ ID NO: 16) | QQISTNPPT (SEQ ID NO: 19) |
| 5594 | RASQSVRSNYLA (SEQ ID NO: 14) | GASNRAT (SEQ ID NO: 16) | QQISSSPAT (SEQ ID NO: 20) |
| 5595 | RASQSVRSNYLA (SEC ID NO: 14) | GASNRAT SEQ ID NO: 16) | QQISISPAT (SEQ ID NO: 21) |

The framework of regions of the heavy chains for the exemplary antibodies were as follows:

```
FR 1 for the VH region:
                                       (SEQ ID NO: 22)
QVQLQQSGPGLVKPSQTLSLTCAIS FR 2 for the VH region:
                                       (SEQ ID NO: 23)
WIRQSPGRGLEWLG FR 3 for the VH region:
                                       (SEQ ID NO: 24)
RITINPDTSKNQFSLQLNSVTPEDTAVYYCAR FR 4 for the VH region:
                                       (SEQ ID NO: 25)
WGQGTLVTVSS
```

The framework of regions of the light chains for the exemplary antibodies were as follows:

```
FR 1 for the VL region:
                                       (SEQ ID NO: 26)
DIVLTQSPATLSLSPGERATLSC FR 2 for the VL region:
                                       (SEQ ID NO: 27)
WYQQKPGQAPRLLIY FR 3 for the VL region:
                                       (SEQ ID NO: 28)
GVPARFSGSGSGTDFTLTISSLEPEDFAVYYC FR 4 for the VL region:
                                       (SEQ ID NO: 29)
FGQGTKVEIKRT
```

Given that the present invention has identified unique antibodies that have therapeutic applicability, each of the heavy and light chains depicted in the present application can now be prepared using recombinant methods and processed in a recombinant cell line to a mature form. Accordingly, by using recombinant production in mammalian cells, the mature form of the antibody is processed proteolytically and also includes other post translational modifications such as glycosylation.

Nucleic acids encoding light chain variable regions can be constructed and co-expressed with nucleic acids encoding a heavy chain and vice versa, and optionally may be linked to constant regions. Any heavy chain and light chains may be combined as long as suitable NPRA binding affinity is maintained. The desired genes encoding the light and heavy chains are introduced into mammalian cells and the resultant recombinant immunoglobulin products are expressed, purified and characterized using standard recombinant methods.

An "antibody" generally refers to a protein that recognizes and binds to a specific antigen and an "immunoglobulin" generally refers to a glycoprotein that functions as an antibody. In native form, an immunoglobulin molecule consists of four chains, two identical heavy chains (about 50-70 kDa each) and two identical light chains (about 25 kDa each), which are held together by disulfide bonds. Specifically, each heavy chain is linked to a light chain by one disulfide bond, whereas the number of disulfide bonds between heavy chains varies depending on the immunoglobulin isotype (IgG, IgA, IgM, IgD and IgE). Additionally, each heavy chain and each light chain has regularly spaced intrachain disulfide bonds or bridges. In both heavy and light chains, there are constant domains and variable domains. For example, each heavy chain ($\gamma$, $\delta$, $\alpha$, $\mu$ or $\epsilon$) has at one end a variable domain ($V_H$) followed by a number of constant domains ($C_{H1}$, $C_{H2}$, $C_{H3}$, $C_{H4}$), whereas each light chain (either $\lambda$ or $\kappa$) has a variable domain ($V_L$) at one end and constant domain ($C_L$) at its other end. $C_L$ is aligned with $C_{H1}$ and $C_L$ is aligned with $V_L$.

It is contemplated that the antibodies of the invention may be an IgG molecule of any isotype (i.e., the framework may be an IgG1, IgG2, IgG3 or an IgG4 type IgG). Depending on the amino acid sequence of the constant domain of their heavy chains, human immunoglobulins can be assigned to different classes. There are five major classes, IgA, IgD, IgE, IgG and IgM, and several of these may be further divided into subclasses or isotypes, e.g. IgG1, IgG2, IgG3, IgG4, IgA1 and IgA2. The heavy-chain constant domains that correspond to the different classes of immunoglobulins are called alpha, delta, epsilon, gamma and mu respectively. The subunit structures and three-dimensional configurations of different classes of immunoglobulins are well known. Different isotypes have different effector functions; for example, IgG1 and IgG3 isotypes have ADCC activity.

In certain embodiments, the therapeutic antibodies of the invention are IgG1 molecules. It is now established that IgG4 does not activate complement, as such, the chance of an immunogenic response and inflammation due to antigen-antibody-complement complexes is greatly reduced with the use of IgG4 molecules as compared to other isotypes. This makes IgG4 a very attractive candidate for therapy as it is expected to be a safe therapeutic modality: IgG4 should simply bind to antigen and should not trigger any additional response in human body. For example, in nature, an IgG4-based response is generated in response to, for example, antigens such as dust mite, grass pollen or bee sting. These antigens are typically eliminated without significant immune response and inflammation. Thus, in some embodiments it is desirable that the antibodies of the invention are IgG4 antibodies. Regardless of the isotype used, when the compositions are formulated, it is desirable to include in the formulation agents that will allow the confonation and refolding of the isotypes to be as homogeneous as possible by for example including agents such as chaotropic and redox reagents to limit the refolding of double bonds (see WO 2006/047340).

As used herein, the term "antibody" refers to an intact immunoglobulin and "an antigen-binding portion thereof" refers to a protein molecule that competes with the intact antibody for specific binding. An antibody may be monoclonal, chimeric, humanized, human, CDR-grafted or murine antibody. In specific embodiments, the antibodies described herein are fully human antibodies that are identified through phage display from human combinatorial libraries such as for example HuCal® (Morphosys, Munich, Germany). Antigen-binding portions may be produced by recombinant DNA techniques or by enzymatic or chemical cleavage of intact antibodies. Antigen-binding portions include, but are not limited to, Fab, Fab', F(ab')$_2$, Fv, a single domain antibody (dAb), and complementarity determining region (CDR) fragments, single-chain antibodies (scFv), diabodies and polypeptides or fusion proteins that contain at least a portion of an immunoglobulin that is sufficient to confer specific antigen binding to the polypeptide such that the polypeptide still binds to an NPRA receptor and preferably exhibits a biological activity of the antibodies described herein.

An "epitope or determinant" generally relates to a specific chemical domain on an antigen that stimulates the production of, and is recognized by, an antibody. An individual epitope on a molecule such as protein elicits the synthesis of a different antibody (also known as an antigenic determinant). The epitope is defined by the three dimensional structure of the molecule to which the antibody binds. In the present disclosure, antibodies have been identified which specifically bind to one monomer of the NPhRA dimer that is formed upon binding of ANP to the receptor. FIG. 29 summarizes mass spectrometry data of the three dimensional structure and epitopes of the NPRA to which the antibodies of the invention bind.

Hydrogen/Deuterium Mass Spectrometry (HXMS) analysis showed that the strongest binding is to a region of the extracellular domain of NPRA that contains the peptides encompassing residues 7-28 (NLTVAVVLPLANTSYP-WSWARV) (SEQ ID NO:30), 121-129 (VKDEYALTT) (SEQ ID NO:31), 313-320 (TMEDGLVN) (SEQ ID NO:32), 327-333 (HDGLLLY) (SEQ ID NO:33) and 347-351 (VTDGE) (SEQ ID NO:34). These peptides form one discontinuous region in the three dimensional structure of NPRA when NPRA has bound thereto ANP.

The term "antigen" refers broadly to any substance that elicits an immune response.

The complementarity determining regions of the NPRA may be inserted into a unique combination of the human heavy and light chains of structurally differing IgG1 and IgG2 and IgG4. The binding of these antibodies to NPRA and their efficacy as NPRA agonists or potentiators of NPRA ligands can be readily assessed using assays such as those described in the examples below.

The term "specific binding agent" includes antibodies as defined above and recombinant peptides or other compounds that contain sequences derived from CDRs having the desired antigen-binding properties. Specifically included in the term are peptides containing amino acid sequences that are at least 80%, 90% or 100% identical to one or more CDRs of NPRA antibodies described herein, preferably including a variable heavy chain CDR2 having a sequence RIYYRSKW-YNDYAVSVKS (SEQ ID NO:4) or RTYYRSHW-YYEYAQSVKS (SEQ ID NO: 10) and/or a light chain CDR3 having a sequence of QQISNPPVT (SEQ ID NO: 16) or QQISNSPPT (SEQ ID NO:17) or QQISRAPAT (SEQ ID NO:18).

Other antibody-related molecules also are contemplated. In particular, the antibodies of the invention can form the basis for "peptibodies." These antibody related molecules which comprise an antibody Fc domain as the "vehicle" attached to at least one antigen-binding peptide. Antibody CDR's from the NPRA antibodies, particularly those that include the heavy chain CDR2 and/or the light chain CDR3 described above, may be suitable for incorporation into a peptibody. For a more detailed description of peptibody production, see WO 00/24782, published May 4, 2000. Peptibodies can be made by linking peptides in tandem (i.e., sequentially) either directly to each other or separated by linkers. Those peptides that contain cysteine residues may be cross-linked with another cysteine-containing peptide, either or both of which may be linked to a vehicle, Any peptide having more than one Cys residue may form an intrapeptide disulfide bond, as well. Antibodies technologies often will use derivatization of such peptides using for example, capping of the carboxyl terminus with an amino group, capping cysteines residues or substituting amino acid residues by moieties other than amino acid residues (see, e.g., Bhatnagar et al., J. Med. Chem. 39: 3814, 1996, and Cuthbertson et al., J. Med. Chem. 40: 2876, 1997). In addition, optimization of the peptides for NPRA binding properties akin to the affinity maturation of the antibodies also can be performed.

The antigen binding portion of the antibodies of the invention also can be modified with various molecules that can be inserted within the peptide portion itself or between the peptide and vehicle portions of the specific binding agents, while retaining the desired activity of specific binding agent. Exemplary such insertions include insertion of an Fc domain, addition of a polyethylene glycol or other related molecules such as dextran, a fatty acid, a lipid, a cholesterol group, a small carbohydrate, a peptide, a cytotoxic agent, a chemotherapeutic agent, a detectable moiety as described herein (including fluorescent agents, radiolabels such as radioisotopes), an oligosaccharide, oligonucleotide, a polynucleotide, interference (or other) RNA, enzymes, hormones, or the like. Other molecules suitable for incorporation in this fashion will be appreciated by those skilled in the art, and are encompassed within the scope of the invention. This includes insertion of for example, a desired molecule in between two consecutive amino acids, optionally joined by a suitable linker.

An "isolated" antibody is one that has been identified and separated from a component of the cell that expressed it, Contaminant components of the cell are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody, and most preferably more than 99% by weight, (2) to a degree sufficient to obtain at least 15 residues of N-terminal or internal amino acid sequence, or (3) to homogeneity by SDS-PAGE under reducing or nonreducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

The term "hypervariable" region refers to the amino acid residues of an antibody which are responsible for antigen-binding. The hypervariable region comprises amino acid residues from a complementarity determining region or CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)]. Even a single CDR may recognize and bind antigen, although with a lower affinity than the entire antigen binding site containing all of the CDRs. It is understood that the CDR of an antibody may include additional or fewer sequences outside the specified limits above so long as the antibody retains its ability to bind the target molecule.

"Framework" or "FR" residues are those variable region residues other than the hypervariable region residues.

"Antibody fragments" comprise a portion of an intact full length antibody, preferably the antigen binding or variable region of the intact antibody. Examples of antibody fragments include Fab, Fab', F(ab')2, and Fv fragments; diabodies; linear antibodies (Zapata et al., *Protein Eng.*, 8:1057, 1995); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment which contains the constant region. The Fab fragment contains all of the variable domain, as well as the constant domain of the light chain and the first constant domain ($C_{H1}$) of the heavy chain. The Fc fragment displays carbohydrates and is responsible for many antibody effector functions (such as binding complement and cell receptors), that distinguish one class of antibody from another.

Antibodies that are treated with pepsin yield a F(ab)s fragment that has two "Single-chain Fv" or "sFv" antibody fragments comprising the VH and VL domains of antibody, both of which are present in a single polypeptide chain. Fab fragments differ from Fab' fragments by the inclusion of a few additional residues at the carboxy terminus of the heavy chain CH1 domain including one or more cysteines from the antibody hinge region. Preferably, the Fv polypeptide further comprises a polypeptide linker between the VH and VL domains that enables the Fv to form the desired structure for antigen binding. For a review of sFv see Pluckthun in The Pharmacology of Monoclonal Antibodies, vol. 113, Rosenburg and Moore eds., Springer-Verlag, New York, pp. 269-315 (1994).

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH VL dimer. Collectively, the six CDRs confer antigen-binding specificity to the antibody. However, a single variable domain (or half of an Fv comprising only three CDRs specific for an antigen) has the ability to recognize and bind antigen, although at a lower affinity than the entire binding site.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites, Diabodies are described more fully in, for example, EP 404,097; WO 93/11161 and 30; Hollinger et al., *Proc. Nat. Acad. Sci. USA*, 90:6444, 1993.

Various techniques have been developed for the production of antibody fragments. Traditionally, these fragments were derived via proteolytic digestion of intact antibodies, but can also be produced directly by recombinant host cells. See, for example, Better et al., *Science* 240:1041, 1988; Skerra et al. *Science* 240: 1038, 1988; Carter et al., *Bio/Technology* 10:163, 1992.

Method of Identifying the Antibodies

Antibodies of the present invention may now be produced using recombinant DNA methodology using one of the antibody expression systems well known in the art (see, e.g., Harlow and Lane, Antibodies: A Laboratory Manual, Cold Spring Harbor Laboratory (1988)).

The amino acid sequence of the VH and VL regions of interest have been described herein. The suitable encoding nucleotide sequences can be designed according to a universal codon table using techniques known to those of skill in the art. The nucleic acids are then amplified and cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the antibody where, for example, the nucleic acid molecule is in a chromosomal location different from that of natural cells.

The sequences encoding immunoglobulins or immunoglobulin polypeptides specific for binding to NPRA were identified using phage display technology. Phage display is described in e.g., Dower et al, WO 91/17271, McCafferty et al., WO 92/01047, and Caton and Koprowski, *Proc. Nat. Acad. Sci. USA*, 87:6450, 1990, each of which is incorporated herein by reference. In preferred aspects, the antibodies of the present invention were identified using phage display techniques using a human combinatorial library (HuCal®; Morphosys, Munich, Germany). This library comprises more than ten billion different, fully human antibodies. HuCAL® allows rapid and automated production of high-affinity antibodies. The most important feature of the library is its capability of optimizing fully human antibodies to meet predefined specifications. Detailed experimental protocols for the identification of the antibodies described herein are provided in Examples 3 through 6 below. Briefly, however, the antibodies were identified after several pannings were performed with the HuCAL GOLD®, library in order to select agents from the library that had a binding affinity for NPRA similar to the activities found for the NPRA ligands ANP and BNP. Although antibodies specific for NPRA could be selected from the library, none of the antibodies induced activation of NPRA on their own. It may be possible that the binding site of the cyclic peptides ANP and BNP on NPRA is structurally not accessible by a Fab with a mass more than 10 times bigger than the peptides.

As an alternative, the next sets of selections were performed against the receptor-ligand complex. These selections succeeded in identification of a binder, which specifically recognizes this complex. This antibody, designated 5064, stabilizes the receptor-ligand complex and enhances the potency of ANP or BNP in NPRA dependent cGMP production. This antibody now may be used in a variety of therapeutic applications in which the effects of ANP and/or BNP or any other NPRA agonist are desired. In particular, the potentiating antibodies identified herein will be particularly useful in boosting the activities of natriuretic peptides. According to data presented herein the 5064 antibody is able to decrease the dissociation of ANP from cellular NPRA.

The antibody 5064 was then subjected to affinity maturation in H-CDR2 and L-CDR3, which resulted not only in significantly increased binding to the receptor-ligand complex on cells, but also to increased biological activity. Thus in the presence of sub-optimal concentrations of natriuretic peptides the matured antibodies increased the cGMP response stronger than the parental antibody. In conclusion, we can see a clear correlation of antibody affinity and biological activity. New combinations of matured L- and H-chains even resulted in a further improved activity of the antibodies. Of interest is the fact that the five most potent matured antibodies were all optimized in the L-CDR3, while H-CDR2 matured binders showed weaker activities. Maybe the L-CDR3 provides crucial binding sites to the receptor, so that optimization of L-CDR3 has a greater effect than optimization of H-1-CDR2. In the H-CDR2 sequences only a few residues of the parental sequence were changed, which indicates that the H-CDR2 may also be important in binding but does not allow major modification of its sequence.

The data presented herein show that affinity maturation starting with only one candidate can be successful. For the first time a potentiating antibody was isolated from the HuCAL GOLD® library, which, however, was not agonistic by itself, but strongly amplifies the activity of the natural peptide ligands.

Methods of Making the Antibodies

The sequence of the identified nucleic acid is then determined. Typically the sequence encoding an entire variable region of the immunoglobulin polypeptide is determined, however, it will sometimes be adequate to sequence only a portion of a variable region, for example, the CDR-encoding portion. Typically the portion sequenced will be at least 30 bases in length, more often bases coding for at least about one-third or at least about one-half of the length of the variable region will be sequenced.

Once isolated, the DNA encoding the various portions of the antibody may be operably linked to expression control sequences or placed into expression vectors, which are then transfected into host cells such as *E. coli* cells, simian COS cells, Chinese hamster ovary (CHO) cells, human embryonic kidney cells (HEK), or myeloma cells that do not otherwise produce immunoglobulin protein, to direct the synthesis of monoclonal antibodies in the recombinant host cells. Recombinant production of antibodies is well known in the art.

Expression control sequences refer to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

The invention also provides isolated nucleic acids encoding specific binding agents or antibodies of the invention, optionally operably linked to control sequences recognized by a host cell, vectors and host cells comprising the nucleic acids, and recombinant techniques for the production of the specific binding agents or antibodies, which may comprise culturing the host cell so that the nucleic acid is expressed and, optionally, recovering the specific binding agent or antibody from the host cell culture or culture medium.

Many vectors are known in the art. Vector components may include one or more of the following: a signal sequence (that may, for example, direct secretion of the specific binding agent or antibody), an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

Suitable host cells include prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis*, *Pseudomonas*, and *Streptomyces*. In addition to prokaryotes, eukaryotic microbes such as filamentous fungi or yeast are suitable cloning or expression hosts for specific binding agent-encoding vectors. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris*, *Schizosaccharomyces pombe*; *Kluyveromyces*, *Yarrowia*; *Candida*; *Trichoderma reesia*; *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated specific binding agent or antibody are derived from multicellular organisms. Examples of invertebrate cells include insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-1 variant of *Autographa californica* NPV and the Bm-5 strain of *Bombyx mori* NPV.

However, typical recombinant protein production employs mammalian cells, and propagation of mammalian cells in culture (tissue culture) has become routine procedure. Examples of useful mammalian host cell lines are Chinese hamster ovary cells, including CHOK1 cells (ATCC CCL61), DXB-11, DG-44, and Chinese hamster ovary cells/–DHFR (CHO, Urlaub et al., *Proc. Natl. Acad. Sci. USA* 77: 4216, 1980); monkey kidney CV1 line transformed by SV40 (COS- 7, ATCC CRL 1651); human embryonic kidney line (293 or 293 cells subcloned for growth in suspension culture, [Graham et al., *J. Gen Virol.* 36: 59, 1977]; baby hamster kidney cells (BHK, ATCC CCL 10); mouse sertoli cells (TM4, Mather, *Biol. Reprod.* 23: 243, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G-2,1-B 8065); mouse mammary tumor (MMT 060562, ATCC CCL51); TRI cells (Mather et al., *Annals N. Y Acad. Sci.* 383: 44, 1982); MRC 5 cells or FS4 cells.

Host cells are transformed or transfected with the nucleic acids or vectors that encode NPRA specific antibodies of the invention are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of specific binding agents or antibodies.

The host cells transformed with nucleic acids that encode for the desired antibodies of the invention can be cultured in a variety of commonly available culture media, such as for example, media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When the host cells are cultured, the antibody or portions thereof can be produced intracellularly, in the periplasmic space, or directly secreted into the medium. If the specific binding agent or antibody is produced intracellularly, as a first step, the particulate debris, either host cells or lysed fragments, is removed, for example, by centrifugation or ultrafiltration.

The antibody composition can then be purified using, for example, hydroxylapatite chromatography, cation or anion exchange chromatography, or preferably affinity chromatography, using the antigen of interest or protein A or protein G as an affinity ligand. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the specific binding agent or antibody comprises a CH3 domain, the Bakerbond ABX™resin (J. T. Baker, Phillipsburg, N.J.) is useful for purification. Other techniques for protein such as ethanol precipitation, Reverse Phase HPLC, chromatofocusing, SDS-PAGE, and ammonium sulfate precipitation are also possible depending on the specific binding agent or antibody to be recovered.

Antibody Derivatives and Variants

The antibodies of the invention could be derivatized. For example, it is possible to insert amino and/or carboxy terminal fusions of varying amino acid lengths as well as intra-sequence insertions of single or multiple amino acid residues. Examples of terminal insertions include a specific binding agent or antibody with an N-terminal methionyl residue or the specific binding agent or antibody (including antibody fragment) fused to an epitope tag or a salvage receptor epitope. Other insertional variants of the specific binding agent or antibody molecule include the fusion to a polypeptide which increases the serum half-life of the specific binding agent or antibody, e.g. at the N-terminus or C-terminus. Other exemplary mutations that can be prepared include mutations in IgG4 which prevent chain exchange. The mutations can be formed as described in e.g., Marijn et al. *Science* 317: 1554, 2007. That reference describes describe a posttranslational modification that leads to anti-inflammatory activity of antibodies of immunoglobulin G, isotype 4 (IgG4). IgG4 antibodies are dynamic molecules that exchange Fab arms by swapping a heavy chain and attached light chain (half-molecule) with a heavy-light chain pair from another molecule, which results in bispecific antibodies. Mutagenesis studies have shown that the third constant domain is critical for this activity. The impact of IgG4 Fab arm exchange was confirmed in vivo in a rhesus monkey model with experimental autoimmune myasthenia gravis. IgG4 Fab arm exchange is suggested to be an important biological mechanism that provides the basis for the anti-inflammatory activity attributed to IgG4 antibodies. Mutating the third constant domain of IgG4 in order to prevent chain exchange in the antibodies described herein is particularly useful.

Examples of epitope tags include the flu HA tag polypeptide and its antibody 12CA5 [Field et al. *Mol. Biol.* 8: 2159, 1988]; the c-myc tag and the 8F9, 3C7, 6E10, G4, B7 and 9E10 antibodies thereto [Evan et al., *Mol. Cell. Biol.* 5: 3610, 1985]; and the Herpes Simplex virus glycoprotein D (gD) tag and its antibody [Paborsky et al., *Protein Engineering* 3:547, 1990]. Other exemplary tags are a poly-histidine sequence, generally around six histidine residues, that permits isolation of a compound so labeled using nickel chelation. Other labels and tags, such as the FLAG®tag (Eastman Kodak, Rochester, N.Y.) are well known and routinely used in the art.

The term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Another type of variant is an amino acid substitution variant. These variants have at least one amino acid residue in the specific binding agent or antibody molecule removed and a different residue inserted in its place. Substitutional mutagenesis within any of the hypervariable or CDR regions or framework regions is contemplated. Conservative substitutions are particularly contemplated. Conservative substitutions involve replacing an amino acid with another member of its class. Non-conservative substitutions involve replacing a member of one of these classes with a member of another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the specific binding agent or antibody to improve its stability (particularly where the antibody is an antibody fragment such as an Fv fragment).

Variants of the antibodies described herein can be produced that will have a modified glycosylation pattern relative to the parent antibody, for example, deleting one or more carbohydrate moieties found in the antibody, and/or adding one or more glycosylation sites that are not present in the specific binding agent or antibody.

Glycosylation of polypeptides including antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to a specific binding agent or antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to a specific binding agent or antibody by inserting or substituting one or more serine or threonine residues to the sequence of the original specific binding agent or antibody.

Cysteine residue(s) may be removed or introduced in the Fc region, thereby eliminating or increasing interchain disulfide bond formation in this region. The homodimeric specific binding agent or antibody thus generated may have improved internalization capability and/or increased complement-mediated cell killing and antibody-dependent cellular cytotoxicity (ADCC). See Caron et al., *J. Exp Med.* 176: 1191, 1992 and Shopes, B. *J. Immunol.* 148: 2918, 1992. Homodimeric specific binding agents or antibodies may also be prepared using heterobifunctional cross-linkers as described in Wolff et al., *Cancer Research* 53:2560, 1993. Alternatively, a specific binding agent or antibody can be engineered which has dual Fc regions and may thereby have enhanced complement lysis and ADCC capabilities. See Stevenson et al., *Anti-Cancer Drug Design* 3: 219, 1989.

Sequences within the CDR can cause an antibody to bind to MHC Class II and trigger an unwanted helper T-cell response. A conservative substitution can allow the specific binding agent or antibody to retain binding activity yet reduce its ability to trigger an unwanted T-cell response.

Modifications of the antibodies to increase serum half-life also may be desirable, for example, by incorporation of or addition of a salvage receptor binding epitope (e.g., by mutation of the appropriate region or by incorporating the epitope into a peptide tag that is then fused to the specific binding agent or antibody at either end or in the middle, e.g., by DNA or peptide synthesis) (see, e.g., WO096/32478) or adding molecules such as PEG or other water soluble polymers, including polysaccharide polymers.

The salvage receptor binding epitope preferably constitutes a region wherein any one or more amino acid residues from one or two loops of a Fc domain are transferred to an analogous position of the specific binding agent or antibody or fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the specific binding agent or antibody. Alternatively, the epitope is taken from the CH2 domain of the Fc region and transferred to the CL region or VL region, or both, of the specific binding agent or antibody fragment. These techniques for modifying antibodies using Fc variants and their interaction with the salvage receptor are well known to those of skill in the art and have been described e.g., in WO 97/34631 and WO 96/32478.

Other sites of the constant region have been identified that are responsible for complement dependent cytotoxicity (CDC), such as the C1q binding site and/or the antibody-dependent cellular cytotoxicity (ADCC) [see, e.g., *Mol. Immunol.* 29:633, 1992; Shields et al., *J. Bio. Chem.*, 276: 6591, 2001, incorporated by reference herein in its entirety]. Mutation of residues within Fc receptor binding sites can result in altered (i.e. increased or decreased) effector function, such as altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different subclass (e.g. replacing an IgG1 residue with a corresponding IgG2 residue at that position).

Covalent modifications of the antibody are also contemplated. Such covalent modifications may be made by chemical synthesis or by enzymatic or chemical cleavage of the antibody, if applicable. Other types of covalent modifications can be introduced into the specific binding agent or antibody by reacting targeted amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH-6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R—N=C=N—

R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deaminated to the corresponding glutamyl and aspartyl residues, respectively. These residues are deaminated under neutral or basic conditions. The deaminated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the specific binding agent or antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Removal of any carbohydrate moieties present on the specific binding agent or antibody may be accomplished chemically or enzymatically. Chemical deglycosylation requires exposure of the specific binding agent or antibody to the compound trifluoromethanesulfonic acid, or an equivalent compound. This treatment results in the cleavage of most or all sugars except the linking sugar (N-acetylglucosamine or N-acetylgalactosamine), while leaving the specific binding agent or antibody intact. Chemical deglycosylation is described by Hakimuddin, et al., *Arch. Biochem. Biophys*, 259:52 1987 and by Edge et al. *Anal. Biochem.*, 118:131, 1981. Enzymatic cleavage of carbohydrate moieties on a specific binding agent or antibody can be achieved by the use of a variety of endo- and exo-glycosidases as described by Thotakura et al., *Meth. Enzymol.* 138: 350, 1987.

Another type of covalent modification of the antibody comprises linking it to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640, 835; 4,496,689; 4,301,144; 4,670,417; 4,791,192, 4,179,337, 4,766,106, 4,179,337, 4,495,285, 4,609,546 or EP 315 456.

Methods of Therapy

"Treatment" is an intervention performed with the intention of preventing the development, progession, or altering the pathology of a disorder. Accordingly, "treatment" refers to both therapeutic treatment and prophylactic or preventative measures. Those in need of treatment include subjects that already have symptoms of the disorder as well as those who have been diagnosed as likely to develop the disorder and hence in whom the disorder is to be prevented. The phrase "treatment" may include ameliorating, suppressing, eradicating, reducing the severity of, decreasing the frequency of incidence of, preventing, reducing the risk of, and/or delaying the onset of the condition.

"Mammal" for purposes of treatment refers to any animal classified as a mammal, including humans, domestic and farm animals, and zoo, sports, or pet animals, such as dogs, horses, cats, cows, etc. Preferably, the mammal is human.

As used herein, the phrase "therapeutically effective amount" is meant to refer to an amount of therapeutic or prophylactic NPRA antibody that prolongs the biological effects of ANP and/or BNP through the action of the NPRA receptor. In particular aspects, these methods are effective treatments for a variety of cardiovascular conditions. Such effectiveness may be realized in, for example, efficacy, potency, dosing requirements, and/or reduced side effects. The term "cardiovascular condition" is used broadly in this application, and includes, for example, hypertension (including resistant hypertension and pulmonary hypertension), heart failure (such as chronic heart failure (i.e., "CHF"), or heart failure following myocardial infarction), arrhythmia, diastolic dysfunction (such as left ventricular diastolic dysfunction, diastolic heart failure, or impaired diastolic filling), systolic dysfunction, ischemia (such as myocardial ischemia), cardiomyopathy (such as hypertrophic cardiomyopathy and dilated cardiomyopathy), sudden cardiac death, myocardial fibrosis, vascular fibrosis, impaired arterial compliance, myocardial necrotic lesions, vascular damage in the heart, vascular inflammation in the heart, myocardial infarction ("MI") (including both acute post-MI and chronic post-MI conditions), coronary angioplasty, left ventricular hypertrophy, decreased ejection fraction, coronary thrombosis, cardiac lesions, vascular wall hypertrophy in the heart, endothelial thickening, myocarditis, coronary artery disease (such as fibrinoid necrosis of coronary arteries), and atherosclerosis.

Administering the antibodies provides an effective treatment for a variety of conditions that are associated (either directly or indirectly) with hypertension, heart failure, and/or other cardiovascular conditions. Such secondary conditions include, for example, renal dysfunctions, cerebrovascular diseases, vascular diseases generally, retinopathy, neuropathy (such as peripheral neuropathy), edema, endothelial dysfunction, and insulinopathy (including complications arising from insulinopathy). Examples of renal dysfunctions include glomerulosclerosis, end-stage renal disease, acute renal failure, diabetic nephropathy, reduced renal blood flow, increased glomerular filtration fraction, proteinuria, decreased glomerular filtration rate, decreased creatine clearance, microalbuminuria, renal arteriopathy, ischemic lesions, vascular damage in the kidney, vascular inflammation in the kidney, and malignant nephrosclerosis (such as ischemic retraction, thrombonecrosis of capillary tufts, arteriolar fibrinoid necrosis, and thrombotic microangiopathic lesions affecting glomeruli and microvessels). Examples of cerebrovascular diseases include stroke. Examples of vascular diseases include thrombotic vascular disease (such as mural fibrinoid necrosis, extravasation and fragmentation of red blood cells, and luminal and/or mural thrombosis), proliferative arteriopathy (such as swollen myointimal cells surrounded by mucinous extracellular matrix and nodular thickening), atherosclerosis, decreased vascular compliance (such as pathological vascular stiffness and/or reduced ventricular compliance), and endothelial dysfunction. Examples of edema include peripheral tissue edema and lung congestion. Examples of insulinopathies include insulin resistance, Type I diabetes mellitus, Type II diabetes mellitus, glucose sensitivity, pre- and diabetic syndrome X.

Thus, in some embodiments, the pathological condition comprises a cardiovascular disease, renal dysfunction, edema, a cerebrovascular disease, or an insulinopathy. In other embodiments, the condition to be treated is a cardiovascular disease, stroke, or type II diabetes. In still other embodiments, the condition to be treated is hypertension, heart failure, left ventricular hypertrophy, or stroke. In still other embodiments, the condition to be treated is a cardiovascular disease. In some other aspects, the condition to be treated is hypertension. In still other embodiments, the condition to be treated is heart failure, arrhythmia, diastolic dysfunction, systolic dysfunction, ischemia, cardiomyopathy, sudden cardiac death, myocardial fibrosis, vascular fibrosis, impaired arterial compliance, myocardial necrotic lesions, vascular damage in the heart, myocardial infarction, left ventricular hypertrophy, decreased ejection fraction, vascular wall hypertrophy in the heart, or endothelial thickening. The heart failure may be acute heart failure, acute post-myocardial-infarction heart failure, chronic heart failure, chronic post-myocardial-infarction heart failure, hypertension-driven heart failure, sudden cardiac death, vascular inflammation in the heart. The condition to be treated may be coronary angioplasty, coronary thrombosis, cardiac lesions, myocarditis, coronary artery disease, such as fibrinoid necrosis of coronary arteries. In other aspects, the condition to be treated is renal dysfunction. In still other embodiments, the condition to be treated is a cerebrovascular disease.

In exemplary combination protocols the subject is dosed with a first composition comprising the antibody composition and a second composition comprising the addition therapeutic agent for the treatment of the disorder. The first and second compositions together form a therapeutically-effective treatment for the targeted condition(s). It should be recognized that the specific dose level and frequency of dosing for the antibody and other therapeutic agents will depend on a variety of factors including, for example, the particular combination of agents selected; the activity, efficacy, pharmacokinetic, and toxicology profiles of the particular therapeutic agents used (including such profiles when the agents are used in combination); the age, weight, general health, sex, and diet of the patient; the frequency of administration; the rate of excretion; the condition(s) being treated; the severity of the condition(s) being treated; whether a drug delivery system is used; the form, route, and frequency of administration; and whether other pharmaceutically-active compounds also are being administered. Thus, the dosage regimen actually employed may vary widely, and therefore may deviate from the preferred dosage regimens set forth in this patent.

The total daily dose of each drug generally may be administered to the patient in a single dose, or in proportionate multiple subdoses. Subdoses typically are administered from 2 to about 6 times per day, and more typically from 2 to about 4 times per day. Doses may be in an immediate-release form or sustained-release form effective to obtain desired results. It should be recognized that, although the dosing frequency for the therapeutic agents in this invention is typically daily or multiple times per day, this invention also contemplates dosing regimens wherein the preferred period between administration of one or more of the therapeutic agents is greater than 24 hours. In such embodiments, the dosing frequency may be, for example, every 36 hours, every 48 hours, every 72 hours, weekly, or monthly.

In the combination therapies contemplated, the administration may comprise administering the antibody and the second agent in a substantially simultaneous manner using either a single formulation (e.g., a single capsule) having a fixed ratio of the therapeutic agents, or separate formulations (e.g., multiple capsules) that each comprise at least one of the therapeutic agents. Such administration also may comprise administering the antibody and other therapeutic agent at different times in separate formulations. This may include, for example, administering the components of the combination in a sequential manner. Or it may include administering one component multiple times between the administrations of another component. Or it may include administering two components at the same time, while also separately administering another portion at least one of those components at a different time as well. Or it may include administering the two components sequentially for a two-step effect. Where the components of the combination are dosed separately, the time period between the dosing of each component may range from a few minutes to several hours or days, and will depend on, for example, the properties of each component (e.g., potency, solubility, bioavailability, half-life, and kinetic profile), as well as the condition of the patient.

Dosage and dosage-frequency optimization (to the extent desirable) may be determined in trials. It should be recognized that multiple doses per day typically may be used to increase the total daily dose, if desired.

Dosing of the first and second compositions can be determined and adjusted based on measurement of parameters that would be known to one skilled in the art. Non-limiting examples of such parameters generally include blood pressure, pulmonary capillary wedge pressure or appropriate surrogate markers (such as cGMP, natriuretic peptides, endothelins, and other surrogate markers). Blood pressure, pulmonary capillary wedge pressure and/or surrogate marker levels after administration of the combination therapy can be compared against the corresponding baseline levels before administering the therapy to determine efficacy of the present method and titrated as needed. Non-limiting examples of surrogate markers useful in the method are surrogate markers for renal and cardiovascular disease.

It should be recognized that it is often preferred to start dosing the therapeutic agents of the combination at an intermediate levels (particularly an intermediate levels falling within the above-described preferred dosage ranges), and then titrate up or down, depending on observed efficacy and side-effects. In many embodiments, treatment is continued as necessary over a period of several weeks to several months or years until the condition(s) has been controlled or eliminated. Patients undergoing treatment with the antibodies disclosed herein can be routinely monitored by a wide variety of methods known in the art for determining the effectiveness of a treatment for the particular condition being treated. This may include, for example, blood pressure, echocardiography; MRI; monitoring C-reactive protein, brain natriuretic peptides ("BNP"), fibrinogen levels, and pro-inflammatory molecule (e.g., TNF$\alpha$., MMP-2, MMP-3, JMM P-13, etc.) and cGN P levels in the bloodstream; and, for kidney-related diseases, it also may include, for example, monitoring the urea appearance rate ("UAR"). Kidney function cal also be measured using creatinine clearance and cystatin levels using methods known to those of skill in the art. Continuous analysis of such data permits modification of the treatment regimen during therapy so that optimal effective amounts of each type of therapeutic agent are administered at any time, and so that the duration of treatment can be determined as well. In this way, the treatment regimen/dosing schedule can be rationally modified over the course of therapy so that the lowest amount of each therapeutic agent that together exhibit satisfactory effectiveness is administered, and so that administration is continued only so long as is necessary to successfully treat the condition.

The antibody treatment and/or the combination therapies of this invention may be administered prophylactically, before a diagnosis of a cardiovascular condition (or associated condition), and to continue administration of the combination during the period of time the subject is susceptible to the condition. Individuals with no remarkable clinical presentation, but that are nonetheless susceptible to pathologic effects, therefore can be placed on a prophylactic dose of the combination. Such prophylactic doses may, but need not, be lower than the doses used to treat the specific pathogenic effect of interest.

In some embodiments of this invention, cardiac pathologies are identified, and an effective dosing and frequency determined, based on blood concentrations of natriuretic peptides. Elevated natriuretic peptide levels in the blood, particularly blood BNP levels, generally are observed in subjects under conditions of blood volume expansion and after vascular injury such as acute myocardial infarction and remain elevated for an extended period of time after the infarction. (Uusimaa et al., *Int. J. Carrdiol*, 69:5, 1999. A decrease in natriuretic peptide level relative to the baseline level measured before administration of a therapy (antibody alone or antibody in combination with another therapy) of this invention indicates a decrease in the pathologic effect mediated by the therapy, and, therefore, provides a correlation with inhibition of the pathologic effect. Blood levels of the desired natriuretic peptide level therefore can be compared against the corresponding baseline level before administration of the therapy to determine efficacy of the present method in treating the pathologic effect. Based on such natriuretic peptide level measurements, dosing of the combination can be adjusted to reduce the cardiovascular pathologic effect. Efficacy of the therapeutic agent and determination of the appropriate dosing can also be based on circulating and urinary cCGMP Levels. An increased plasma level of cGMP parallels a fall in pulmonary capillary wedge pressure. Increased urinary excretion of cGMP can be correlated with the natriuresis.

In some embodiments, a therapy of this invention is administered at a dosage and frequency effective to cause a statistically-significant decrease in tissue or circulating C-reactive protein (CRP) levels.

In some embodiments, a therapy of this invention is administered to a patient having an ejection fraction of less than about 45%, particularly less than about 40%, and even more particularly less than about 30%. In such embodiments, the therapy preferably is administered at a dosage and frequency effective to cause a statistically-significant increase (or preserve, or at least partially preserve) left ventricular ejection fraction. In other embodiments, the therapy is administered in an amount effective to achieve hemodynamic improvements such as improved cardiac output, pulmonary capillary wedge pressure. The therapy also may be useful in producing a decrease in infarct size post-MI.

In some embodiments, a therapy of this invention is administered at a dosage and frequency effective to cause a statistically-significant increase (or preserve, or at least partially preserve) stroke volume.

In some embodiments, a therapy of this invention is administered at a dosage and frequency effective to cause a statistically-significant decrease in left ventricular end systolic area, end diastolic area, end systolic volume, or end diastolic volume.

In some embodiments, a therapy of this invention is administered at a dosage and frequency effective to cause a statistically-significant decrease in left ventricular mass.

In some embodiments, a therapy of this invention is administered at a dosage and frequency effective to cause a statistically-significant decrease in interstitial collagen fraction in the heart (which can be monitored by, for example, measuring collagen markers or measuring the stiffness of the heart using, for example, an echocardiogram).

In some embodiments, a therapy of this invention is administered based on the presence of myocardial infarction or heart failure or left ventricular hypertrophy. Left ventricular hypertrophy can be identified by echo-cardiogram or magnetic resonance imaging and used to monitor the progress of the treatment and appropriateness of the dosing.

For the treatment of hypertension, the subject is typically first identified as normotensive, borderline hypertensive, or hypertensive based on blood pressure determinations. For humans, in particular, such a determination may be achieved using a seated cuff mercury sphygmomanonmeter. Individuals may be deemed normotensive when systolic blood pressure and diastolic blood pressure are less than about 125 mm Hg and less than about 80 mm Hg, respectively; borderline hypertensive when systolic blood pressure and diastolic blood pressure are in the range of from about 125 to about 140 mm Hg and from about 80 to about 90 mm Hg, respectively; and hypertensive when systolic blood pressure and diastolic blood pressure are greater than about 140 mm Hg and 90 mm Hg, respectively. As the severity of the hypertensive condition increases, the preferred dose of at least one component of the therapy typically increases. Based on post-administration blood pressure measurement, the doses of the components of the combination may be titrated. After an initial evaluation of the subject's response to the treatment, the doses may be increased or decreased accordingly to achieve the desired blood pressure lowering effect.

Dosing and frequency to treat pathologies of renal function can be determined and adjusted based on, for example, measurement of proteinuria, microalbuminuria, decreased glomerular filtration rate (GFR), or decreased creatinine clearance, Proteinuria is identified by the presence of greater than about 0.3 g of urinary protein in a 24 hour urine collection. Microalbuminuria is identified by an increase in assayable urinary albumin. Based upon such measurements, dosing of the dosing and frequency of a combination of this invention can be adjusted to ameliorate a renal pathologic effect.

Neuropathy, especially peripheral neuropathy, can be identified by, and dosing and frequency adjustments based on, neurologic exam of sensory deficit or sensory motor ability. Retinopathy can be identified by, and dosing and frequency adjustments based on, ophthalmologic exam.

Animal Models for Monitoring Therapy

Various animal models are available for testing the therapeutic compositions of the invention. For example, the antibody preparations either alone or in combination with other recognized treatments for heart failure may be tested in rat models for spontaneously hypertensive heart failure. Such a rat model has been described in the art. Heyen et al., "Structural, functional, and molecular characterization of the SHHF rat model of heart failure", *Am. J. Physiol.*, 283:H1775, 2002 (incorporated by reference into this patent). This model may be used as described below to evaluate the therapeutic potential of the antibodies and or combination therapies contemplated herein.

For example, lean, male SHHF rats (Genetic Models Inc., Indianapolis, Ind.) are used as the test models and age-matched Sprague-Dawley (SD) rats (Charles River Labs, Raleigh, N.C.) are used as controls. All animals are acclimated to their environment, e.g., housed in a room lighted for 12 hours per day at an ambient room temperature.

Another model that can be used is the volume expanded hypertensive rat model (also known as the aldosterone/salt rat model) which has been described in the art. See, e.g., Rocha, R., et al., *Am. J. Physiol. Heart Circ. Physiol.*, 283: H1802, 2002. See also, Blasi, E. R., et al., *Kidney International*, 63: 1791, 2003. See also, PCT Patent Publication No. WO 01/95893.

Following acclimation, unnephrectomized rats are given 1% NaCl drinking water and infused subcutaneously with aldosterone (0.5 g/kg/hr) via an Alza osmotic pump, Model 2002. These rats are assigned to one of the following treatment groups: (1) rats receiving no treatment; (2) rats receiving a second therapeutic agent of interest at a dosing of interest, (3) rats receiving an antibody of interest at a dosing of interest, and (4) rats receiving a co-administration of the aldosterone antagonist at a dosing of interest and the antibody at a dosing of interest. The treatments continued for 3 weeks. Over that period, blood pressure and heart rate are evaluated continuously by telemetry via an implanted transmitter connected to a pressure transducer cannulated to the abdominal aorta. The blood pressure and heart rate data is averaged over 24-hour periods.

The stroke prone spontaneously hypertensive rat (SHR—SP) model has been described in the art. See, e.g., Rocha, R., et al., *Trends in Endocrin. & Met.*, 12: 308, 2001.

The study is conducted over a defined period of time, e.g., 12 weeks, with measurements and samples taken at baseline, and at set intervals thereafter (e.g., after 4, 8, and 12 weeks). Following acclimation, baseline measurements are performed, and 1 week later, the rats are assigned to one of the following treatment groups after being randomized based on genotype: (1) rats receiving no treatment; (2) rats receiving the antibody at a dose of interest, (3) rats receiving a a second agent of interest at a dose of interest, and (4) rats receiving a co-administration of the antibody at a dose of interest and the second agent at a desired dose of interest.

The rats are monitored for transthoracic echocardiography. See Heyen, J. R. R., et al. The examinations are performed at baseline, and after 4, 9, and 13 weeks of treatment during the progression of heart failure. During these examinations, each animal is lightly anesthetized, the chest is shaved, and echocardiograms are obtained.

Intra-ventricular systolic blood pressure is measured following 12 weeks of treatment. During this analysis, each animal is anesthetized and the right common carotid artery is cannulated with a Millar catheter transducer (Millar, Houston, Tex.) passed under constant pressure into the left ventricle. Data is collected every 10 seconds for 3 minutes and analyzed using a HPA-210 heart performance analyzer (Micro-Med, Louisville, Ky.).

Alternatively, tail-cuff systolic blood pressure is analyzed non-invasively at baseline, and after 6 and 12 weeks of treatment using the Visitech BP-2000 Blood Pressure Analysis System (Visitech Systems, Apex, N.C.). Six measures are taken for each animal and averaged for a mean SBP reading.

Serum electrolytes are analyzed using a Hitachi 912 automated diagnostic clinical chemistry analyzer (Roche Diagnostics Corp., Indianapolis, Ind.) according to standard procedures.

At the end of the experiment, each animal is anesthetized and weighed. The abdominal cavity is opened to expose the abdominal aorta. An 18-gauge needle is then inserted into the abdominal aorta, and the animals are exsanguinated. The resulting blood is immediately transferred into serum collection tubes and the samples are then centrifuged for 15 min at 3,000 rev/min at 4° C. to form a serum that is, in turn, collected and frozen at −80° C. until further analysis.

Following exsanguination, the heart is isolated, removed, rinsed in cold PBS (Gibco, Gaithersburg, Md.), blotted dry, and weighed. Tibia also are removed (documented by X-ray analysis), and the length is determined using calipers, The observed heart weight is then normalized to tibial length (HW/TL). A 6-mm section is cut transversely through the middle of the heart and placed into 10% neutral-buffered formalin for 24 hr, followed by 70% alcohol until embedded into paraffin. The remaining apical portion of the heart is snap frozen in liquid nitrogen and stored at −80° C. for molecular analysis.

Urinary proteinuria is determined by using the Bio-Rad protein dye reagent (Hercules, Calif.). The assay is modified to a 96-well plate format according to the manufacturer's instructions.

During this experiment, the groups of rats are compared with respect to, for example, systolic blood pressure, ejection fraction, stroke volume, left ventricular end diastolic area, left ventricular end systolic area, left ventricular end diastolic volume, left ventricular end systolic volume, urinary protein, TNFα in the serum and heart tissue, left ventricular mass (absolute and normalized to tibial length), plasma osteopontin, and MMP levels and activity.

Another rat model that has been commonly described in the art and could be used for testing antibody preparations alone or in combination with standard treatments is a coronary artery ligation model (leg Raya, et. al., *Circ Res* 64:330, 1989). Adult male Sprague-Dawley rats undergo experimental myocardial infarction (MI) by standard techniques in which the animals are anesthetized and a left thoracotomy is performed, the heart is expressed from the thorax, and a ligature is placed around the proximal left coronary artery. The heart is then returned to the chest and the thorax closed. Following recovery, the rats are treated with antibody alone or in combination with a second agent of interest as outlined above. After 3-5 weeks of treatment the animals are anesthetized and cardiac function is measured as outlined above.

Canine models of chronic heart failure have also been described in the art. See, e.g., Suzuki, G., "Effects of Long-Term Monotherapy With Eplerenone, a Novel Aldosterone Blocker, on Progression of Left Ventricular Dysfunction and Remodeling in Dogs with heart failure", Circulation, vol. 106, pp. 2967-2972 (Dec. 3, 2002) (incorporated by reference into this patent). See also, Sabbah, H. N., et al., "A canine model of chronic heart failure produced by multiple sequential coronary microembolizations", *Am. J. Physiol.*, 260: H1379 1991 (incorporated by reference into this patent). This model can be used to evaluate the therapies contemplated herein.

In this study, mongrel dogs undergo serial coronary microembolizations to produce heart failure. Embolizations are performed 1 to 3 weeks apart, and are discontinued when left ventricular ejection fraction is 30% to 40%0. Microembolizations are performed during cardiac catheterization under general anesthesia and sterile conditions. Anesthesia consists of a combination of intravenous injections of oxymorphone (0.22 mg/kg), diazepam (0.17 mg/kg), and sodium pentobarbital (150 to 250 mg to effect).

Two weeks after the last microembolization, the dogs undergo a pre-randomization left and right heart catheterization. One day later, the dogs are randomized, and then assigned to one of the following treatment groups: (1) dogs receiving no treatment; (2) dogs receiving an antibody of interest at a dosing of interest, (3) dogs receiving a combination therapy of the invention, and (4) dogs receiving the second therapeutic agent used in the combination therapy at a dosing of interest. This treatment is continued for 3 months.

Final hemodynamic and angiographic measurements are made at the end of the 3 months. While under anesthesia, the each dog's chest is opened, the heart is removed, and tissue is prepared for biochemical and histological evaluations.

During this experiment, the groups of dogs are compared with respect to, for example, changes in left ventricular ejection fraction; end-diastolic volume; end-systolic volume; peak left ventricular +dP/dt; peak left ventricular −dP/dt; pulmonary artery pressure; the time constant of isovolumic relaxation, r, left ventricular end-diastolic and end-systolic axes ratios (which, in turn, indicate changes in left ventricular chamber sphericity); left ventricular end-diastolic wall stress; body weight; heart weight (normalized with body weight); left ventricular wall thickness; Na+, K+, BUN, and creatinine; mean aortic pressure; and heart rate. Comparisons also are made with respect to, for example, cardiac myocyte cross-sectional area (which, in turn, is a measure of cell hypertrophy), volume fraction of interstitial fibrosis, and volume fraction of replacement fibrosis, and capillary density, gelatinase activity, and transcription of basic fibroblast growth factor.

Another exemplary model that may be used to monitor treatment is a canine model of pacing induced heart failure. This model is well known to those of skill and is described in for example in Katsuya, et. al., *J Cardiovasc Pharmacol* 43: 860 2004. To induce heart failure by rapid right ventricular pacing, a modified multiprogrammable pacemaker (Medtronics, Inc.) is implanted in healthy adult male, mongrel dogs. After full recovery from the instrumentation (10 to 14 days after surgery), the animals are subjected to rapid ventricular pacing at 240 bpm. On the eighth day of pacing the dogs are assigned to the one of the following treatment protocols: (1) dogs receiving no treatment; (2) dogs receiving an antibody of interest at a dosing of interest, (3) dogs receiving a combination therapy of the invention, and (4) dogs receiving the second therapeutic agent used in the combination therapy at a dosing of interest. After 4 weeks of pacing, the pacemaker was turned off and the animals were allowed to equilibrate for 30 to 40 minutes. Hemodynamic and cardiac measurements are then done as outlined above.

Pharmaceutical Preparations

The NPRA specific antibodies used in the practice of a method of the invention may be formulated into pharmaceutical compositions comprising a carrier suitable for the desired delivery method. Suitable carriers include any material which, when combined with the antibody, retains the high-affinity binding and ligand potentiating properties of the antibody and is preferably nonreactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Exemplary antibody concentrations in the formulation may range from about 0.1 mg/ml to about 200 mg/ml or from about 0.1 mg/mL to about 50 mg/mL, or from about 0.5 mg/mL to about mg/mL, or alternatively from about 2 mg/mL to about 10 mg/mL. An aqueous formulation of the antibody may be prepared in a pH-buffered solution, for example, at pH ranging from about 4.5 to about 6.5, or from about 4.8 to about 5.5, or alternatively about 5.0. Examples of buffers that are suitable for a pH within this range include acetate (e.g. sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

Tonicity agents to stabilize the antibody may be included in the pharmaceutical formulation. Exemplary tonicity agents include polyols, such as mannitol, sucrose or trehalose. Preferably the aqueous formulation is isotonic, although hypertonic or hypotonic solutions may be suitable. Exemplary concentrations of the polyol in the formulation may range from about 1% to about 15% w/v.

A surfactant may also be added to the antibody formulation to reduce aggregation of the formulated antibody and/or minimize the formation of particulates in the formulation and/or reduce adsorption. Exemplary surfactants include nonionic surfactants such as polysorbates (e.g. polysorbate 20, or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

The antibodies also may be formulated with various preservatives (e.g., benzyl alcohol, phenol, m-cresol, chlorobutanol and benzethonium Cl.) If preservatives are present, they may be included in the formulation at concentrations ranging from about 0.1% to about 2%, or alternatively from about 0.5% to about 1%. One or more other pharmaceutically acceptable carriers, excipients or stabilizers such as those described in Remington's The Practice and Science of Pharmacy 21$^{st}$ Edition. (2005) may be included in the formulation provided that they do not adversely affect the desired characteristics of the fonrmulation. Acceptable carriers, excipients or stabilizers are nontoxic to recipients at the dosages and concentrations employed and include; additional buffering agents; co-solvents; antoxidants including ascorbic acid and methionine; chelating agents such as EDTA; metal complexes (e.g. Zn-protein complexes); biodegradable polymers such as polyesters; and/or salt-forming counterions such as sodium.

Therapeutic formulations of the antibody are prepared for storage by mixing the antibody having the desired degree of purity with optional physiologically acceptable carriers, excipients or stabilizers (Remington's The Practice and Science of Pharmacy 21$^{st}$ Edition. (2005)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, maltose, or dextrins; chelating agents such as EDTA; sugars such as sucrose, mnannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In one embodiment, a suitable formulation of the claimed invention contains an isotonic buffer such as a phosphate, acetate, or TRIS buffer in combination with a tonicity agent such as a polyol, Sorbitol, sucrose or sodium chloride which tonicifies and stabilizes. One example of such a tonicity agent is 5% Sorbitol or sucrose. In addition, the formulation could optionally include a surfactant such as to prevent aggregation and for stabilization at 0.01 to 0.02% wt/viol. The pH of the formulation, may range from 4.5-6.5 or 4.5 to 5.5, Other exemplary descriptions of pharmaceutical formulations for antibodies may be found in US 2003/0113316 and U.S. Pat. No. 6,171,586.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. The compositions of the invention may be sterilized by conventional, well known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration. Methods of freez-drying polypeptides for long term storage are well known, (Williams and Polli, *Journal of Parenteral Science and Technology,* 38:48, 1984. The lyophilization cycle involves freezing, primary drying, and secondary drying. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration; Chen, *Drug Development and Industrial Pharmacy,* 18: 1311, 1992.

Excipients have been noted in some cases to act as stabilizers for freeze-dried products; Carpenter et al., *Developments in Biological Standardization,* 74: 225, 1991. For example, known excipients include polyols (including mannitol, sorbitol and glycerol); sugars (including glucose and sucrose); and amino acids (including alanine, glycine and glutamic acid).

In addition, polyols and sugars are also often used to protect polypeptides from freezing and drying-induced damage and to enhance the stability during storage in the dried state, in general, sugars, in particular disaccharides, are effective in both the freeze-drying process and during storage. Other classes of molecules, including mono- and di-saccharides and polymers such as PVP, have also been reported as stabilizers of lyophilized products.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention may be designed to be short-acting, fast-releasing, long-acting, or sustained-releasing as described herein. Thus, the pharmaceutical formulations may also be formulated for controlled release or for slow release.

Specific dosages may be adjusted depending on conditions of disease, the age, body weight, general health conditions; sex, and diet of the subject, dose intervals, administration routes, excretion rate, and combinations of drugs. Any of the above dosage forms containing effective amounts are well within the bounds of routine experimentation and therefore, well within the scope of the instant invention.

The specific binding agent or antibody is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the specific binding agent or antibody is suitably administered by pulse infusion, particularly with declining doses of the specific binding agent or antibody. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. Most preferably, the specific binding agent or antibody of the invention is administered intravenously in a physiological solution at a dose ranging between 0.01 mg/kg to 100 mg/kg at a frequency ranging from daily to weekly to monthly (e.g. every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of 2 or 3 times per week, or up to 45 mg/kg once a month. Another preferred method of administration is through inhalation.

Combination Therapy

The term "combination therapy" means the administration of two or more therapeutic agents to treat a pathological condition. In this specification, the pathological condition generally comprises a cardiovascular condition or a condition associated with a cardiovascular condition. The therapeutic agents of the combination generally may be co-administered in a substantially simultaneous manner, such as, for example, (a) in a single formulation (e.g., a single capsule) having a fixed ratio of active ingredients, or (b) in multiple, separate formulations (e.g., multiple capsules) for each agent. The therapeutic agents of the combination may alternatively (or additionally) be administered at different times. In either case, the chosen treatment regimen preferably provides beneficial effects of the drug combination in treating the condition.

In the context of combination therapy, the phrase "therapeutically-effective" qualifies the amount of each therapeutic agent that will achieve the goal of ameliorating, suppressing, eradicating, reducing the severity of, decreasing the frequency of incidence of preventing, reducing the risk of, and/or delaying the onset of a pathological condition.

The treatment of heart disease includes standard treatments such as use of angiotensin II converting enzyme (ACE) inhibitors, β-adrenoceptor inhibitors, and aspirin. Any such standard therapies may be combined with therapeutic intervention using the antibodies of the present invention. Angiotensin receptor blockers may also be used in patients who do not tolerate ACEI's, and candesartan has recently been approved for use in combination with ACEI's. Aldosterone antagonists such as for example, eplerenone, also have proven effective in the treatment of heart failure and hypertension. The antibodies of the invention also could be used in combination with statin therapy in heart failure.

The antibodies described herein may be used in combination with rennin inhibitors, such as for example aliskiren (Tekturna, Rasilez, Novartis). Endothelin antagonists and vasopeptidase inhibitors (dual ACE/neutral endopeptidase (NEP) inhibitors) also may be useful in combination therapies. Combination therapies with vasopressin antagonists also may be useful. Also contemplated for combination therapy are diuretic agents such as A1 adenosine receptor antagonists. Other useful agents include beta blocker agents for the treatment of CHF.

Inotropic agents such as digoxin have long been used to relieve the symptoms of severe CHF. Milrinone is a PDE3 inhibitor and inotropic agent that is used only for short term treatment of acute CHF because this class of agents is proarrhythmiagenic and can have a negative impact on survival with chronic use. Cardiac myosin activators also may prove useful in combination with the therapies of the present invention. Also contemplated for use in the combination therapies of the present invention are PDE5 inhibitors e.g., Viagra, Cialis as well as soluble GC activators/stimulators currently in clinical trials.

Combination of the antibodies of the invention with Nesiritide (hBNP) and other natiuretic peptides (either recombinant or naturally isolated) is particularly contemplated. The antibodies may be combined with Nesiritide, Carperitide (ANP, Suntory, now Daiichi-Sankyo), Ularitide (urodilatin, PDL, EKR Therapeutics) and combination of all three are particularly contemplated.

The phrase "aldosterone antagonist" embraces an agent or compound, or a combination of two or more of such agents or compounds, which counteract the effect of aldosterone. Such agents and compounds, such as mespirenone, may antagonize the action of aldosterone through a pre-receptor mechanism. Other agents and compounds, such as spironolactone and eplerenone, fall generally within a class known as aldosterone receptor antagonists, which bind to mineralocorticoid receptors to prevent natural ligand activation of post-receptor events. Many suitable aldosterone antagonists are described by, for example, Perez et al. in U.S. Pat. No. 6,410,524 (issued Jun. 25, 2002; filed Nov. 5, 1999 as U.S. patent application Ser. No. 09/434,685) (incorporated by reference into this patent).

The aldosterone antagonists used in the methods of the present invention generally are spirolactone-type steroidal compounds as exemplified by spirolactone itself. The epoxysteroidal aldosterone antagonist compounds also may be used in the combination therapies contemplated herein. Of particular interest is the compound eplerenone (also known as epoxymexrenone). Eplerenone is an aldosterone receptor antagonist, and has a greater specificity for aldosterone receptors than does, for example, spironolactone. Selection of eplerenone as the aldosterone antagonist in the present method would generally tend to be beneficial for reducing certain side-effects, such as, for example, gynecomastia (which tends to occur when less-specific aldosterone antagonists are used).

The term "diuretic" includes, for example, diuretic benzothiadiazine derivatives, diuretic organomercurials, diuretic purines, diuretic steroids (including diuretic steroids having no substantial activity as an aldosterone receptor antagonist), diuretic sulfonamide derivatives, diuretic uracils, etc. Exemplary such compounds include amanozine, amiloride, arbutin, chlorazanil, ethacrynic acid, mannitol, metochalcone, muzolimine, perhexyline, and urea which can be purchased from commercial sources. The diuretic compound also may be a benzothiadiazine derivative, a sulfonamide derivative an organic mercurial diuretic such as mercaptomerin sodium, merethoxylline, procaine, and mersalyl with theophylline. In specific examples the diuretic is amiloride, ethacrynic acid, triamterene, hydrochlorothiazide, chlorothiazide, bumetamide, furosemide, or hydrochlorothiazide.

The present invention further comprises kits that are suitable for use in performing the methods of treatment described above. In one embodiment, the kit comprises a first dosage form comprising antibody of the invention and a second dosage form comprising a second agent for a pathological condition (e.g., a cardiovascular condition or a condition associated with a cardiovascular condition) in quantities sufficient to carry out the methods of the present invention, Preferably, the first dosage form and the second dosage form together comprise a therapeutically-effective amount of the agents for the treatment of the targeted condition(s).

EXAMPLES

The following examples are offered by way of illustration and are not meant to be limiting in any way.

Example 1

Generation of Stable Cell Lines expressing Natriuretic Peptide Receptors

Full-length human NPRA, human NPRB, human NPRC, rhesus monkey NPRA and canine NPRA sequence containing plasmids are purchased from OriGene Technologies, Inc. (Rockville, Md.) or the sequences are synthesized by DNA2.0 then sub-cloned into the pcDNA3.1 mammalian expression vector (Invitrogen Corporation, Carlsbad, Calif.). Insert orientation and nucleotide sequence of each construct is verified by an outside vendor. The pcDNA3.1 NPR clones are transfected using Lipofectamine (Invitrogen) into HEK293 cells where stable cell lines are selected using G418. NPRA and NPRB clones are screened using the ANP- or CNP-(Sigma-Aldrich, St. Louis, Mo.) induced cGMP assay described below. NPRC clones are screened using the $^{125}$I-ANP binding assay outlined below. High cGMP producing or high $^{125}$I-ANP binding clones are expanded in DMEM containing, 100 µg/mL penicillin/streptomycin, L-glutamine, 400 µg/mL of G418, and 10% fetal bovine serum (Hyclone, Logan, Utah). HEK293T-GCA, rat NPRA expressing cells obtained from Dr. Lincoln Potter (University of Minnesota), are grown in DMEM containing 100 µg/mL penicillin/streptomycin, L-glutamine, Hygromycin B and 10% fetal bovine serum.

Example 2

Generation of NPRA-Fc Fusion Protein

A. Construction of the NPRA-Fc Fusion Protein

The extracellular domain (ECD) of NPRA is fused to human Fc (gamma 1) to obtain a soluble form of NPRA. To accomplish this, plasmid pcDNA3.1-kappa-leader-MORxx-Fc is first restricted with KpnI (MORxx encoding for unnamed control protein). An oligolinker containing a ClaI site is inserted into the KpnI site via cohesive ends. The oligolinker is produced by annealing two oligonucleotides (with partial complementarity. The resulting plasmid is restricted with ClaI and EcoRV, which entails excision of the MORxx encoding sequence. The sequence encoding the extracellular domain (ECD) of NPRA is amplified from the NPRA encoding plasmid (pcDNA3.1D/V5-His-TOPO-NPRA) by PCR using primers introducing restrictions sites for ClaI and SmaI, respectively. The PCR product is restricted with ClaI and SmaI, purified and the fragment was ligated into the above plasmid yielding a fusion of the kappa-leader, the extracellular domain of NPRA and human Fc. The resulting plasmid is called pcDNA3.1_kappa-leader_NPRA-ECD_Fc.

B. Expression of the NPRA-Fc Fusion Protein

HEK293 cells are transfected with pcDNA3.1_kappa-leader_NPRA-ECD_Fc using a calcium phosphate-based transfection procedure. On days 5 or 6 post-transfection, the cell culture supernatant (1500 mL) is harvested, cleared by centrifugation and sterile filtrated (0.2 µm). Aliquots of the supernatant are frozen at −20° C.

Example 3

Methods Used for the Identification and Generation of Human NPRA-Specific Antibodies from the HuCAL GOLD® Library For the generation of therapeutic antibodies against the human NPRA protein, selections with the MorphoSys HuCAL GOLD® phage display library are carried out, HuCAL GOLD® is a Fab library based on the HuCAL® concept [Knappik et al., *J. Mol. Biol.*, 296, 57, 2000; Krebs et al., *J. Immunol. Methods*, 254, 67, 2001; Rauchenberger et al., *J Biol. Chem.*, 278, 38194, 2003], in which all six CDRs are diversified, and which employs the CysDisplay™ technology for linking Fab fragments to the phage surface [Löhning, WO 01/05950, (2001)].

A. Phagemid Rescue, Phage Amplification, and Purification

The HuCAL GOLD® library is amplified in 2×YT medium containing 34 µg/ml chloramphenicol and 1% glucose (2×YT-CG). After infection with VCSM13 helper phages at an $OD_{600nm}$ of 0.5 (30 min at 37° C. without shaking; 30 min at 37° C. shaking at 250 rpm), cells are spun down (4120 g; 5 min; 4° C.), resuspended in 2×YT/34 µg/ml chloramphenicol/50 µg/ml kanamycin/0.25 mM IPTIG and grown overnight at 22° C. Phages are PEG-precipitated from the supernatant, resuspended in PBS/20% glycerol and stored at −80° C. Phage amplification between two panning rounds is conducted as follows: mid-log phase *E. coli* TG1 cells are infected with eluted phages and plated onto LB-agar supplemented with 1% of glucose and 34 µg/ml of chloramphenicol (LB-CG plates). After overnight incubation at 30° C., the TG1 colonies are scraped off the agar plates and used to inoculate 2×YT-CG until an $OD_{600nm}$ of 0.5 is reached and VCSM13 helper phages added for infection as described above.

B. Solid Phase Panning against Captured NPRA-Fc with huCAL GOLD®

This example describes solid phase panning which is used for selection. HuCAL GOLD® antibody-phage are divided into three pools corresponding to different VH master genes in combination with lambda and kappa light chains (pool 1: VH1/5 lambda & kappa, pool 2: VH3 lambda & kappa, pool 3: VH2/4/6 lambda & kappa). An additional pool (pool 4) is composed of VH3 lambda & kappa of HuCAL GOLD® antibody-phage Hyperphage preparation. These pools are individually subjected to 3 rounds of solid phase panning on NPRA-ECD-Fc captured on maxisorp plates (F96 Maxisorp, Nunc, Rochester, N.Y.) by an anti-Fc antibody (capture antibody). In detail: The wells of a maxisorp plate are coated with 100 µl of capture antibody (goat anti-human IgG Fc gamma Fragment specific, Dianova, Hamburg Germany, 10 µg/ml in PBS). 3 wells per phage pool are coated. The plate is incubated overnight at 4° C. On the next day the wells are washed three times with PBS and then blocked with 200 µl of MTBST (TBS, 0.05% Tween 20, 5% milk powder) for 2 h at IRT. After washing three times with PBS, 100 µl of the NPRA-ECD-Fc containing cell supernatant are added and the plate is incubated at RT for 4 h. Then the supernatant is discarded and 100 µl of fresh supernatant are added. The plate is stored overnight at 4° C.

The phage are arranged in 4 pools as described above. 100 ul of the phage from original HuCAL GOLD® subpools (VH1-6) each or of subpool VH3 (HuCAL GOLD® Hyperphage preparation) are used, corresponding to 1.7-8.0×10$^{12}$ phage. The phage are preblocked in a TBS solution containing 2.5% milk powder, 0.05% Tween 20, 1% IgG Serum Goat (Dianova), 1% IgG Serum human (Dianova) and 2.5% FCS (PAN Biotech GmbH). The pre-blocking of phage is performed in 2 ml reaction tubes for 2 h at RT on a rotator.

For the selection process the NPRA-ECD-Fc supernatant is removed from the maxisorp plate and the wells are washed three times with PBS. The pre-blocked phage are added to the corresponding wells and the plate is incubated for 2 h at RT on a microplate shaker. Then the phage solution is removed and the wells are washed as follows: three times with PBST (PBS, 0.05% Tween 20), twice with PBST (with an incubation of 5 min between the washing steps), three times with PBS and finally twice with PBST (with an incubation of 5 min between washing steps). For elution of specifically bound phage 150 µl of 20 mM DTT in 10 mM Tris/HCl, pH 8.0 is added and the samples are incubated for 10 min at RT. The eluates are used to infect log phase *E. coli* TG1 cultures. Infected *E. coli* are harvested by centrifugation and plated onto LB agar plates supplemented with 34 µg/ml chloramphenicol and 1% glucose. The agar plates are incubated overnight at 30° C. On the following day the colonies are scraped off and grown until reaching an OD of 0.5 to proceed to helper phage infection.

Helper phage infection: TG1 cells are infected with the helper phage VCSM13 (multiplicity of infection of ~20) at 37° C. The infected cells are harvested by centrifugation and resuspended in 2×YT containing 34 μg/ml chloramphenicol, 50 μg/ml kanamycin and 0.25 mM IPTG for induction of Fab expression. The cells are grown overnight and the produced phage are precipitated from the supernatant with polyethylene glycol (PEG)/NaCl and resuspended in PBS. Input and output titers are determined by spot titration.

Three rounds of selection are performed with increasing washing stringency. Between each round the eluted phage are precipitated as described above, C. Alternating Panning Using NPRA Expressing Cells Selections can also are performed using whole cell panning with cells that express the receptor. For these selections, HuCAL GOLD® antibody-phage are divided into three pools as described above and an additional pool (pool 4) is composed of VH3 lambda & kappa of HuCAL GOLD® antibody-phage Hyperphage preparation. These pools are individually subjected to one round of solid phase panning on NPRA-ECD-Fc, followed by one round on NPRA-expressing HEK cells, followed by another round of solid phase panning. The 1st round and 3rd round solid phase pannings are performed as described in section 3.4.1. The 2nd round panning is a whole cell panning on NPRA-expressing HEK cells followed by pH-elution.

More particularly, in the second round, all steps are carried out at 4° C. and in a volume of 1 ml in total. After detachment in Versene (Gibco Invitrogen, Carlsbad, Calif.) cells are washed twice in blocking buffer (5% FCS/0.05% NaN3/PBS) and adjusted to $1.0 \times 10^7$ cells for each antibody phage pool. The phage selected from the 1st round of the panning are incubated in blocking buffer for 2 h and then added to the pre-blocked cells for 2 h under constant movement. Afterwards, cells are washed five times in blocking buffer followed by incubation in 1 ml elution buffer (0.1 M glycine, 0.5 mM NaCl, pH 2.2) for 10 min without shaking. Cells are removed by centrifugation and the supernatant neutralized by the addition of unbuffered 2 M Tris solution.

The eluate is mixed with a 15 ml culture of *E. coli* TG1 grown to an OD600 nm of 0.6-0.8 and incubated for 45 min at 37° C. After centrifugation the bacterial pellet is resuspended in 2×YT medium, plated on 2×LB/Chloramphenicol/Glucose agar plates and incubated overnight at 30° C. The selected clones are then scraped from the plates, rescued and amplified as described above.

D. Alternating Panning Against NPRA in the Presence of ANP and BNP

Selection can also be performed in the presence of the ligands for NPRA. For these selections, HuCAL GOLD® antibody-phage are not divided into three pools, but all different VH master genes in combination with lambda and kappa light chains are mixed and subjected to one round of solid phase panning on NPRA-ECD-Fc, followed by one round on NPRA-expressing HEK cells, followed by another round of solid phase panning.

Nevertheless two different pools are made, pool 1 consisting of HuCAL GOLD® antibody phage normal preparation, pool 2 consisting of HuCAL GOLD® antibody-phage Hyperphage preparation. The 1st round and 3rd round solid phase pannings are performed as described above with the following exceptions:

The blocking solution for the phage contained 3 PM ANP and BNP each. The coating with the NPRA-Fc protein is much shorter; supernatant is only added once, and the incubation is for 1 h. After this incubation the wells are washed three times with PBS, then 100 μl of ANP/BNP solution (3 μM each) is added and the plate is incubated 30 min at RT on a microplate shaker. 8 wells per pool are coated for the selection.

The 2nd round panning is a whole cell panning on NPRA-expressing HEK cells followed by pH-elution as described above with the following exceptions: The blocking solution for the phage contained 400 nM ANP and BNP each. After harvesting the NPRA-transfected HEK-cells are resuspended in blocking buffer containing 1 μM ANP. The mixture of cells and ANP is incubated 30 min at 4° C. under constant movement before adding the blocked phage, E. Subcloning and Expression of Soluble Fob Fragments The Fab-encoding inserts of the selected HuCAL GOLD® phagemids are sub-cloned into the expression vector pMORPH®X9_tab_FH or the bivalent expression vector pMORPH®X9_Fab_dHLX_MH respectively in order to facilitate rapid and efficient expression of soluble Fabs. For this purpose, the plasmid DNA of the selected clones is digested with XbaI and EcoRI, thereby excising the Fab-encoding insert (ompA-VLCL and phoA-Fd), and cloned into the XbaI/EcoRI-digested expression vectors. Fabs expressed from these vectors carry two C-terminal tags for both, detection and purification. In case of vector pMORPH®X9_Fab_FH the tags are FLAG™ and 6×His; in case of pMORH®X9_Fab_dHLX_MH the tags are myc-tag and 6×His, respectively.

F. Microexpression of HuCAL GOLD® Fab Antibodies in *E. coli*

Chloramphenicol-resistant single colonies obtained after subcloning of the selected Fabs into the pMORPH®X9_Fab_dHLX_MH expression vector are used to inoculate the wells of a sterile 96-well microtiter plate containing 100 μl 2×YT-CG medium per well and grown overnight at 37° C. 5 μl of each *E. coli* TG-1 culture is transferred to a fresh, sterile 96-well microtiter plate pre-filled with 100 μl 2×YT medium supplemented with 34 μg/ml chloramphenicol and 0.1% glucose per well. The microtiter plates are incubated at 30° C. shaking at 400 rpm on a microplate shaker until the cultures are slightly turbid (~2-4 hrs) with an $OD_{600nm}$ of ~0.5.

To these expression plates, 20 μl 2×YT medium supplemented with 34 μg/ml chloramphenicol and 3 mM IPTG (isopropyl-β-thiogalactopyranoside) is added per well (end concentration 0.5 mM IPTG), the microtiter plates are sealed with a gas-permeable tape, and incubated overnight at 30° C. shaking at 400 rpm.

Generation of whole cell lysates (BEL extracts): To each well of the expression plates, 40 μl BEL buffer (2×BBS/EDTA: 24.7 g/l boric acid, 18.7 g NaCl/l, 1.49 g EDTA/l, pH 8.0) containing 2.5 mg/ml lysozyme is added and incubated for 1 hr at 22° C. on a microtiter plate shaker (400 rpm). The BEL extracts are used for primary screening in the cGMP-assay.

G. Expression of HuCAL GOLD® Fab Antibodies in *E. coli* and Purification

Expression of Fab fragments encoded by pMORPH® X9_Fab_FH in TG-1 cells are carried out in shaker flask cultures using 750 ml of 2×YT medium supplemented with 34 μg/ml chloramphenicol. Cultures are shaken at 30° C. until the $OD_{600nm}$ reached 0.5. Expression is induced by addition of 0.75 mM IPTG for 20 h at 30° C. Cells are disrupted using lysozyme and Fab fragments isolated by Ni-NTA chromatography (Qiagen, Hilden, Germany). Protein concentrations is determined by UV-spectrophotometry [Krebs et al., *J. immunol. Methods*, 254, 67-84 (2001)].

H. Cloning of HuCAL® IgG4

In order to express full length immunoglobulin (Ig), variable domain fragments of heavy (VH) and light chains (VL) are subcloned from the pMORPH™ X9_FH Fab expression vectors into the pMORPH®_h_Ig vector series for human IgG4.1Pro. Restriction enzymes EcoRI, MfeI, and BlpI are used for subcloning the VH domain fragment into pMORPH®_h_IgG4.1 Pro: the vector backbone is generated by EcoRI/BlpI digestion and extraction of the 6400 bp fragment whereas the VH fragment (350 bp) is produced by digestion with MfeI and BlpI and subsequent purification. Vector and insert are ligated via compatible overhangs generated by the EcoRI and MfeI digests, respectively, and via the BlpI site. Thereby, both the EcoRI and the MfeI restriction site are destroyed. Subcloning of the VL domain fragment into pMORPH®_h_Igκ is performed via the EcoRV and BsiWI sites, whereas subcloning into pMORPH®_h_Igλ is done using EcoRV and HpaI.

I. Transient Expression and Purification of Human IgG

Eukaryotic HKB11 or HEK293 cells are transfected with an equimolar amount of IgG heavy and light chain expression vector DNA. Cell culture supernatant is harvested from 3 to 7 days post transfection. After adjusting the pH of the supernatant to 8.0 and sterile filtration, the solution is subjected to standard protein A affinity chromatography (rProteinA FF or MabSelect SURE, GE H-tealthcare), Buffer exchange is performed to 1× Dulbcecco's PBS (pH 7.2, Invitrogen) and samples are sterile filtered (0.2 µm). Purity of IgG is analyzed under denaturing, reducing conditions in SDS-PAGE or by using Agilent BioAnalyzer and in native state by SE-HPLC.

Example 4

Methods Used for the Screening of NPRA-binding Fabs

A. Screening for NPRA binding Fabs by ELISA

For some pannings ELISA is used as the primary screening method for identifying for NPRA-Fc binding Fabs. NPRA-Fc is captured in microtiter plates by a goat anti-human IgG. A nonrelevant Fc fusion protein serves as a negative control to exclude Fabs, which are directed against the human Fc. Briefly, the capture antibody, Affinity Pure Goat anti human IgG Fc-gamma specific (Dianova) at 10 µg/ml in PBS, is coated on Maxisorp® microtiter plates (Nunc) overnight at 4° C. On the following day, the wells are blocked for 1 hour with MPBST (PBS/0.05% Tween 20/5% milk powder) on a microplate shaker. NPRA-ECD-Fc containing cell supernatant is added and incubated for 1 hour at room temperature. The wells of the microtiter plate are then washed three times with PBST (PBS/0.05% Tween 20). If required, a mixture of 150 nM ANP/300 nM BNP is added and the plates are incubated and washed with PBST. Then HuCAL® Fab antibodies are added to the wells and incubated for 1 hour at room temperature. For detection of the primary antibodies, alkaline phosphatase (AP)-conjugated AffiniPure F(ab')2 fragment, goat anti-human IgG (Dianova, 109-055-097) is applied. For the development of AP-conjugates, the fluorogenic substrate AttoPhos (Roche) is used according to the instructions of the manufacturer. The plates are read in an ELISA-reader (Tecan).

B. Screening/or NPRA binding Fabs by FACS

HEK NPRAI cells are detached with Accutase (PAA Laboratories GmbH, Cat. No. L11-007, Austria), harvested by centrifuigation (900 rpm, 4 minutes) and resuspended in FACS buffer (PBS/3% FCS/0.02% NaN3) to a final concentration of $10^6$ cells/ml. 100 µl of the cell suspension is transferred to each well of a 96 round bottom plate (TC Microwell 96U, Nunc). Cells are pelleted (2000 rpm, 5 min, 4° C.), and resuspended in 100 µl of FACS buffer with or without 100 nM ANP and incubated on ice for 30 min. Cells are washed in 150 µl of FACS buffer, pelleted and resuspended in 50 µl of the solution containing the primary antibody comprising a BEL extract of Fabs, a diluted BEL extract or purified antibody diluted in FACS buffer and incubated on ice for 30 min. Cells are washed again in FACS buffer and resuspended in 50 µl of FACS buffer containing the secondary antibody (R-Phycoerythrin-conjugated Affipure F(ab')$_2$ Fragment Goat Anti-Human IgG, Dianova) and incubated on ice for 45 min. Cells are washed twice with FACS buffer and resuspended in 200 µl of FACS buffer for analysis in the FACS Array (BD Biosciences).

C. Screening for Agonistic or Potentiating Fobs in the HEK NPRA cGMP Assay

The activation of NPRA results in generation of cGMP, the amount of which is determined using the HitHunter™ cGMP Assay Kit (DiscoverX, Fremont, Calif.), The assay buffer used is PBS/0.1% BSA/25 mM HEPES containing 1 mM of the phosphodiesterase inhibitor 3-isobutyl-1-methylxanthine (IBMX, Sigma). The assay is performed according to the protocol. For a standard curve 10-fold dilutions of cG NMP between 4 pM and 4 µM are used. Fabs are screened in the dHLX-format as BEL lysates, micropurified Fabs or large scale purifications. The screening is performed in presence or absence of a suboptimal concentration of ANP (final concentration in assay 40 pM), which does not elicit a cGMP response on its own.

For the screening assay, ANP is diluted in assay buffer to a concentration of 160 pM and 7.5 µl of this solution was pipetted into the wells of a 96 round bottom well plate (TC Microwell 96U, Nunc). Then 7.5 µl of Fab is added. NPRA-transfected HEK cells are harvested, washed and resuspended in assay buffer to a final concentration of $3.3 \times 10^5$ cells per ml. 15 µl of the cell suspension is added to the wells and the plate is incubated for 15 min at 37° C. Then the cells are lysed by adding 20 µl of lysis buffer and anti cGMP antibody reagent (mixed 1:1). Immediately afterwards 20 µl of ED reagent is added and the plate is incubated for 1 h at room temperature. Then 20 µl of EA reagent is added and the plate is incubated for another 30 min. During that incubation the samples are transferred to a plate suitable for determination of luminescence (OptiPlate-96, Perkin Elmer). Then 30 µl of substrate solution (Galacton Star:Emerald II:Substrate Diluent 1:5:19) is added. Luminescence is measured in a TECAN reader after 2 to 3 h.

Example 5

Identification of a Human NPRA-specific Antibody

A. Initial Pannings.

The initial two pannings are whole cell pannings performed on NPRA-transfected HEK-cells with postadsorption on untransfected HEK-cells. One of the pannings is performed with conventional acidic elution, in the other panning the NPRA ligands ANP and BNP are added in order to displace the potential binding Fab on the antigen and thus elute the corresponding phage. From each panning 1140 candidates are screened in ELISA for NPRA-ECD-Fc binding and 276 candidates are screened in FACS for specific binding to NPRA-transfected cells. No specific Fabs are found in either screen.

Solid phase pannings are performed on immobilized NPRA-ECD-Fc and an alternating panning against NPRA.

The Fabs are subcloned into the pMx9_FH vector. The primary screening is performed via ELISA against NPRA-ECD-Fc. Out of 1532 Fabs tested, 123 show specific binding to NPRA-ECD. Fabs that bind to Fec or to the capture antibody are excluded after detection by an ELISA against a captured control Fc-protein. The secondary screening consists of a FACS scan looking for binding to NPRA-transfected LHEK-cells.

Out of 123 primary hits 49 show at least weak binding (threshold 2-fold over background). These 49 clones are sequenced and 6 unique sequences were identified. However, these Fabs do not show agonistic or potentiating activity in the cGMP assay, either in the absence of ligand or in presence of suboptimal concentrations of ANP.

With the intention of generating antibodies against the active conformation of the NPRA receptor, the activating ligands ANP and BNP are added during the a series of solid phase pannings on NPRA-ECD-Fec as well as on an alternating panning on NPRA expressing cells.

The selected Fab pool is subcloned into the pMx9_dHLX_MH vector. The primary screening is done via ELISA against NPRA-ECD-Fc in presence of ANP. Out of 1528 Fabs tested, 299 show specific binding to NPRA-ECD in presence of ANP. Fabs that bind to Fc-protein or the capture antibody are detected by an ELISA against a captured control Fc-protein and excluded. 177 of the 198 hits derived from the alternating panning are also tested for binding to NPRA-transfected HEK cells in FACS, 175 of these show specific binding. The secondary screening is performed via cGMP assay performed in presence of suboptimal concentration of ANP (40 pM) in order to allow for the detection of Fabs which would not elicit cGMP response on their own, but would elevate ANP-elicited response.

ANP at 40 pM on its own does not stimulate a detectable cGMP response in the assay. BEL extracts of the Fabs were used. Of the 299 ELISA hits 279 are tested in the cGNMP assay. None of them show significant agonistic activity, but 69 Fabs which showed a slightly elevated activity are chosen for further investigation after micropurification. Micropurification is preferred, because it yields a higher Fab-concentration and because some tests show that BEL-buffer inhibits the assay to some extent. Of the 69 Fabs 9 are chosen for further investigation based on elevated cGMP response. For 4 out of 9 significant elevation of cGMP levels are confirmed. These clones are sequenced and proven to be identical. The Fab identified is given the name 5064.

B. Characterization of HuCal Gold selected Fabs.

Several non-agonistic Fabs against NPRA when selected and converted to the IgG1 format bind to HEK hNPRA cells with EC50s between 10 and 20 nM with different saturation levels. However, none of these binders, in a monovalent (Fab) or bivalent (Fab-dHLX) format, display agonistic or potentiating activity in absence or presence of suboptimal concentrations of ANP. These antibodies are not investigated further.

Figure 1B:
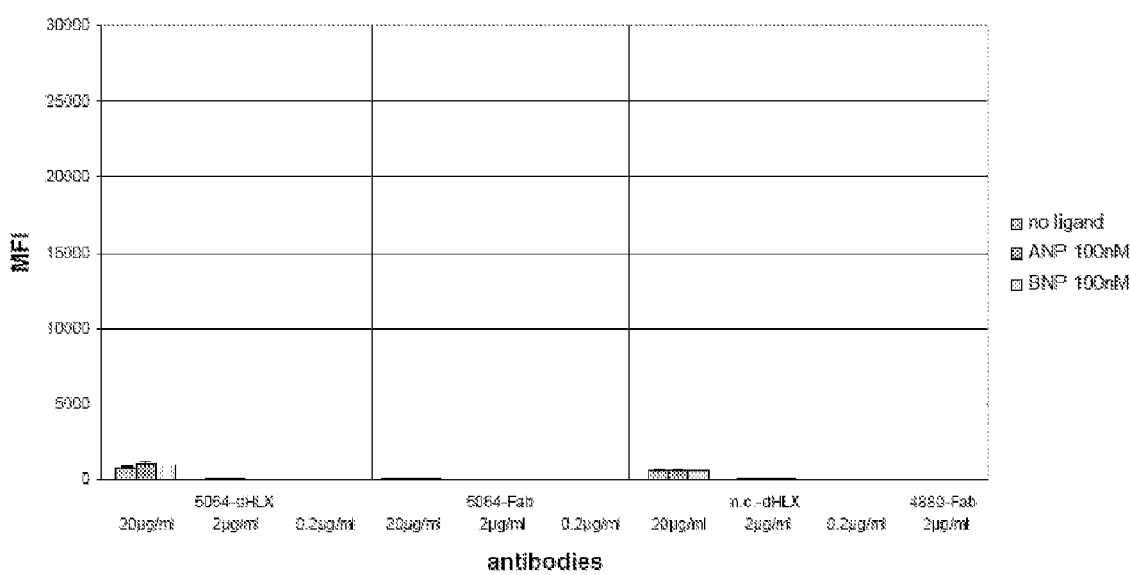
Figure 2A:
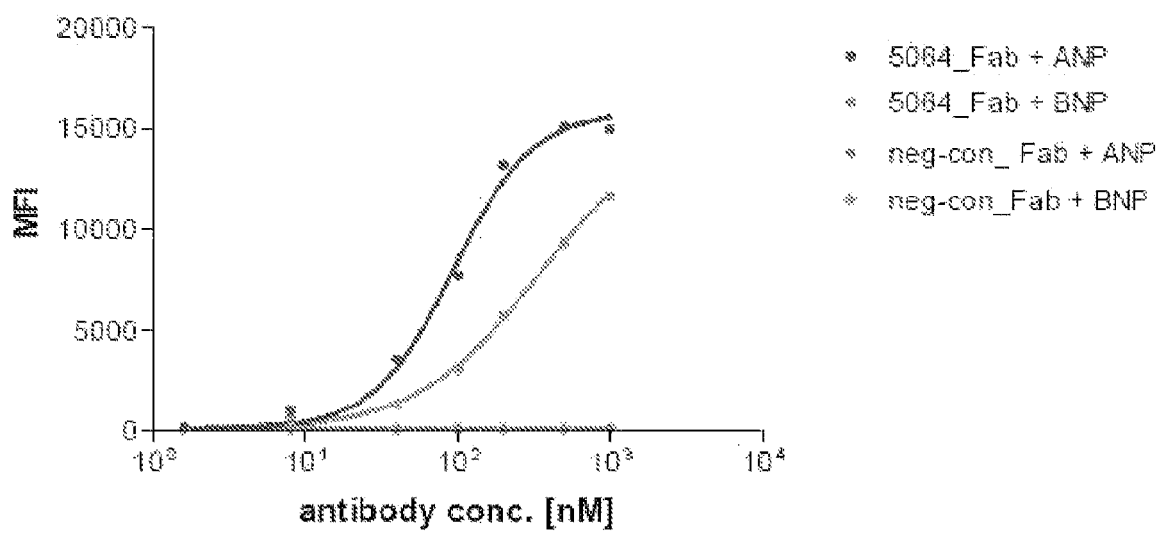
FIG. 2A, FIG. 2B and FIG. 2C: Dose Response of Binding of 5064 in Different Formats to NPRA transfected HEK cells.
Figure 2B:
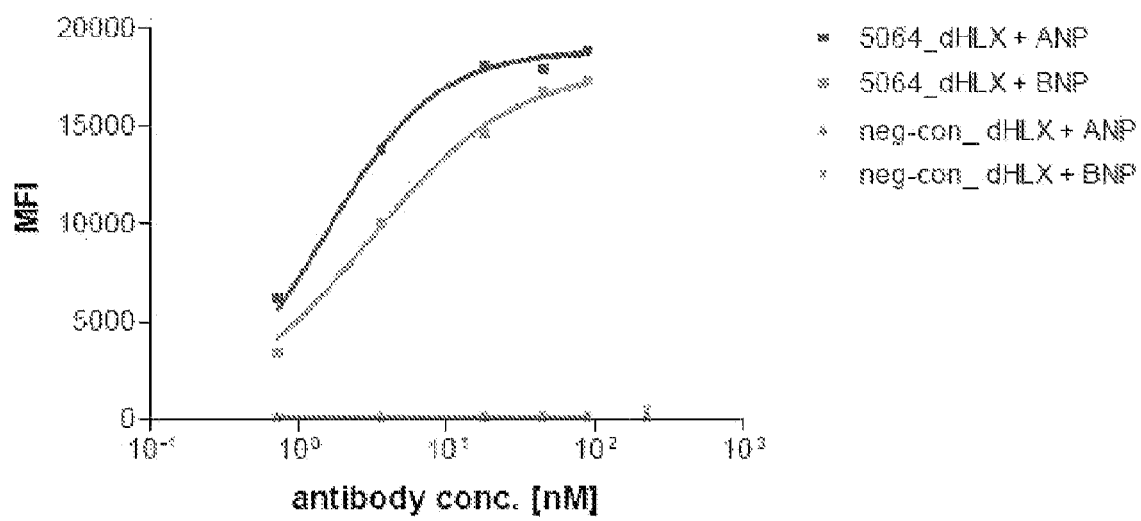
Figure 2C:
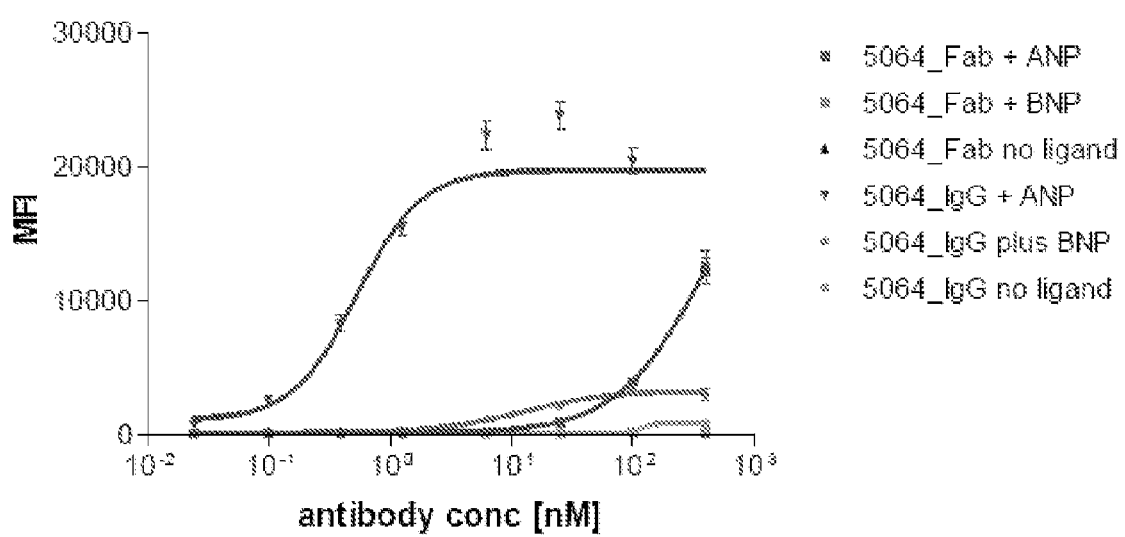

In contrast, the binder 5064, in both the monovalent (Fab) and bivalent (Fab-dHLX) formats show specific and concentration dependent binding to NPRA transfected HEK293 cells only in the presence of ANP or BNP, i.e. this binder specifically recognizes the receptor-ligand complex (FIG. 1). Fab-dHLX shows stronger binding than the Fab indicating increased avidity due to bivalency. Both monovalent and bivalent 5064 reveal stronger binding to the ANP bound receptor compared to BNP bound receptor, which may be related to the higher affinity of ANP for NPRA. Titration of 5064 Fab, Fab-dHLX and IgG1 over a broader concentration range allows an estimation of EC50 values for cell binding. 5064 Fab displays an EC50 of at least ~100 nM and ~300 nM on ANP and BINP bound HEK NPRA cells, respectively. The corresponding bivalent antibody formats, Fab-dHLX and IgG1, exhibited about 50 to 100-fold stronger binding than the Fab (FIG. 2A-2C).

Figure 3:
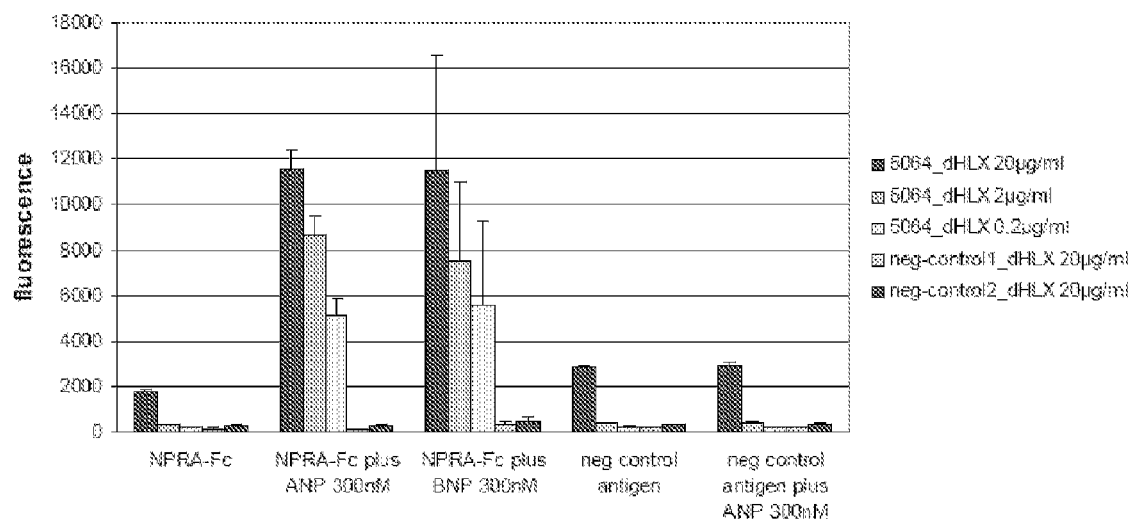
FIG. 3: Demonstration of Binding of 5064 Fab-dH LX to NPRA-Fc by ELISA. Binding was tested in presence and absence of ligands. Binding to control Fc antigen (neg control antigen) was tested in presence and absence of ANP.
Figure 4:
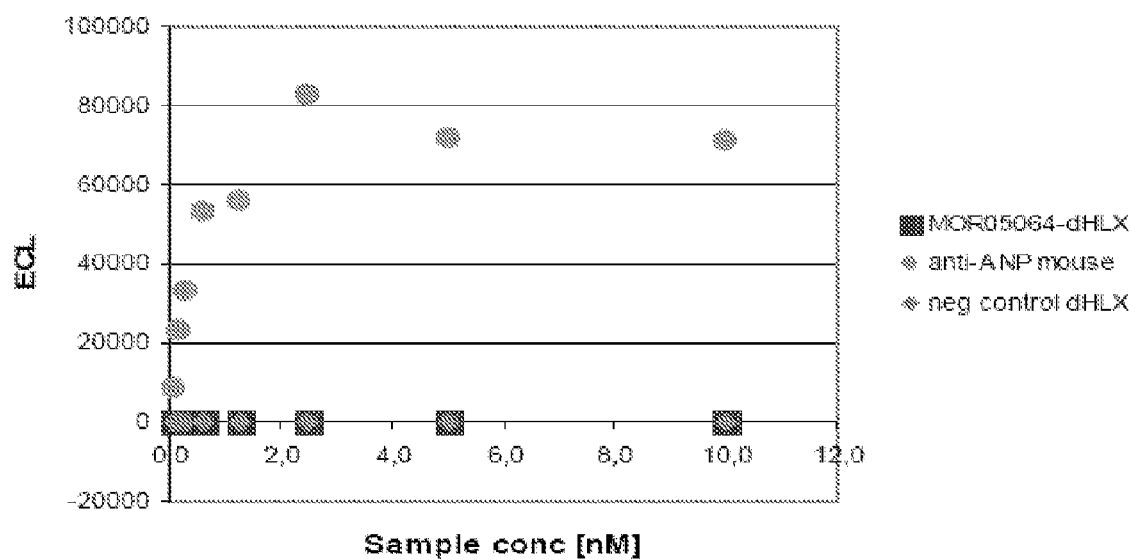
FIG. 4: 5064 Fab-dHLX Does Not Bind to Biotinylated ANP Alone by ELISA. 5064 Fab-dHLX, a negative control Fab-dHLX, and an anti-ANP mouse monoclonal antibody are tested for binding to plate bound biotinylated ANP by ELISA.
Figure 5:
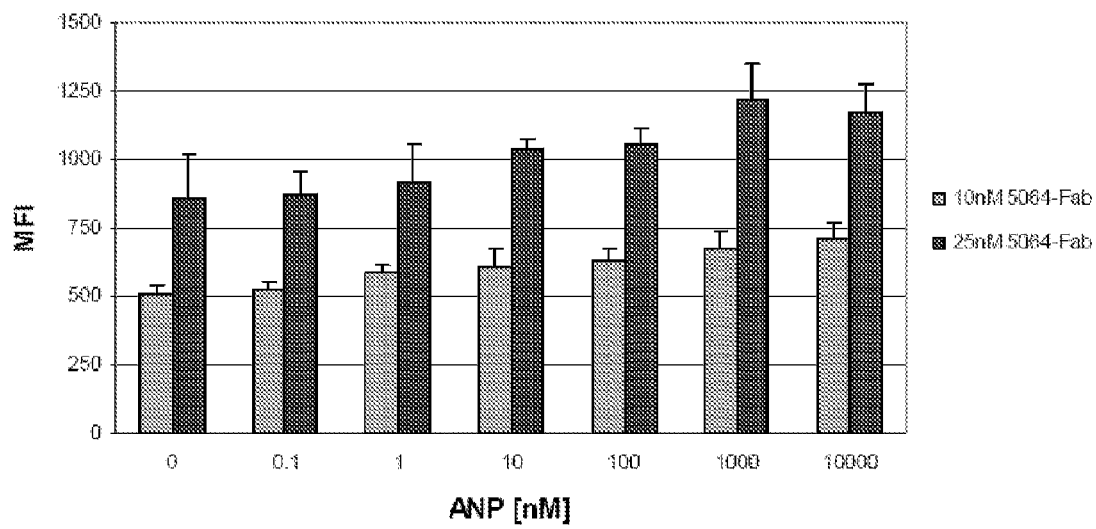
FIG. 5: Free ANP Does Not Compete with ANP Complexed NPRA for Binding of 5064 Fab. 5064 Fab is preincubated with various concentrations of ANP prior to adding to HEK NPRA cells loaded with 100 nM ANP. Binding was analyzed in FACS. MFI—mean fluorescent intensity

To further assess the specificity of the binder 5064, binding studies with recombinant NPRA-Fc are performed. As previously observed with cellular NPRA, the antibody is able to bind NPRA-Fc only when it was loaded with the ligands ANP or BNP (FIG. 3). Since it may be possible that 5064 binds only to the peptide ligands and not to the receptor, binding of the antibody to the free ligand is investigated. To this end biotin-labeled ANP is conjugated to Streptavidin beads and binding of antibodies is determined. While a positive control antibody against ANP shows significant binding, 5064 Fab-dHLX shows absolutely no binding (FIG. 4). In another experiment 5064 Fab is pre-incubated with an excess of ANP in solution before being added to H-IEK NPRA cells loaded with ANP (FIG. 5). In this setting competition with excess ANP has no effect on binding of 5064 to the ANP-NPRA complex. Taken together, these findings show that 5064 specifically recognizes the activated ligand-receptor complex, but does not interact with either receptor or natriuretic peptides alone.

Figure 6:
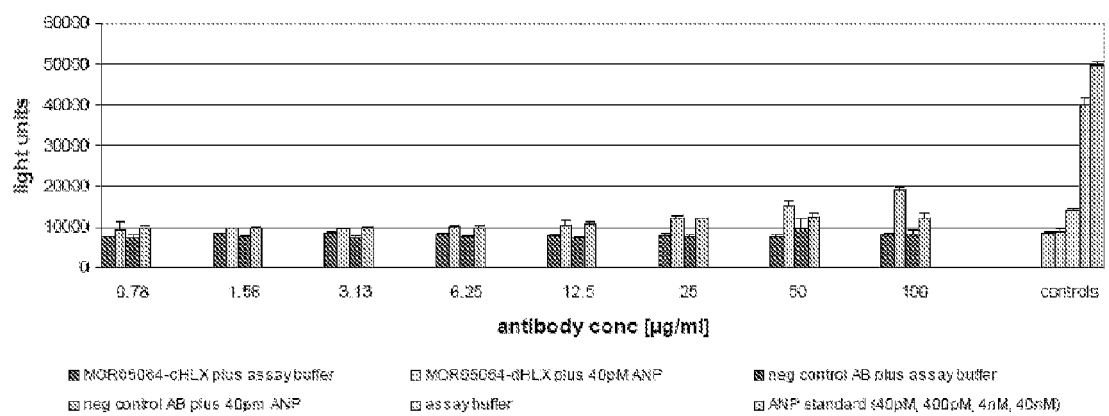
FIG. 6: 5064-dHLX Enhances NPRA-mediated cGMP Production in the Presence of Suboptimal Concentrations of ANP. HEK NPRA cells are incubated in the presence or absence of increasing concentrations of 5064-dHLX or a control antibody and 40 pM ANP and cGMP is measured as described.
Figure 7:
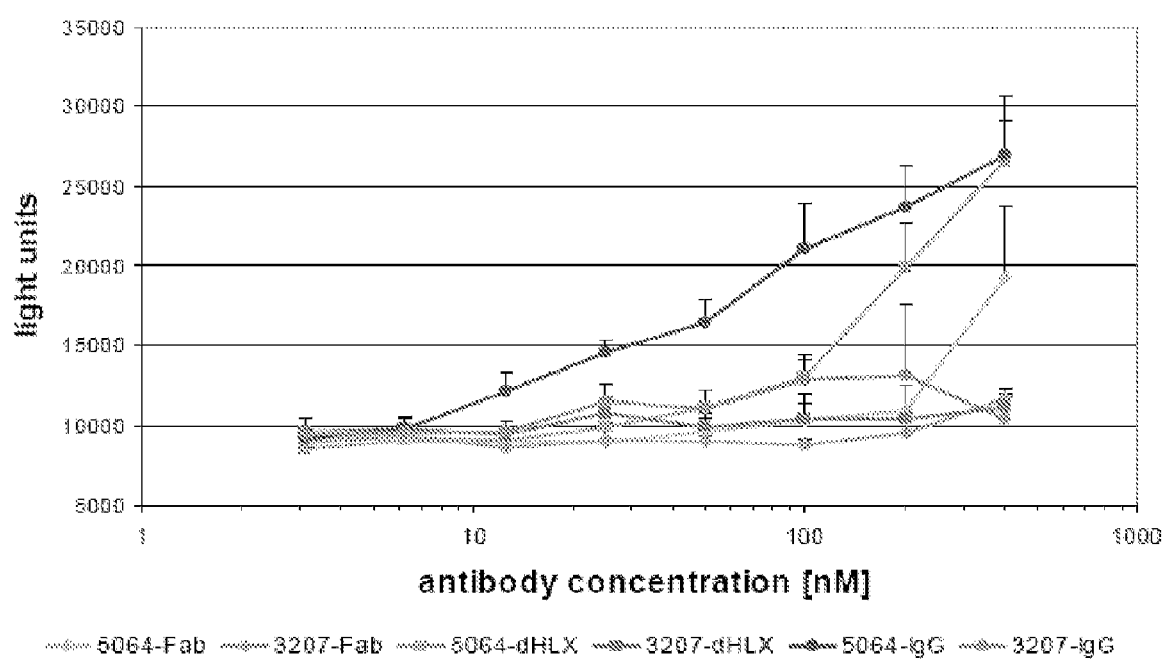
FIG. 7: 5064 Enhances NPRA-mediated cGMP Production in the Presence of Suboptimal Concentrations of BNP. HEK NPRA cells are incubated in the presence or absence of increasing concentrations of 5064-Fab dHLX or IgG, or control (3207) and 40 nMN BNP and cGMP is measured as described.

The effects of 5064 on the guanylyl cyclase activity of NPRA is evaluated by incubating the binder in the Fab-dHLX format with HEK NPRA cells in the absence or presence of 40 pM ANP and measuring NPRA dependent production of cGMP. In the absence of ANP, the cGMP response was not increased above baseline at concentrations of 5064 up to 100 μg/ml (~900 nM). In presence of 40 pM ANP a minimal cGMP signal is observed with or without negative control Fab-dHLX. However in presence of 40 pM ANP and 5064 Fab-dHLX at concentrations above 50 μg/ml (~450 nM) the cGMP level is significantly elevated (FIG. 6). A similar effect is observed when 5064 Fab, Fab-dHLX and IgG1 are tested at various concentrations in presence of 40 nM BNP, which is insufficient to induce cGMP on its own (FIG. 7). 5064 IgG enhances the NPRA dependent cGMP production at concentrations between 10 and 100 nM, it was followed by Fab-dHLX, which increases the cGMP signal at concentrations above 100 nM. The monovalent Fab showed the weakest effect, which could only be observed at the highest concentration of 400 nM.

Figure 8A:
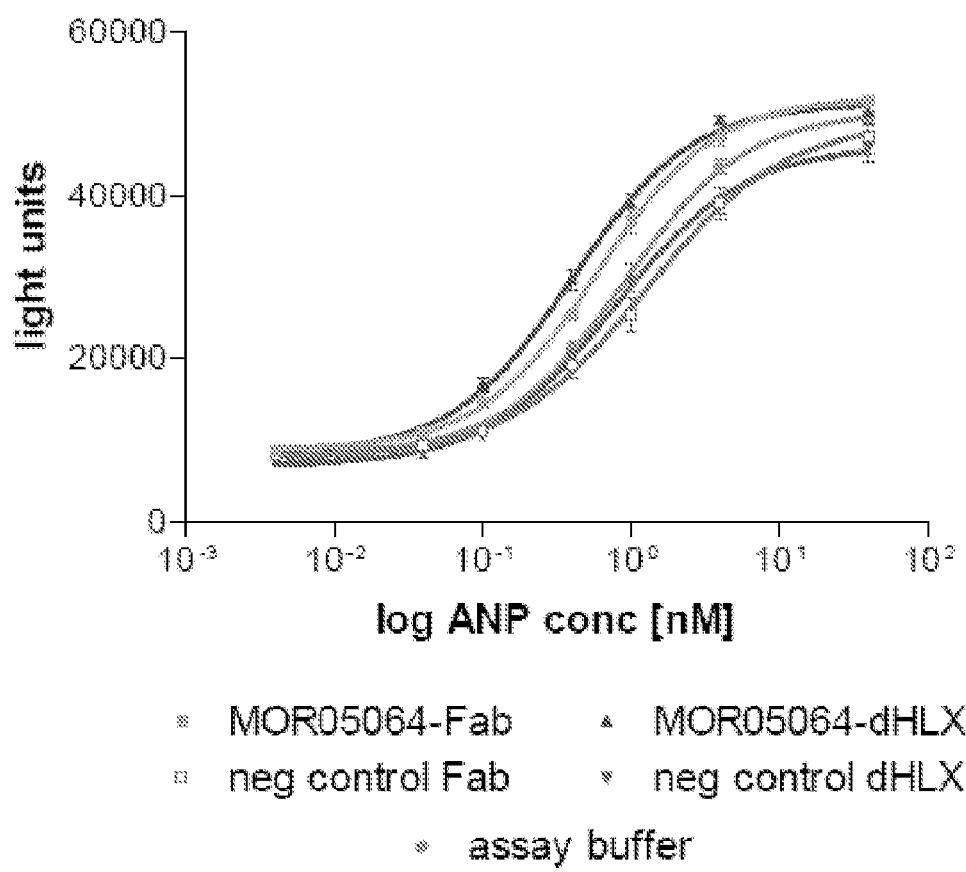
FIG. 8A and FIG. 8B: Effects of 5064 Fab and Fab-dHLX on ANP and BNP stimulated cGMP responses in HEK NPRA cells. 20 µg/ml 5064 Fab or Fab-dHLX or control Fabs are incubated with HEK NPRA cells in the presence of increasing concentrations of ANP (FIG. 8A) or BNP (FIG. 8B) and cGMP is quantitated as described.
Figure 8B:
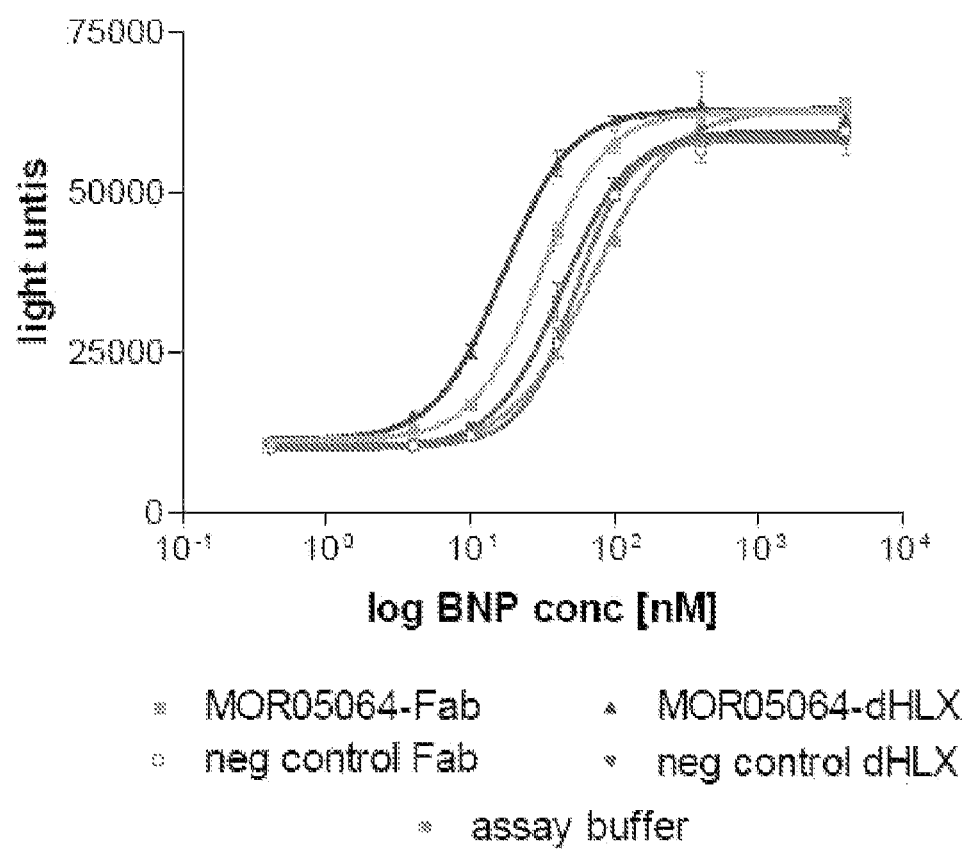
Figure 9:
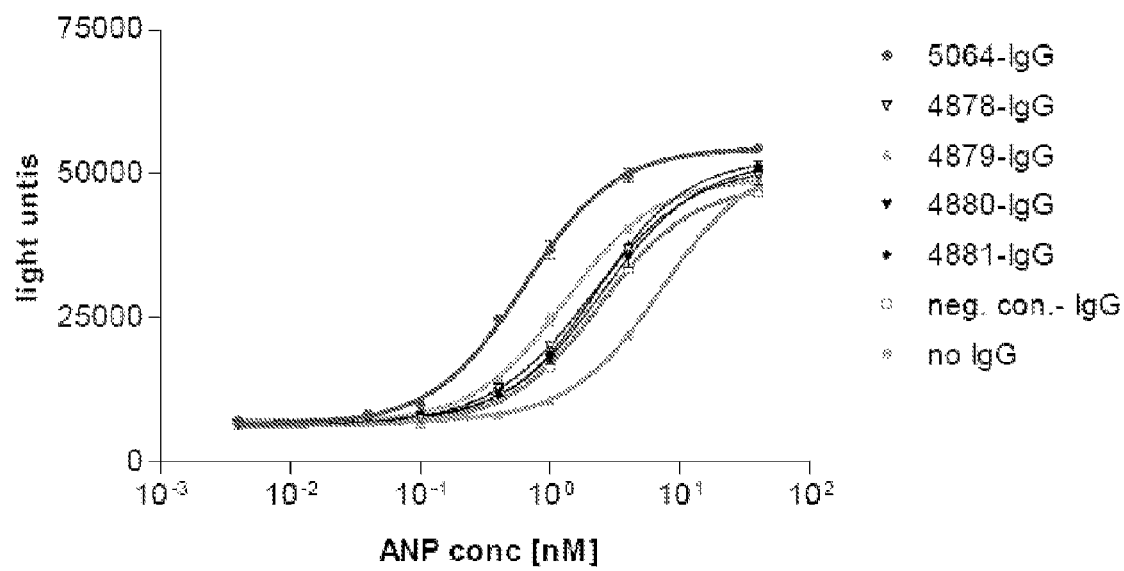
FIG. 9: The 5064 IgG uniquely potentiates ANP mediated NPRA activation. 200 nM 5064 IgG1, and other NPRA binders 4878, 4879, 4880 are added to NPRA HEK cells in the presence of increasing concentrations of ANP and cGMP is measured as described.
Figure 10:
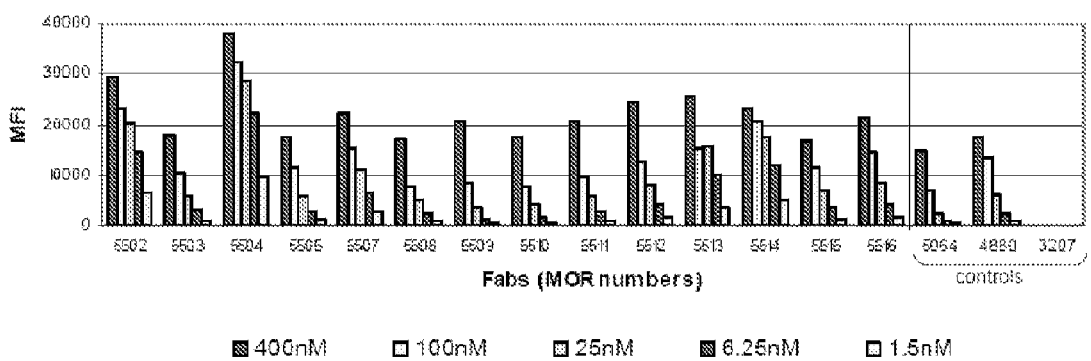
FIG. 10: Affinity matured Fabs bind to HEK NPRA cells complexed with ANP to a greater extent than the parental Fab 5064. HEK NPhRA cells are loaded with 100 nM ANP. Whole cell Fab binding is monitored by FACS analysis and the non-potentiating NPRA-specific Fab 4880 and negative control Fab 3207 are also included as controls. MFI—mean fluorescent intensity

To further assess the effects of 5064 on the potency of ANP and BNP in the activation of NPRA, 20 μg/ml of 5064 or a negative control Fab or Fab-dHLX is added to HEK NPRA cells in the presence of increasing concentrations of ANP or BNP and cGMP production is measured. In the presence of either 5064 Fab or Fab-dHLX the potency of ANP and BNP is increased by 2 to 3-fold as seen by a shift of the dose-response curves to the left (FIG. 8A and FIG. 8B). 5064 potentiates ANP and BNP-mediated NPRA activation only at submaximal concentrations of natriuretic peptides. No further increase in cGMP production is observed at saturating ligand levels. 5064 uniquely enhances the NPRA dependent cGMP response to natriuretic peptides. Other HuCAL® antibodies that are selected for their ability to bind to NPRA either have no effect on cGMP production or inhibit it (FIG. 10).

Example 6

Optimization of the anti-NPRA Binder 5064 Through Affinity Maturation

Altogether these data support the hypothesis that 5064 is able to bind and stabilize the activated NPRA receptor and thereby enhance the activity of natriuretic peptides. However, 5064 is the only binder, which shows this activity. Since this binder only has moderate affinity in the monovalent format (EC50 approx. 100 nM), the affinity of this binder is further optimized in order to potentially increase its biological activity.

A. Generation of Affinity Maturation Libraries

To increase the affinity and biological activity of the anti-NPRA 5064 Fab, L-CD R3 and HCDR2 regions are optimized in parallel by cassette mutagenesis using trinucleotide directed mutagenesis (Virnekäs et al, 1994), while the framework regions are kept constant. Prior to cloning for affinity maturation, the parental Fab fragment is transferred from the corresponding expression vector (pMORPH®x9_FH) into the CysDisplay™ vector pMORPH®25_LHC via XbaI/EcoRI. pMORPH®25_LHC is created from the HuCAL GOLD® display vector pMORPH®23_LHC by removal of one BssHII site interfering with library cloning for H-CDR2 optimization. For optimizing L-CDR3 the L-CDR3 and the constant region of the light chains of the parental Fab are removed by BbsI/SphI and replaced by a repertoire of diversified L-CDR3s together with the constant domain. In a second library the H-CDR2 (XhoI/BssHII) is diversified, while the connecting framework regions are kept constant. In order to monitor the cloning efficiency the parental H-CDR2 is replaced by a dummy, before the diversified H-CDR2 cassette is cloned in. Ligation mixtures of the two different libraries are electroporated in $E.\ coli$ TOP10F cells (Invitrogen, Carlsbad, Calif., USA) yielding from $5\times10$ to $8\times10^8$ independent colonies. This library size ensured coverage of the theoretical diversity. Amplification of the library is performed as described before (Rauchenberger et al., 2003). For quality control single clones are randomly picked and sequenced (SequiServe, Vaterstetten, Germany).

B. Whole Cell Panning Against NPRA-HEK Cells

The phage derived from the above maturation libraries (HCDR2 and LCDR3 maturation respectively) are individually subjected to 3 rounds of whole cell panning on NPRA-transected HEK-cells. Three different conditions are applied: Condition 1 is a whole cell panning in presence of ANP/BNP. Condition 2 is a whole cell panning in presence of ANP/BNP with competition by parental binder 5064. Condition 3 is a whole cell panning in absence of ANP/BNP. Thus 6 whole cell pannings are performed.

All steps are carried out at 4° C. After detachment with Accutase (PAA Laboratories, L11-007) cells are counted, harvested and adjusted to $5\times10^6$ cells per panning for the $1^{st}$ round. For the 2nd round $1\times10^6$ cells per panning are used and for 3rd round $5\times10^5$ cells per panning, The cells are resuspended in 1.5 ml of blocking buffer (PBS/5% FCS/0.05% NaN$_3$) and incubated for 30 min on a rotator. For panning conditions 1 and 2 ANP and BNP are added to a final concentration of 100 nM each in this incubation step. The cells are harvested by centrifugation (2 min, 2000 rpm) and resuspended carefully in the solution containing the pre-blocked phage. Before that step, 83.11 of phage (corresponding to $5.1\times10^{11}$ for HCDR2 matured library and $9.8\times10^{11}$ for LCDR3 matured library) per panning has been pre-blocked by mixing with 917 µl of blocking buffer and incubated for 2 h on a rotator. During the incubation of cells with pre-blocked phage ANP and BNP are added to a final concentration of 100 nM each for conditions 1 and 2.

For condition 2 the parental Fab 5064 is added to a final concentration of 200 nM, but only after cells and phage had already been incubated for 1.5 h. For all conditions the total time of incubation is 2 h. Then cells are harvested by centrifugation (2 min, 2000 rpm) and nonspecifically bound phage are washed off by incubation with 1.5 ml of blocking buffer on a rotator. The washing steps are performed as follows: 5×10 min in the 1st round, 5×20 min in the 2nd round and 6×20 min in the 3rd round. For condition 2 parental Fab 5064 is added to a final concentration of 200 nM in each washing step. Specifically bound phage are eluted from cells and subsequent steps are carried out as described above.

C. Panning Against NPRA-Fc Captured on Beads

Three different conditions are applied: Condition 1 and 2 are pannings in presence of 30 nM ANP and BNP each. Condition 3 is a panning in absence of ligands. The antigen concentration is varied depending on the panning condition by using a different amount of NPRA-Fc-coated beads or by using different dilutions of the NPRA-ECD-Fc containing cell supernatant. All plastic tubes used are pre-blocked by filling with 1.5 ml of PBS/5% BSA and incubating them overnight at 4° C. on a rotator.

The NPRA-Fc protein is captured on Dynabeads® (electromagnetic M-280 Streptavidin beads, 10 mg/ml, Dynal) via a biotinylated anti-Fe antibody (mouse anti-human Fc, Chemicon, #CBL102, biotinylated in PC-group). Between incubation steps the beads are washed with 1.5 ml of Bv buffer (PBS/0.05% BSA/0.02% Tween) and then harvested using a magnet.

The beads are prepared as follows: 60 µl of beads are mixed with 1437 µl of Bv-buffer and with 2.05 µl of biotinylated CBL102 and the mixture is incubated for 30 min at 22° C. on a rotator. The beads are washed, 1.5 ml of the NPRA-ECD-Fc containing cell supernatant is added and the mixture is incubated for 90 min at 22° C. on a rotator. Then the beads are washed again, resuspended in 1 ml of Bv buffer and then split into 2 fresh tubes, each containing 0.5 ml of the NPRA-Fc coated beads in suspension. In one tube ANP and BNP are added to a final concentration of 30 nM each and both tubes are incubated for 30 min at 22° C. on a rotator. Both samples are washed again in Bv buffer and resuspended in 0.75 ml of Bv buffer. Then the beads are ready to use. The beads are coated fresh for each round of the panning.

Simultaneously to coating the beads, 83 µl of phage (corresponding to $5.1\times10^{11}$ for HCDR2 matured library and $9.8\times10^{11}$ for LCDR3 matured library) per panning are pre-blocked by mixing with 5 µl of Ig Serum mouse (Mouse Gamma Globulin, Dianova, 015-000-002) and 712 µl of PBS/0.05% Tween/5% BSA and incubating for 2 h on a rotator.

The beads treated with ANP and BNP are used for panning condition 1 and 2. The beads without ligands are used for panning condition 3. For the 1st round 200 µl of the beads "ready to use" preparation are used.

For selection, 200 µl of beads (1st round) are mixed with 800 µl of blocked phage and incubated for 2 h on a rotator. The washing steps are as follows: 5× quick wash in PBS/0.05% Tween, 3×15 min in PBS/0.05% Tween on a rotator, 4× quick in PBS and 3×5 min in PBS on a rotator. After washing the beads are transferred into a fresh tube.

For elution, beads are harvested and resuspended in 300 µl of 20 mM DTT in 10 mM Tris/HCl, pH 8.0 and incubated for 10 min. Then the beads are harvested and the phage containing supernatant is used to infect $E.\ coli$ TG1 as described above.

In order to identify Fab clones with improved binding to cell-bound NPRA after affinity maturation, a modified FACS screening procedure is used: BEL extracts (whole cell lysates) of Fab-expressing bacterial clones are screened for specific cell binding via FACS. BEL extracts are diluted 1:50 in FACS buffer and used for FACS screening according to standard protocol. The dilution is chosen, because at that concentration binding of the parental Fab is barely detectable.

Clones displaying FACS signals significantly above values obtained for the parental controls are picked for further characterization.

D. Characterization of Affinity Matured Fabs

From both pannings on cells and NPRA-Fc protein more than one hundred hits are identified and 94 of these binders are micro-purified and further analyzed in cell binding and cGMP assays. Out of the 94 Fabs, 21 show superior performance in cell binding and/or the cGMP assay. Sequencing of these 21 binders reveals 14 unique clones, which are purified.

Three of the 14 Fabs are derived from the cell pannings and 11 are selected in pannings on NPRA-Fc. Nine Fabs are H-CDR2 matured and five Fabs are L-CDR3 optimized. All of them are derived from pannings done in presence of ANP.

Fourteen selected Fabs purified in mg-scale are analyzed in cell binding and cGMIP assays. The Fabs are tested at various concentrations for binding to HEK NPRA cells loaded with 100 nM ANP (FIG. 10A). In this study Fab 5504 displays the strongest binding followed by Fabs 5502, 5507, 5513, 5514 with slightly weaker affinities but still in the low nanomolar range. Interestingly, the five L-CDR3 matured Fabs show the strongest binding to human NPRA transfected cells, whereas the H-CDR2 matured Fabs in most cases display weaker binding.

Figure 11:
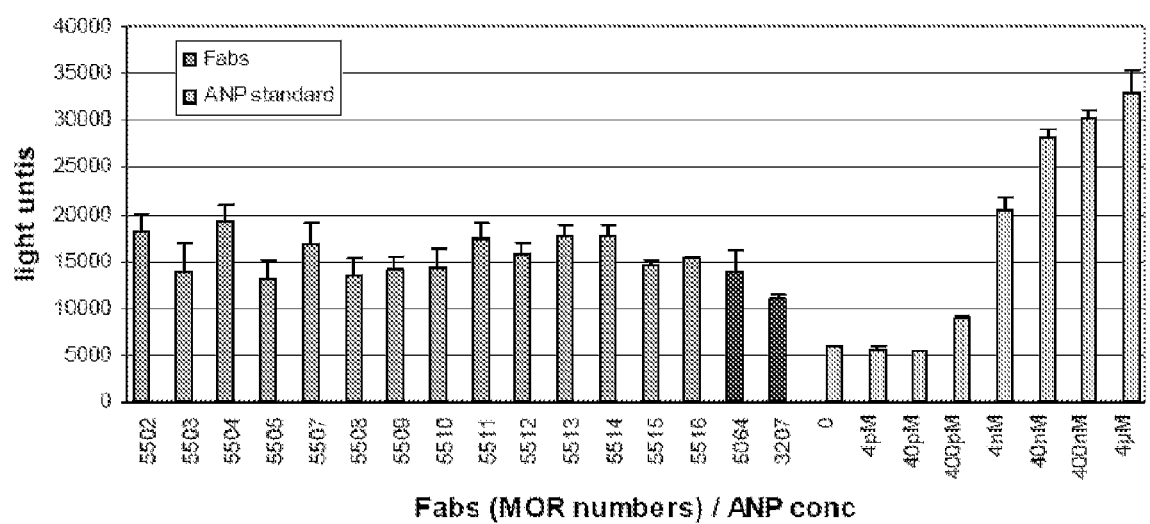
FIG. 11: Affinity matured Fabs enhance the cGMP response in HEK NPR A cells to suboptimal levels of ANP. HEK NPRA cells are incubated with 400 nM Fabs and 400 pM ANP. cGMP is quantitated as described.

The potentiating activity of the Fabs is assessed by measuring cGMP production in HEK NPRA cells in the presence of a suboptimal concentration (400 pM) of ANP (FIG. 11). This ligand concentration is sufficient to induce a significant but not a full cGMP response on its own. As compared to the negative control Fab 3207, the parental Fab 5064 displays a slightly increased cGMP signal. At least some of the matured Fabs (5502, 5504, 5507, 5511, 5513, 5514) appear to induce higher cGMP levels than 5064 under these experimental conditions. Based on cell binding data and the analysis of the cGMP response the L-CDR3 matured Fabs 5502, 5504, 5507, 5513, 5514 and the H-CDR2 matured Fab 5511 are analyzed in more detail.

Figure 12A:
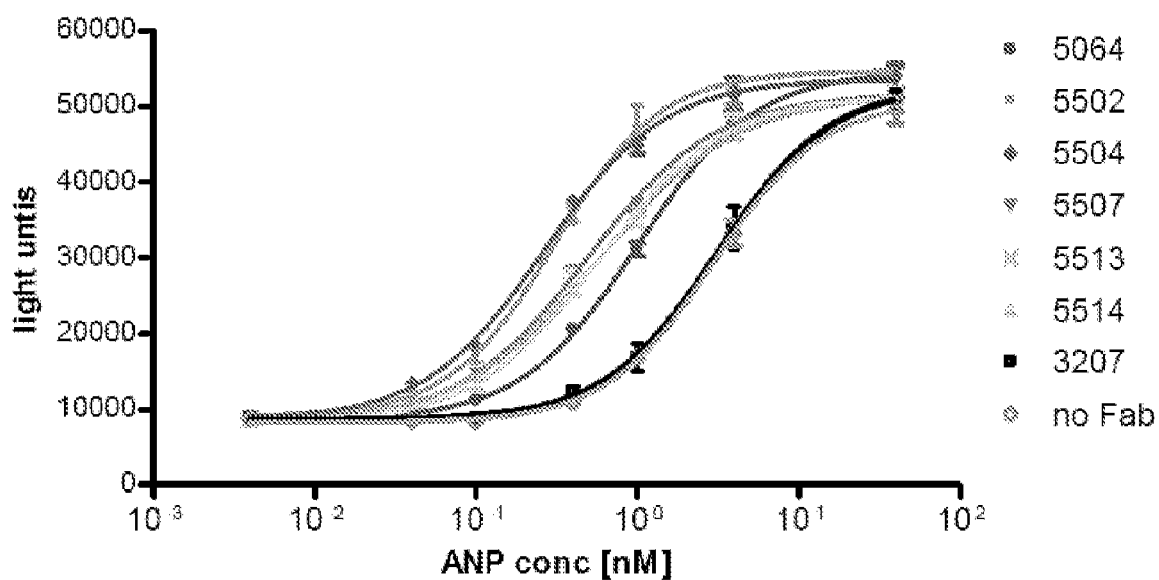
FIG. 12A and FIG. 12B: Affinity matured Fabs enhance the NPRA mediated cGMP response to both ANP and BNP. HEK NPRA cells are incubated with 400 nM Fabs and increasing concentrations of ANP (FIG. 12A) or BNP (FIG. 12B). cGM NP is quantitated as described.
Figure 12B:
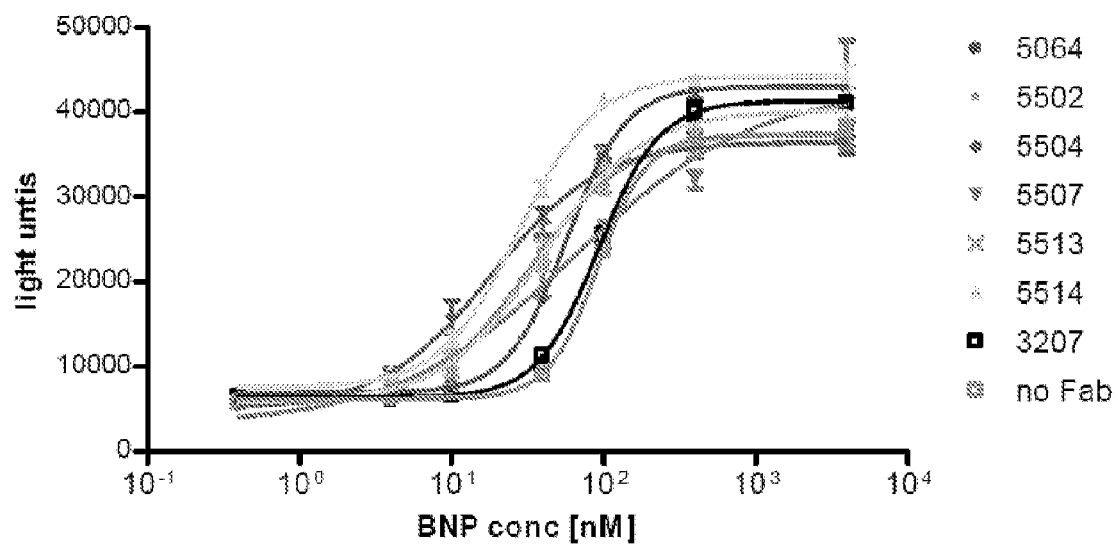

In this study increasing concentrations of ANP is added to HEK NPRA cells in the presence of 400 nM of the selected Fabs and cGMP production is monitored (FIG. 12A). As seen previously the parental Fab 5064 decreases the EC50 of ANP from 3 nM (in presence of negative control Fab) to 1 nM. Two of the matured Fabs, 5502 and 5504, are able to shift the EC50 of ANP further down to 0.3 nM and thus enhance the potency of ANP by a factor of 10. Three other matured Fabs, 5507, 5513, 5514, display intermediate activities resulting in EC50 values of 0.5-0.6 nM for ANP. The impact of the Fabs on the dose-response of BNP is also analyzed. Although the effect is less pronounced as for ANP, the matured Fabs clearly enhance the potency of BNP. While the parental Fab decreases the EC50 of BNP only 2-fold, the matured Fabs show a 5-fold decrease down to 18 nM for Fab 5504 compared with an EC50 of 90 nM in presence of negative control Fab (FIG. 12B).

Altogether, the data provide evidence that affinity maturation of 5064 results in elevated binding of the resulting Fabs to the NPRA-ligand complex as well as in increased potentiation of ANP and BNP dependent cGMP production in NPRA overexpressing cells.

The binders 5502, 5503, 5504, 5507, 5508, 5511, 5513, 5514 are converted into the IgG4-Pro format. The IgG4 subtype is chosen to minimize effector function of the resulting antibodies and the proline 228 to serine mutation is introduced to abrogate Fab arm exchange (van der Neut Kolfschoten, et al *Science* 317:1554, 2007). The most promising candidates are those that have alterations in the light chain (5502, 5504, 5507, 5513, 5514). The light chains of these IgGs are cross combined with the heavy chain of matured IgG 5511, because the 5511 Fab had shown some increased activity compared to the parental 5064 in cGMP assay (FIG. 11).

Figure 13A:
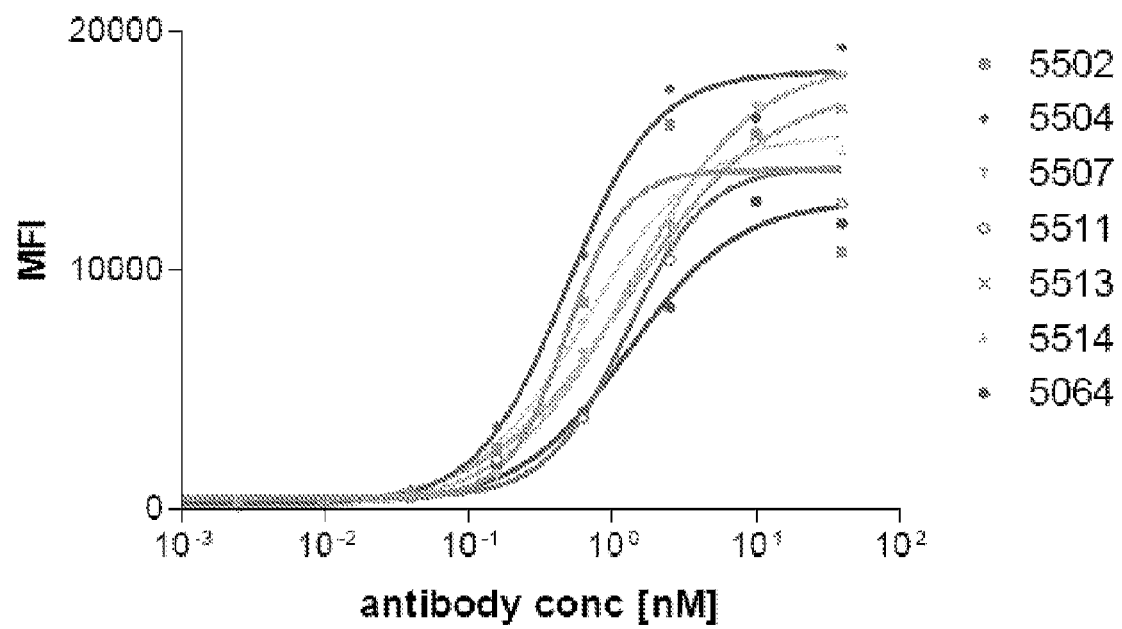
FIG. 13A and FIG. 13B: Affinity matured (FIG. 13A) and cross combined (FIG. 13B) IgG4_Pro antibodies bind to ANP loaded NPRA with better affinity than the parental antibody 5064. HEK NPRA cells are incubated with 100 nM A NP and increasing concentrations of antibodies and binding is determined by FACS. MFI—mean fluorescent intensity
Figure 13B:
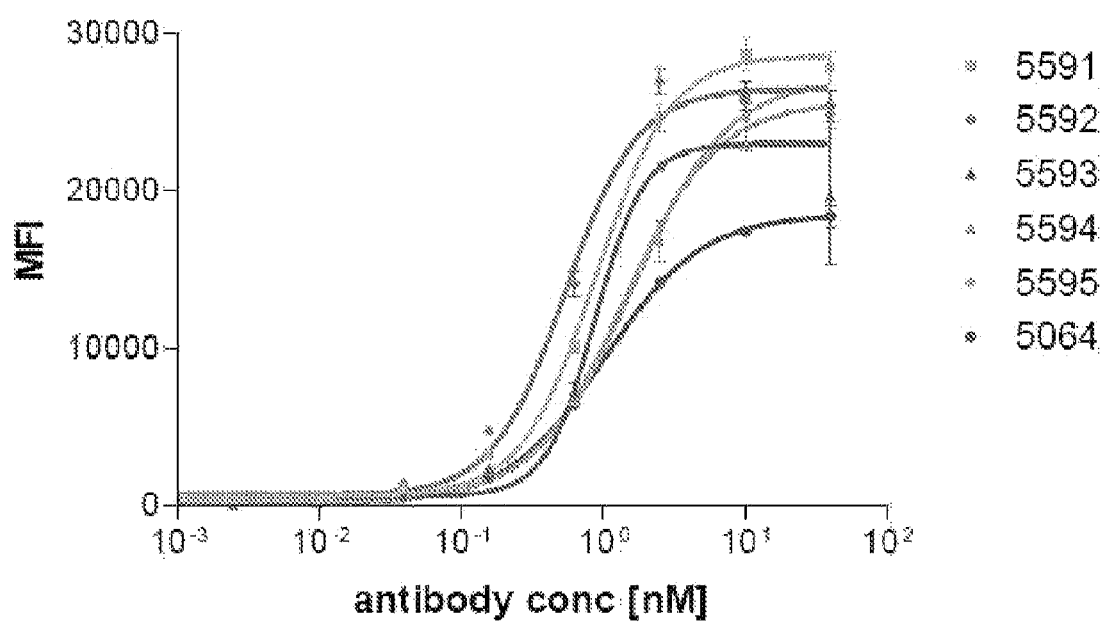
Figure 14A:
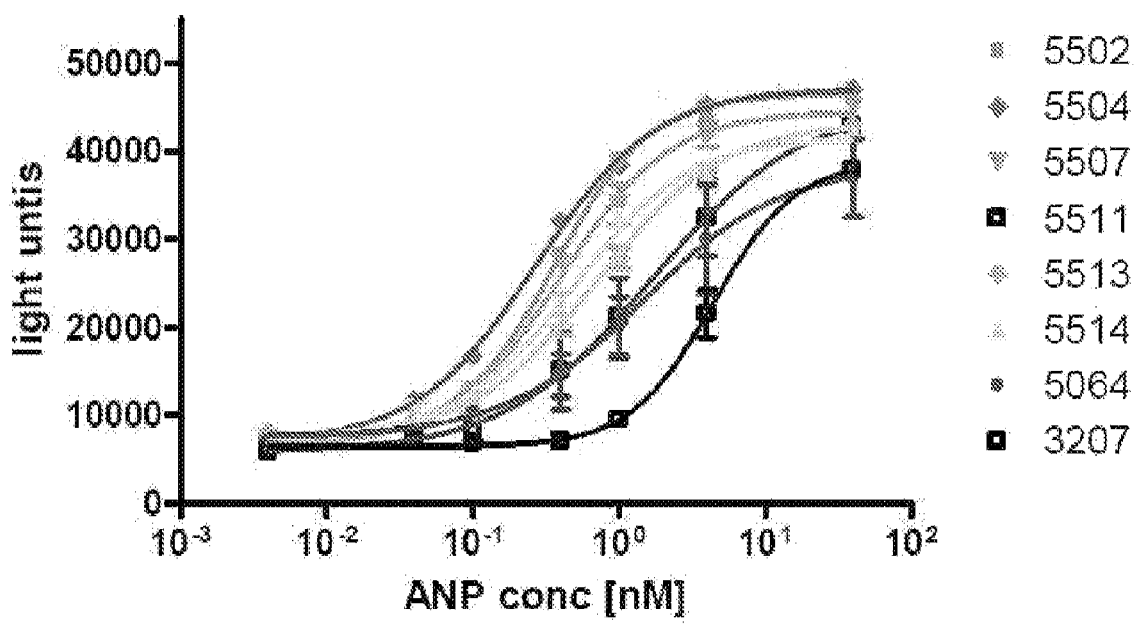
FIG. 14A and FIG. 14B: Affinity matured (FIG. 14A) and cross combined (FIG. 14B) IgG4_Pro antibodies enhance the NPRA mediated cGMP response to ANP. HEK NPRA cells are incubated with 200 nM antibody and increasing concentrations of ANP. cGMP is quantitated as described. 5064 is the parental antibody and 3207 is a control antibody.
Figure 14B:
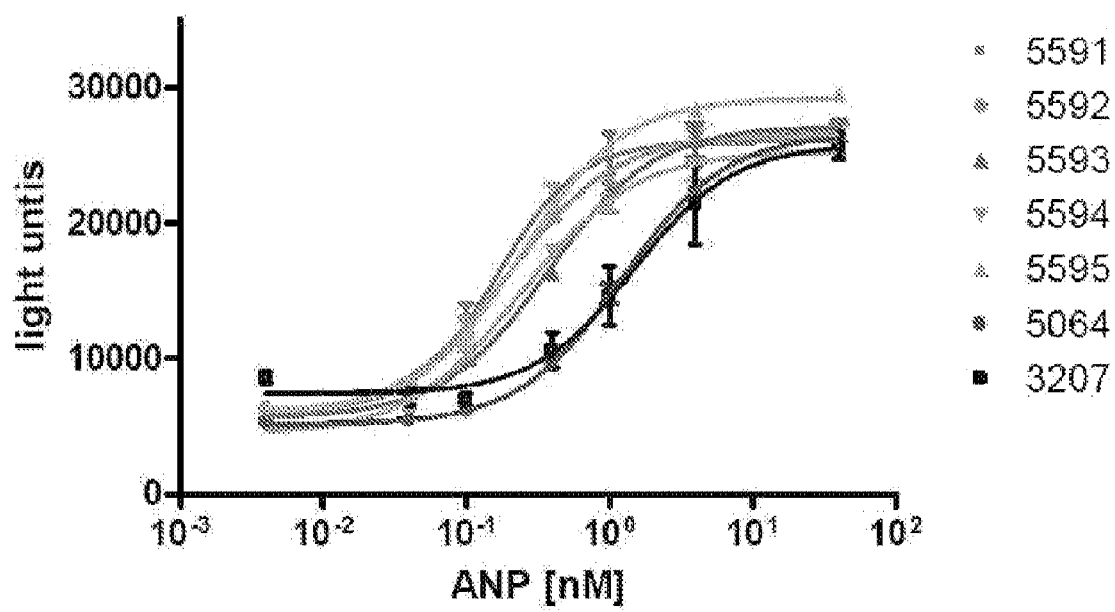
Figure 15A:
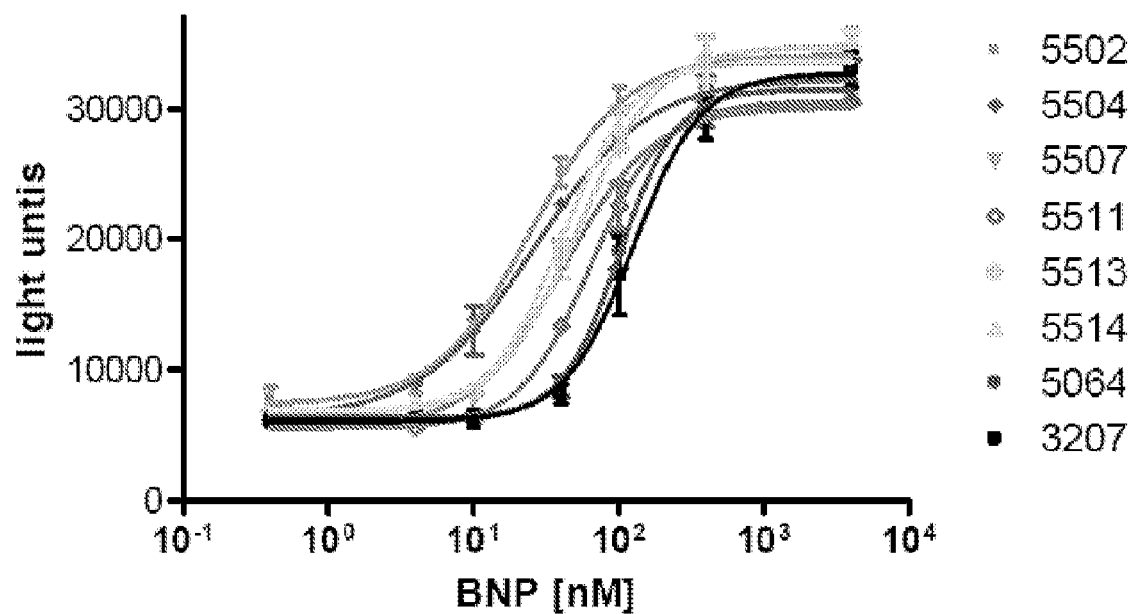
FIGS. 15A and 15B: Affinity matured (FIG. 15A) and cross combined (FIG. 15B) IgG4_Pro antibodies enhance the NPRA mediated cGMP response to BNP. HEK NPRA cells are incubated with 200 nM antibody and increasing concentrations of BNP. cGMP is quantitated as described. 5064 is the parental antibody and 3207 is a control antibody.
Figure 15B:
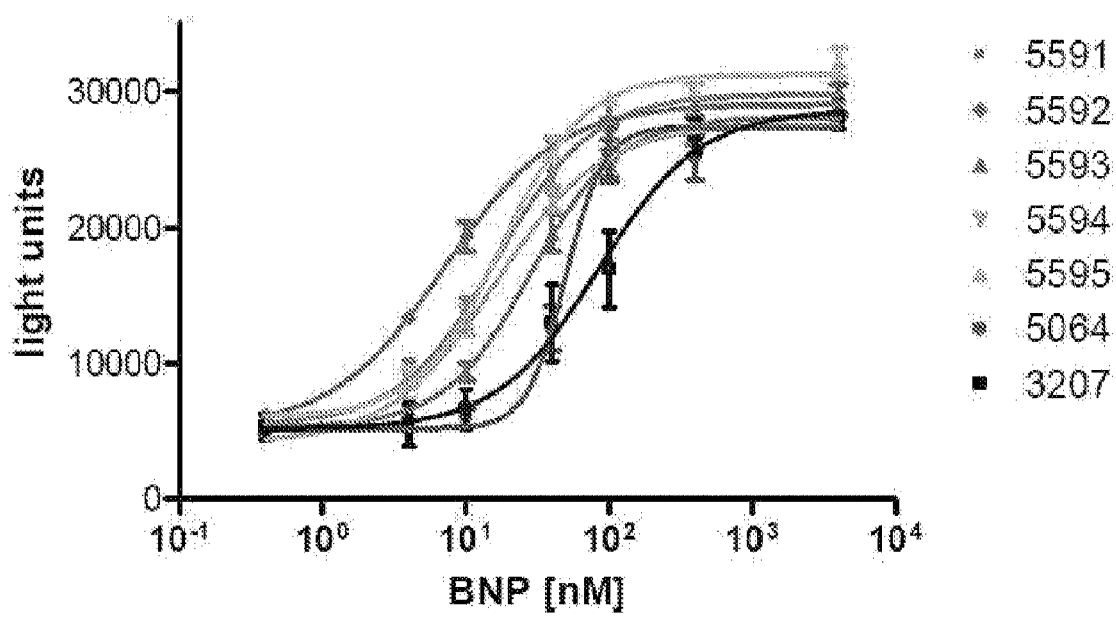

The affinity matured and cross combined IgG4_Pro antibodies are analyzed at various concentrations by FACS for binding to HEK_NPRA loaded with 100 nM ANP (FIG. 13A and FIG. 13B). While the parental IgG4_Pro 5064 shows half-maximnal binding at a concentration of 1.6 nM, the matured antibodies displayed increased binding with EC50 values down to 0.5 mM, most likely at the sensitivity limit of the assay.

The selected IgG4_Pro antibodies are also analyzed for their capacity to increase the potency of ANP and BNP in the cGMP assay. A fixed concentration of 200 nM of antibody is applied with various concentrations of ANP or BNP to HEK NPRA cells. FIGS. 14A and 14B and 15A and 15B show representative cGMP assays, The matured antibodies further potentiate ANP and BNP dependent cGMP production as compared to the parental antibody 5064. 5502, 5504, 5591 and 5592 induce the largest shift with up to a 10-fold increase in the potency of ANP.

Figure 16A:
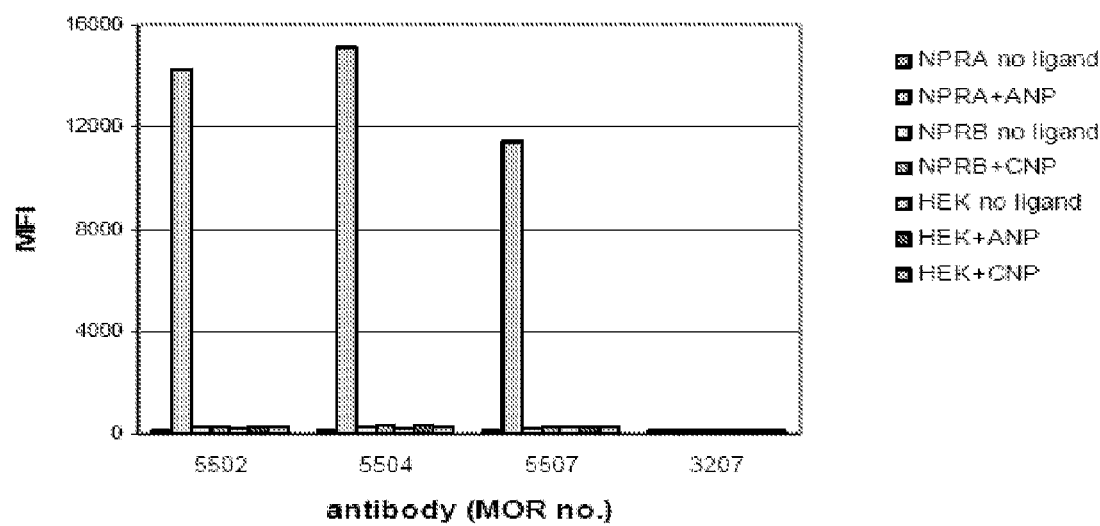
FIG. 16A and FIG. 16B: Affinity matured (FIG. 16A) and cross combined (FIG. 161B) IgG_Pro antibodies do not cross react with NPRB. HEK NPRA cells +/−100 nM ANP, HEK NPRB cells +/−100 nM CNP and non-transfected HEK cells +/−100 nM ANP or CNP are incubated with 20 nM of antibody and binding is assessed by FACS. 3207 is included as a negative control antibody. MFI—mean fluorescent intensity
Figure 16B:
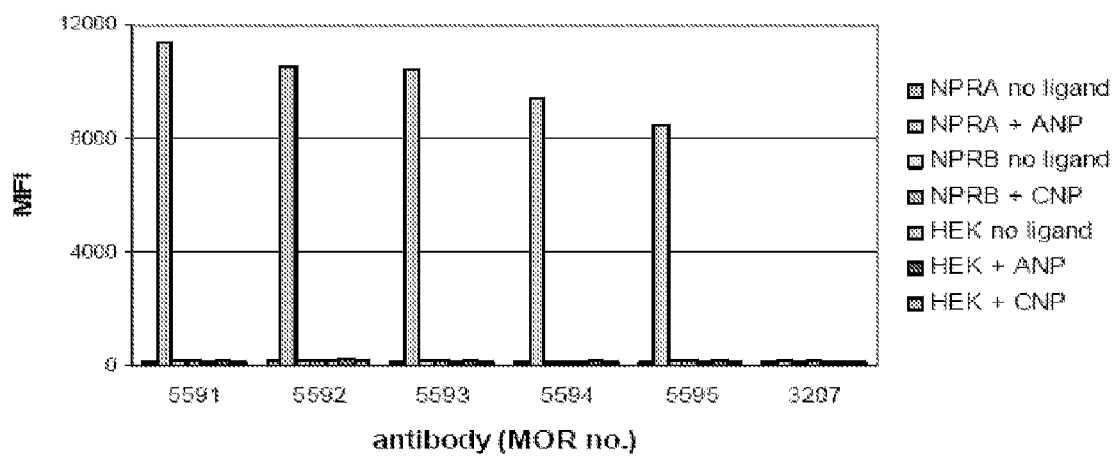
Figure 17:
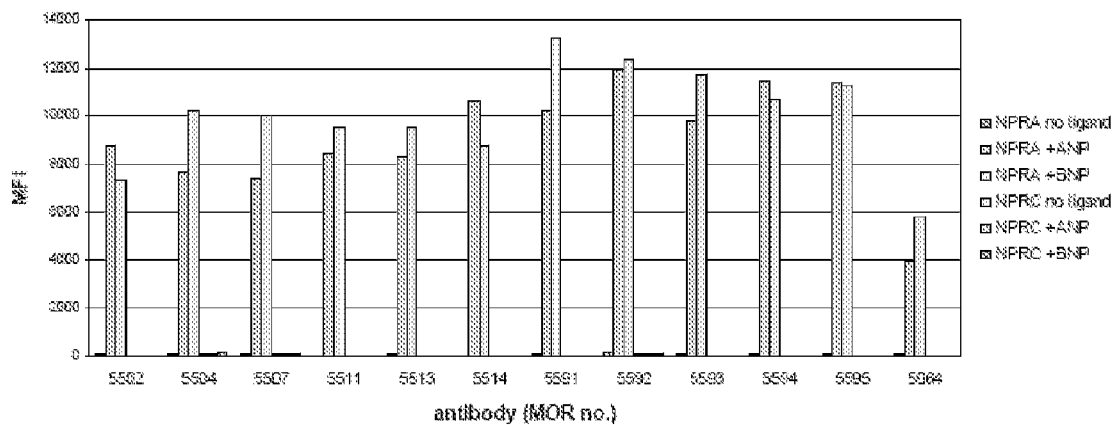
FIG. 17: Affinity matured and cross combined IgG_Pro antibodies do not cross react with NPRC. HEK NPRA cells +/−100 nM ANP or BNP or HEK NPRC cells +/−100 nM ANP or BNP are incubated with 20 nM of antibody and binding is assessed by FACS. 5064 is the parental antibody.

To determine whether the profiled antibodies are selective for NPRA, binding to the related natriuretic peptide receptors NPRB and NPRC is assessed by FACS. While the matured (FIG. 16A) and cross combined (FIG. 16B) antibodies bind to HEK NPRA cells incubated with ANP, no binding is observed to HEK NPRB cells in the presence or absence of its ligand CNP. Similarly no binding is seen to HEK NPRC cells in the presence or absence of ANP or BNP (FIG. 17).

Example 7

Determination of Antibody Binding Affinity to NPRA-Natriuretic Peptide Complexes A. Binding Affinity Determination by Quantitative FACS Analysis The binding affinity of selected antibodies to NPRA complexed to it peptide ligands is quantitated utilizing several different technologies. In one assay, the binding to HEK NPRA cells in the presence of 100 nM ANP is evaluated by FACS analysis as outlined above. The parental IgG4_Pro 5064 shows half-maximal binding at a concentration of 1.6 nM while the matured and cross combined antibodies display increased binding with $EC_{50}$ values in the nM range. However these values are thought to be at the limits of this assay.

TABLE 1

FACS analysis of the binding of IgG4_Pro antibodies to HEK NPRA cells in the presence of 100 nM ANP

| Antibody IgG4_Pro | $EC_{50}$ (nM) |
|---|---|
| 5064 | 1.08 ± 0.13 |
| 5502 | 0.68 ± 0.26 |
| 5504 | 0.56 ± 0.15 |
| 5591 | 0.73 ± 0.19 |
| 5592 | 0.52 ± 0.04 |

B. Binding Affinity Determination by Surface Plasmon Resonance (Biacore)

In another assay, the purified human NPRA-Fc fusion protein construct is used to develop a surface plasmon resonance (BIAcore) assay for determining affinity and kinetic constants for the antibodies. NPRA-Fc in 10 mM sodium acetate buffer, pH 5.5 is immobilized on a CM5 chip in a Biacore 3000 instrument (GE Healthcare, Biacore, Inc.) through amine coupling at a density of 1000 RU. Increasing concentrations of anti-NPRA antibodies ranging from 0.5 to 7 nM in 10 mM HEPES, pH 7.4, 150 mM NaCl supplemented with 100 nM human ANP, BNP or urodilatin is injected in the flow cell at a flow rate of 20 μl/min for 10 minutes followed by a 15 minute dissociation period. The collected association and dissociation data from each experiment is globally fitted with the association ($k_a$) and dissociation ($k_d$) rates fit simultaneously. Summarized in the tables below, the kinetic binding data demonstrate that the interactions are of high affinity, in the range of 10 pM~200 pM and that the antibodies bind to NPRA in the presence of all three of its natural ligands. The candidates have higher affinity in the presence of ANP than in the presence of BNP and urodilatin. Anti-NPRA 5592 has higher affinity than 5502 and 5592 in the presence of ANP, BNP or urodilatin. The data fit to a 1:1 binding model which suggests that one bivalent antibody binds to a single dimeric NPRA extracellular domain. 5591 and 5592 Fabs bind to NPRA-Fc in the presence of ANP with lower affinity and also with a 1:1 stoichiometry.

TABLE 2A

Affinity and kinetic data of surface plasmon resonance analysis of interaction between Fabs or IgGs with NPRA-Fc in the presence of ANP

| Fabs or IgGs | $K_D$ (pM) | $k_a$ (1/Ms) | $k_d$ (1/s) |
|---|---|---|---|
| 5591 Fab | 1160 | 8.84e5 | 1.03e−3 |
| 5592 Fab | 426 | 8.68e5 | 3.69e−4 |
| 5502 IgG | 172 | 1.65e6 | 2.83e−4 |
| 5591 IgG | 27.5 | 3.88e6 | 1.07e−4 |
| 5592 IgG | 11.0 | 9.59e6 | 1.06e−4 |

TABLE 2B

Affinity and kinetic data of surface plasmon resonance analysis of interaction between IgGs and NPRA-Fc in the presence of BNP

| IgGs | $K_D$ (pM) | $k_a$ (1/Ms) | $k_d$ (1/s) |
|---|---|---|---|
| 5502 | 413 | 1.36e6 | 5.63e−4 |
| 5591 | 380 | 2.69e6 | 1.02e−3 |
| 5592 | 45.9 | 7.42e6 | 3.40e−4 |

TABLE 2C

Affinity and kinetic data of surface plasmon resonance analysis of interaction between IgGs and NPRA-Fc in the presence of urodilatin

| IgGs | $K_D$ (pM) | $k_a$ (1/Ms) | $k_d$ (1/s) |
|---|---|---|---|
| 5502 | 211 | 2.12e6 | 4.48e−4 |
| 5591 | 92.8 | 2.56e6 | 2.38e−4 |
| 5592 | 25.1 | 3.96e6 | 9.94e−5 |

C. Binding affinity Determination by KinExA

Figure 18:
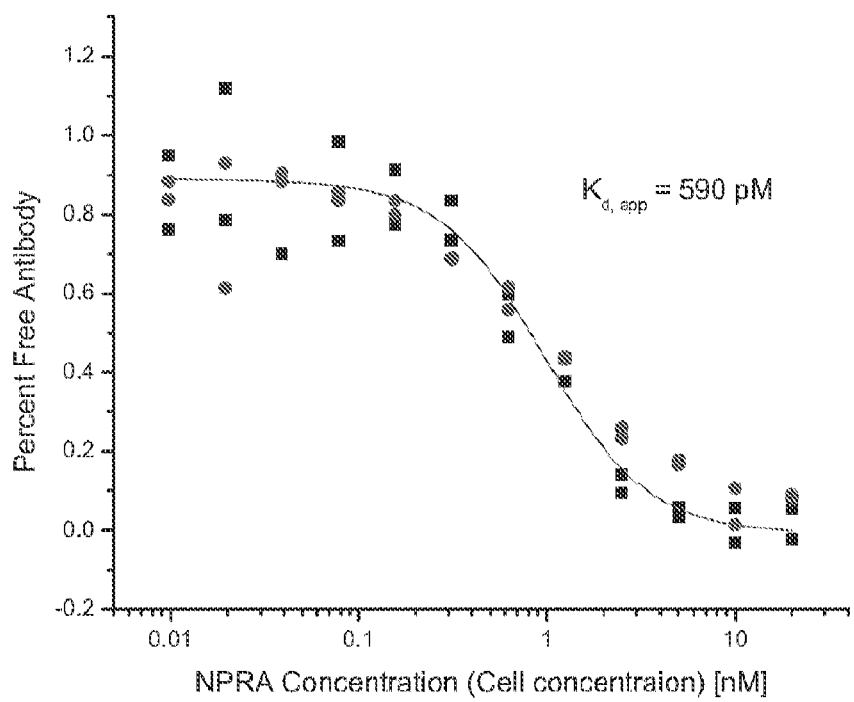
FIG. 18. KinExA binding curve used for calculating the apparent $K_d$ of 5591 IgG binding to HEK NPRA cells. 75 pM (black, square) and 200 pM (red, circle) 5591 IgG FIG. 19. 5591 Potentiates NPRA-mediated cGMP Responses over time in HEK NPRA Cells. HEK NPRA cells are incubated with 0, 200 pM or 1 µM ANP in the absence or presence of 10 µg/ml 5591 IgG and cGMP levels are quantitated up to 120 minutes.

To confirm the anti-NPRA antibody affinity to cell-associated full length NPRA, a whole cell binding assay is done employing the KinExA technology. HEK NPRA cells ranging in concentration from $2 \times 10^7$ cells/ml to $9.7 \times 10^3$ cells/ml in cold Hank's Balanced Salt Solution with 0.5% bovine serum albumin are incubated in the presence of 1 nM ANP and either 75 or 200 pM 5591 IgG for 1 hour at 4° C. The cells are pelleted and the supernatants are loaded into the KinExA instrument (Sapidyne Instruments) where free IgG is captured on beads using mouse anti-human kappa light chain (Southern Biotech) and quantitated using goat anti-human IgG couple with Alexa Fluor 647 (Invitrogen). Using this methodology, the apparent Kd for 5591 antibody binding is determined to be 590 pM (FIG. 18). This value is about 20-fold higher that the $K_d$ obtained though surface plasmon resonance binding to the NPRA extracellular domain-Fc fusion protein.

Example 8

Antibody Potentiation of NPRA Mediated cGMP Responses

The binding of peptide ligand to NPRA results in the activation of the guanylyl cyclase activity associated with this receptor. The effects of the antibodies on the production of cGMP in response to ligand are measured in HEK NPRA cells in suspension. The cells are incubated for 15 minutes in the presence of 10 μg/ml of the NPRA specific IgG_Pro antibodies or the control 3207 antibody, and increasing concentrations of ANP or BNP. cGMP levels are quantitated using a competitive immunoassay with a luminescent readout (HitHunter kit, DiscoverX, Fremont, Calif.)). cGMP production dose response curves are generated with a four parameter logistic equation fitted using the Levenburg Marquardt algorithm in XLfit 4.2 data analysis software (ID Business Solutions, Ltd., Guildford, UK) and $EC_{50}$ s are calculated. Fold shifts in an $EC_{50}$ represents the ratio between the EC50 generated in the presence of an anti-NPRA antibody and that generated in the presence of an equal concentration of the control antibody 3207.

5502, 5591 and 5592 reproducibly shift the ANP or BNP dose response curves to the left as illustrated in FIGS. 14 and 15. The magnitude of the shifts are enumerated in Table 3 and range from a maximum of 7-fold for ANP to 44-fold for BNP. The ranges are reflective of individual experiments with at least 3 experiments done under each condition. The increased fold shifts observed in the presence of the antibodies upon activation of NPRA with BNP presumably results from the weaker affinity of this NPR A peptide ligand.

TABLE 3

Potentiation of Antibody mediated cGMP responses in ANP or BNP treated HEK NPRA cells

| IgGs | Shift in ANP $EC_{50}$ | Shift in BNP $EC_{50}$ |
|---|---|---|
| 5502 | 5-7 fold | 15-19 fold |
| 5591 | 3-6 fold | 15-16 fold |
| 5592 | 3-5 fold | 31-44 fold |

The effects of the antibodies are most notable at the sub-optimal levels of natriuretic peptide which, being in the low pM range, are consistent with the concentrations of ANP and BNP observed in patients with heart failure. Shifts of similar magnitude are seen in ANP treated HeLa cells which express NPRA endogenously.

In order to measure the biological potency of the antibodies, these reagents are incubated with H-IEK NPRA cells in the presence of a sub-optimal concentration of ANP (200 pm) and cGMP production is monitored. The antibodies are dose responsive with $EC_{50}$ values around 1 nM and about 10 fold more potent than the parental antibody 5064 (Table 4).

TABLE 4

Titration of the anti-NPRA antibodies on HEK NPRA cells in the presence of 200 pM ANP

| IgGs | cGMP $EC_{50}$ (nM) |
|---|---|
| 5064 | 12.1 |
| 5502 | 2.1 |
| 5504 | 1.2 |
| 5591 | 0.5 |
| 5592 | 1.0 |

Example 9

Prolongation of NPRA-Mediated cGMP Responses by 5591

Figure 19:
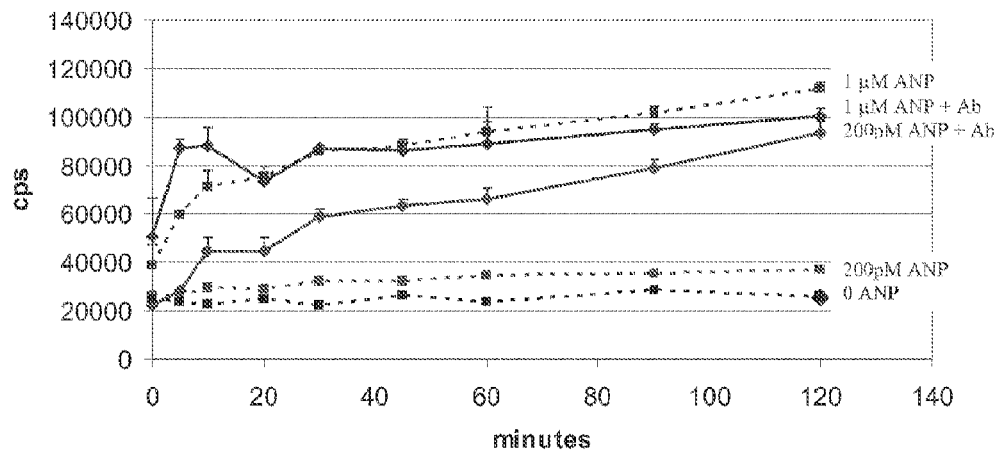

In addition to enhancing activation of the receptor at low ligand concentrations, the anti-NPRA antibodies also appear to extend the timeframe of receptor signaling. This is demonstrated by monitoring the kinetics of NPRA-dependent cGMP production in HEK NPRA cells (FIG. 19). The cells are incubated with either a sub-optimal (200 pM) or an excess (1 µM) concentration of ANP in the absence or presence of 10 µg/ml 5591 and cGMP production is measured over time as detailed above.

At sub-optimal levels of ANP, 5591 progressively enhances cGMP production over the 2 hour time frame of this experiment. In the presence of a high concentration of ANP, where it would be predicted that the receptor would already be maximally activated, the antibody has no effect.

Example 10

Antibody Binding Stabilizes the Receptor Ligand Complex

In order to directly monitor the effects of the antibodies on the interaction of a natriuretic peptide with its receptor, the binding of radiolabeled ANP to HEK NPRA cells is examined. 100 µl of HEK NPRA cells at $2\times10^6$ cells/ml in DMEM (Invitrogen-Gibco) with 0.1% bovine serum albumin (Sigma-Aldrich) are added to each well of Multiscreen HTS FC 1.2 mm G1 96 well plates (Millipore Corporation, Billerica, Mass.) coated with 0.2% polyethylenimine (Sigma-Aldrich). 5502, 5504, the parental antibody 5064 or the control antibody 3207 is added at a final concentration of 10 µg/ml. 100 µl/well of various concentrations of $^{125}$I ANP (GE Healthcare Bio-Sciences, Piscataway, N.J.) is then added to the appropriate wells and the plates are incubated at room temperature on an orbital shaker for two hours. The cells are washed four times with 200 µl/well of cold DMEM with 0.1% BSA using a vacuum manifold, followed by a single wash with PBS supplemented with 25 mM HEPES, and 0.1% BSA. The plates are air dried overnight, the bottom each plate is sealed with an opaque white plate sealer, and 30 µL of Microscint 40 is added to each well. The top of the plates are sealed with TopCount Plate Sealers and they are read in a TopCount microplate scintillation counter (Perkin Elmer). Non-specific binding is assessed by incubating the cells with $^{125}$I ANP in the presence of a 200 fold excess of cold ANP.

Figure 20:
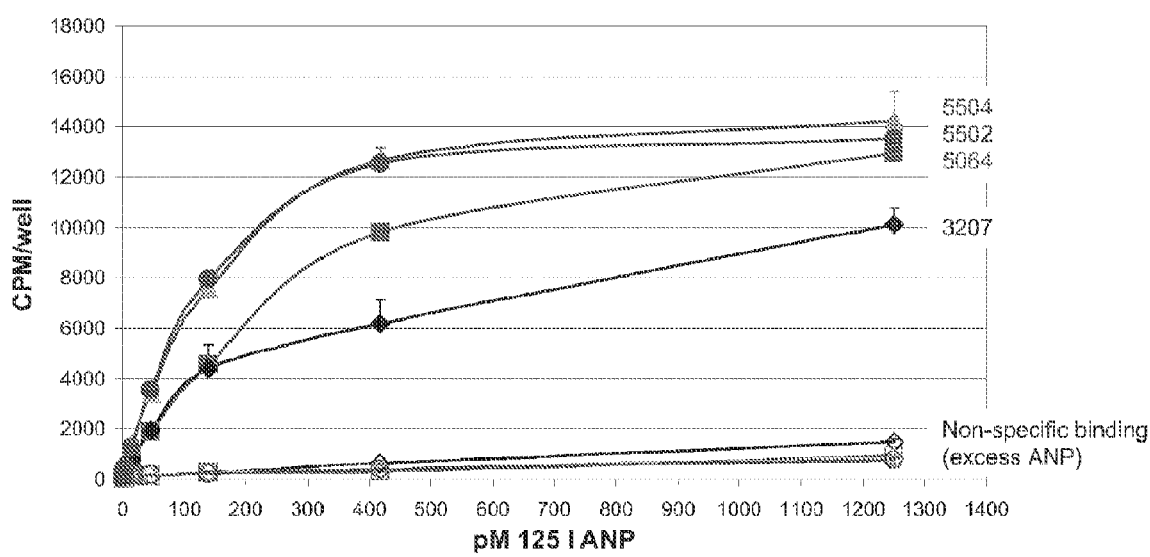
FIG. 20. 5502, 5504 and 5064 enhance the binding of $^{125}I$ ANP to HEK NPRA cells as compared to the control antibody 3207. HEK NPRA cells are incubated with increasing concentrations of $^{125}I$ ANP in the presence of anti-NPRA or control antibodies and cell associated radioactivity is quantitated. Non-specific binding in determined by adding an excess of cold ANP. CPM/well=counts per minute/well FIG. 21. 5502, 5504, 5591, 5592 and 5064 slow the off-rate of $^{125}I$ ANP from HEK NPRA cells. HEK NPRA cells are incubated in the presence of anti-NPRA or control antibodies and 100 nM $^{125}I$ ANP. Excess cold ANP is then added and the cells associated radioactivity is quantitated over time. The points to the left of the zero timepoint reflect cell associated radioactivity prior to the addition of cold ANP. CIPM=counts per minute
Figure 21:
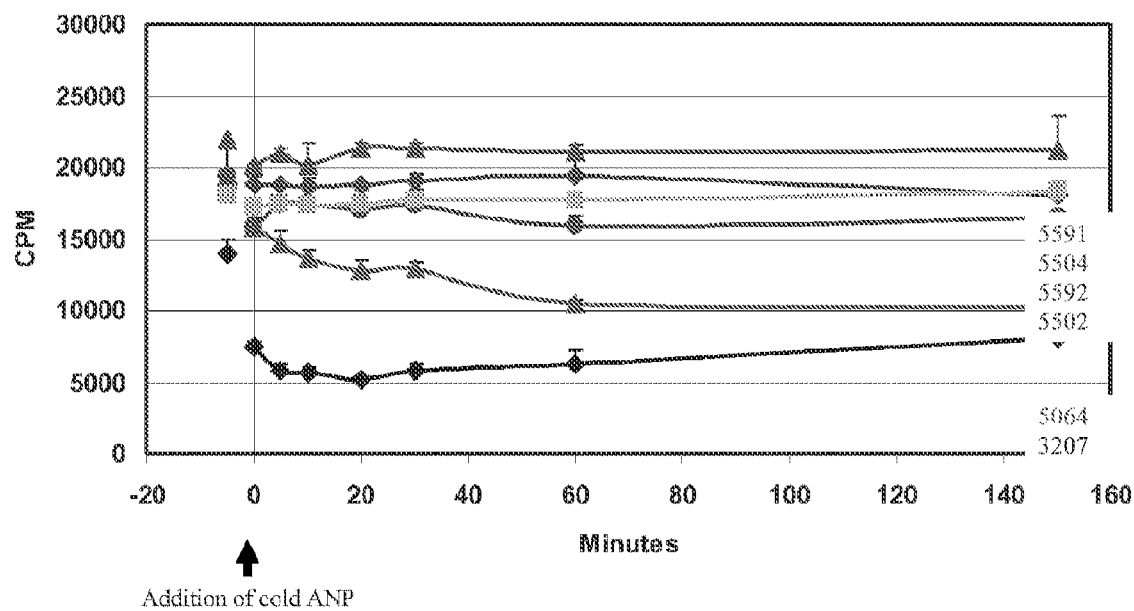
Figure 22:
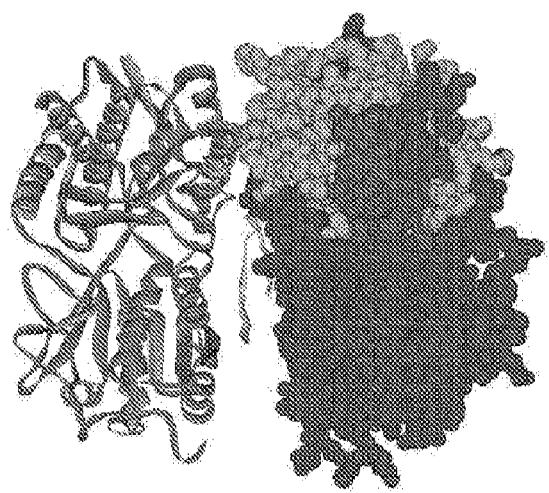
FIG. 22: Mapping of peptides from the extracellular domain of NPRA showing changes in deterium exchange rates upon 5591 binding. Areas shaded in pink represent strong protection from exchange and areas shaded in red very strong protection. The areas shaded in red are represented by an epitope that comprises residues 7-28 (NLTVAVVL-PLANTSYPWSWARV) (SEQ ID NO:30), 121-129 (VKDEYALTT) (SEQ ID NO:31), 313-320 (TMEDGLVN) (SEQ ID NO:32), 327-333 (HDGLLLY) (SEQ ID NO:33) and 347-351 (VTDGE) (SEQ ID NO:34) located in the three dimensional structure of NPRA when NPRA is bound to ANP and/or BNP and the areas shaded in pink represent epitopes that have peptide sequences

Initial studies reveal that this class of antibodies significantly enhanced the binding of $^{125}$I-ANP to HEK NPRA cells as compared to the control antibody 3207 (FIG. 20). The enhanced binding is evident even at concentrations of ANP below 200 pM (within the range of ANP levels observed in heart failure patients). One possible explanation for the observed increased $^{125}$I-ANP binding seen is that the antibodies slow the release of ANP from the receptor. In order to test this hypothesis, $1\times10^6$ HEK NPRA cells/ml are incubated with 100 nM $^{125}$I-ANP in the presence of 10 µg/ml anti-NPRA or control antibody for 2 hours at 4° C. to form complexes. A 2000 fold excess of cold ANP is then added, and 100 µl samples are transferred to wells in a filter plate over time and cell associated radioactivity is quantitated as outlined above. In the presence of the control antibody 3207 the off-rate of ANP is so rapid that it is difficult to capture even at the zero time point (FIG. 21). However 5502, 5504, 5591 and 5592, significantly slow the release of ANP from the receptor. The parental antibody 5064 is less effective than the matured and cross-combined antibodies. These data are consistent with a model in which the antibody binds to and stabilizes the ligand-bound confirmation of the NPRA and sustains and enhances signaling though this receptor.

Example 11

Epitope Mapping by Hydrogen/Deuterium Mass Spectrometry (HXMS)

In order to identify the antibody binding site on the extracellular domain of NPRA the technique of hydrogen/deuterium mass spectrometry is utilized. This method is employed to study the solvent accessibility of the backbone amide hydrogens in a polypeptide and changes that occur upon antibody binding, It involves the exposure of NPRA-Fc, NPRA-Fc+ANP or NPRA-Fc+ANP+5591 IgG4_Pro to heavy water for various lengths of time. The hydrogen/deuterium exchange is quenched by low pH and temperature and the protein complexes are rapidly degraded by pepsin and then analyzed by LC/MS to determine the extent of deuterium incorporation into each peptide.

A. Deuterium Exchange Experiments-Identification of Peptides.

Peptides generated from NPRA-Fc by peptic digestion are identified. The protein is digested with pepsin, on ice, for 5 minutes at 0° C. The resulting peptides are subjected to pHPLC/FTMS analysis. Mobile phase A (99/1/0.1, $H_2O$/Acetonitrile/Formic Acid) and Mobile Phase B (95/5/0.1, $H_2O$/Acetonitrile/Formic Acid), Flow rate is 100 µl min, with a 10 µl injection onto a 150×1 mm HypersilC18 column. (Thermo PN 22105-396). The gradient program is from 0% B to 100% B at 15 minutes, hold to 19 minutes. FTMS spectra (Bruker Apex II, Billerica, Mass.) are acquired from m/z 400-1800. Four 0.35 sec spectra are accumulated for each stored spectrum with a 256 K length, 50,000 resolution. External calibration is performed by in source fragmentation of porcine renin substrate. A second run is made under identical conditions with the exception of increasing the capillary exit voltage of the interface from 80 V to 180 V to produce fragment ions from the eluting peptides and alteration of the m/z range to 200-2000 and using 512K word acquisition. Data are converted to MassLynx (Micromass/Waters, Manchester, U K) format for analysis. All spectra are averaged into a single spectrum. This is subjected to analysis by MassLynx Max-ENT3 to produce a list of monoisotopic molecular weights for each deconvoluted component. This list is searched versus the protein sequence to determine possible peptides without any constraints on the cleavage sites with the use of a 5 ppm error window. The corresponding spectrum is extracted from the high capillary exit voltage run. The fragment ions present in the spectrum are used for comparison to theoretical fragmentation patterns generated by the MassLynx software.

B. Hydrogen/Deuterium Exchange Experiments

NPRA-Fc, NPRA-Fc+ANP or NPRA-Fc, +ANP+5591-IgG complexes are diluted 1:10 into deuterated 5 mM NaH$_2$PO$_4$ buffer at pH 7.0 and allowed to exchange for varying lengths of time (5, 15, 45, 100, 1000 seconds) at room temperature. Exchange is quenched by lowering the pH and temperature (adding an equal volume of ice-cold 100 mM NaH$_2$PO$_4$, pH 2.5). The protein is then digested with pepsin (1:1 for 5 minutes on ice) and injected onto a trap column (Michrom C18) and then a 0.8×150 mm C18 (PepMap C18, LC Packings) column for separation by µHPLC. The flow rate is 30 µl/min with the injector, sample loop, column and transfer lines placed in an ice bath.

A Bruker Apex II FTMS with ESI is employed for on line monitoring of the chromatographic effluent. A 1.1 sec hexapole accumulation is performed before ion injection, excitation and detection (m/z 350-2000). Two 256 k spectra, are averaged for each stored spectrum, 128 averaged spectra are acquired per run. Resolution is 55,000 FWlHM. An external calibration with in-source fragment ions of porcine renin substrate is performed. The trapping and excitation values are optimized to reduce variation of mass assignment with ion population. The hexapole accumulation has the effect of integrating the ESI ions and thus improving the measurement of relative abundance data. Capillary exit voltage is typically 70 V.

Spectra from each time point are analyzed. A program entitled ExPro (Poster entitled "ExchangePro: An Automated High Performance Software Package for analysis of Deuterium Exchange Mass Spectrometric Data Obtained by FTMS", presented at the 52nd annual conference of the American Society for Mass Spectrometry) is used to calculate the "average mass" of the peptide's molecular ion cluster, by multiplying the mass times the intensity for each isotope of the cluster and dividing by the total intensity. The resulting data is plotted graphically for each peptide, yielding a map of protection for the protein. For all experiments, reported data is adjusted for the number of exchangeable hydrogens in each peptide; reported value=centroid/number of non-proline residues in the peptide minus one. ViewerLite 4.2 (Accelyrs Inc.) is employed to map results onto the crystal structures.

C. Results 51 peptic peptides [encompassing amino acids 7-20, 20-27, 20-28, 28-49, 50-56, 57-68, 81-87, 71-80, 91-95, 96-104, 96-105, 105-113, 109-115, 114-120, 114-121, 121-129, 130-135, 136-152, 140-151, 140-152, 165-171, 166-170, 172-187, 183-199, 188-198, 199-208, 218-223, 219-223, 235-238, 239-247, 248-269, 258-271, 270-274, 270-276, 270-280, 281-289, 293-301, 310-320, 313-320, 321-326, 326-330, 326-333, 327-332, 327-333, 331-335, 331-346, 347-362, 352-362, 363-374, 374-400, 378-386, 378-387] derived from the extracellular domain of NPRA are followed at each of 5 time points ranging from 5 to 1000 seconds. The differences in deuterium exchange rates upon ANP and ANP+antibody binding are determined and the peptides with the most significant, changes are mapped onto a homology model of ANP bound to the extracellular domain of human NPRA derived from the publicly available crystal structure of ligand bound rat NPRA (Ogawa, et al. (2004) *J. Biol. Chem.* 279:28625) The results from the binding of 5591 are depicted in FIG. 21.

The area shaded in pink (encompassing amino acids 28-87, 96-113, 293-301, 310-312, 334-335 and 352-362) represents strong protection from exchange and that shaded in red (encompassing amino acids 7-28, 121-129, 313-320, 327-333, 347-351) very strong protection. The areas shaded in red are represented by an epitope that comprises residues 7-28 (NLTVAVVLPLANTSYPWSWARV) (SEQ ID NO:30), 121-129 (VKDEYALTT) (SEQ ID NO:31), 313-320 (TMEDGLVN) (SEQ ID NO:32), 327-333 (HDGLLLY) (SEQ ID NO:33) and 347-351 (VTDGE) (SEQ ID NO:34) located in the three dimensional structure of NPRA when NPRA is bound to ANP and/or BNP and the areas shaded in pink represent epitopes that have peptide sequences

```
                                           (SEQ ID NO: 35)
28-87 (VGPAVELALAQVKARPDLLPGWTVRTVLGSSENALGVCSDTA
APLAAVDLKWEHNPAVFL), (SEQ ID NO: 36)
96-113 (APVGRFTAHWRVPLLTAG), (SEQ ID NO: 37)
293-301 (PEYLEFLKQ), (SEQ ID NO: 38)
310-312 (FNF), 334-335 (IQ), 352-362 (NITQRMWNRSF).
```

All of the changes are manifested as decreases in the rate of exchange. The size of the area of protection (mean 1680 A$^2$ for both partners) is in the same range as that reported for other antibody-antigen pairs. A bimodal distribution is observed in peptides protected from exchange by antibody binding. Binding to one side of the homodimer is a mechanism consistent with that observation. Interestingly the area shaded in red corresponds with that altered upon ANP binding to the receptor and is distant from the binding site of ANP which is in the interface between the homodimers.

The sequence of the NPRA-Fc fusion protein is:

```
                                           (SEQ ID NO: 45)
DGTSMGNLTVAVVLPLANTSYPWSWARVGPAVELALAQVKARPDLLPGW

TVRTVLGSSENALGVCSDTAAPLAAVDLKWEHNPAVFLGPGCVYAAAPV

GRFTAHWRVPLLTAGAPALGFGVKDEYALTTRAGPSYAKLGDFVAALHR

RLGWERQALMLYAYRPGDEEHCFFLVEGLFMRVRDRLNITVDHLEFAED

DLSHYTRLLRTMPRKGRVIYICSSPDAFRTLMLLALEAGLCGEDYVFFH

LDIFGQSLQGGQGPAPRRPWERGDGQDVSARQAFQAAKIITYKDPDNPE

YLEFLKQLKHLAYEQFNFTMEDGLVNTIPASFHDGLLLYIQAVTETLAH

GGTVTDGENITQRMWNRSFQGVTGYLKIDSSGDRETDFSLWDMDPENGA

FRVVLNYNGTSQELVAVSGRKLNWPLGYPPPDIPKCGFDNEDPACNQDH

LSTLEPIGGGSGGGPSVFLFPPKPKDTLMISRTPEVTCVVVDVSHEDPE

VKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQ

GNVFSCSVMHEALHNHYTQKSLSLSPVNDERPLESRGPV
```

Example 12

Species Cross-Reactivity

Initial species cross-reactivity studies are performed using HEK cell lines overexpressing rat, canine and rhesus monkey NPRA. The rat is a preferred model due to the availability and widespread use of heart failure models in this species, while the dog is examined due to the extensive profiling of recombinant BNP in this species. The rhesus monkey is also a preferred model based on the availability of sequence information on NPIRA and its high sequence homology to human. The affinities of 5591 to ANP-bound cellular NPRA of these various species are determined using the Kinexa technology. These apparent $K_d$ values are obtained by globally fitting the data for two antibody concentrations. The data shown below in Table 5 illustrate that 5591 binds to NPRA of different species with pM affinity. The antibody has the highest affinity against rat NPRA followed by dog, rhesus monkey and human.

TABLE 5

Affinity of 5591 to ANP bound NPRA expressed in HEK cells

| 5591 | $K_{d, app}$ (pM) ANP |
|---|---|
| Human NPRA | 590 |
| Rat NPRA | 13 |
| Canine NPRA | 96 |
| Rhesus NPRA | 266 |

The effects of 5502, 5591 and 5592 on cGMP production in response to species appropriate ANP and BNP are also assessed and the results are summarized in Table 6. As with human NPRA, the antibodies potentiate the cGMP production by dog and rhesus monkey NPRA in response to both ANP and BNP. With regard to rat NPRA, modest potentiation is observed with rat ANP but no shift in the dose response to rat BNP is seen in the presence of the antibodies. FACS experiments confirm that the antibodies binds to rat NPRA in the presence of BNP.

TABLE 6

Potentiation of Antibody mediated cGMP responses in ANP or BNP treated HEK NPRA cells

| IgG | Rat Fold shift in $EC_{50}$ | | Dog Fold shift in $EC_{50}$ | | Rhesus Monkey Fold shift in $EC_{50}$ | |
|---|---|---|---|---|---|---|
|  | ANP | BNP | ANP | BNP | ANP | BNP |
| 5502 | 2-3 | None | 3-5 | 7-10 | 2-8 | 12 |
| 5591 | 3 | None | 3-4 | 4-5 | 2-4 | 14 |
| 5592 | 5-6 | None | 1-4 | 7-10 | 2-6 | 16 |

Example 13

Pharmacokinetics Studies: ELISA for Detection of Antibody in Plasma

A sandwich ELISA is developed to determine the concentration of the antibodies in plasma. The capture antigen is ANP-bound NPRA-Fc fusion protein and the detection antibody is either a monoclonal anti-human IgG4 (for monkey plasma samples) or a monoclonal anti-human kappa chain (for rat and dog plasma samples) conjugated to horseradish peroxidase. Specifically, 96-well Nunc-Immuno MaxiSorp plates (Thermo Fisher Scientific, Rochester, N.Y.) are coated overnight with human NPRA-Fc containing 1 nM ANP. The plates are then blocked with 3% bovine serum albumin (BSA) in phosphate buffered saline (PBS) (BSA/PBS) for 1 hour at room temperature. The plates are then washed three times with PBS containing 0.1% Tween (PBST). For generating the standard curve, e.g., 5591 serially diluted 1:3, from 600 ng/ml to 0.09 ng/ml in 0.5% BSA/PBS with 1 nM ANP is added to the plate and incubated for 2 hours at room temperature. For the test samples, plasma is diluted at least 1:10 in PBS with 1 nM ANP. After the 2 hour incubation, plates are washed three times with PBST containing 0.5% BSA. To detect bound antibody, mouse anti-human IgG4-HRP or mouse anti-human kappa chain-HRP in 0.5% BSA/PBS is added and the plates are incubated at room temperature for 1 hour. After the 1 hour incubation, plates are washed three times with PBST containing 0.5% BSA, One final plate wash is done using PBS only. Color is developed by adding ABTS Single Solution for 10-20 min. Plates are read at 405 nm.

Example 14

Single Dose IV and SC Antibody Pharmacokinetics in Rat 5591 is dosed at 0.3 mg/kg IV and 2 mg/kg SC to male SD rats (N=3) in phosphate buffered saline vehicle. Blood samples are collected from 0-168 hr in K2-EDTA tubes and plasma samples were stored at −70° C. until analysis. The samples are analyzed by sandwich ELISA as described above. Pharmacokinetic parameters are summarized in Table 7. The antibody shows low clearance and volume of distribution (Vss) and a terminal half-life of 5.8 days. The antibody is rapidly and well absorbed after SC dose reaching a peak at about 3 days post dose and the SC bioavailability is 81%.

TABLE 7

Pharmacokinetic parameters of 5591 in male SD rats (N = 3) after single 0.3 mg/kg IV and 2 mg/kg SC doses.

| Route | Dose (mg/kg) | CLp (mL/hr/kg) | Vss (mL/kg) | AUC (µM · hr) | Cmax (nM) | Tmax (days) | T½ (days) | MRT (days) | F (%) |
|---|---|---|---|---|---|---|---|---|---|
| IV | 0.3 | 0.94 ± 0.16 | 165 ± 34 | 2.2 ± 0.3 | | | 5.8 ± 0.1 | 7.2 ± 0.3 | |
| SC | 2.0 | | | 11.6 ± 1.9 | 59.9 ± 0.2 | 3.0 ± 0.0 | | | 80.8 |

Example 15

Single Dose IV and SC Pharmacokinetics of Antibody in Dog

5591-IgG is dosed at 0.3 mg/kg IV to male beagle dogs (N=3) in 50 mM acetate/100 mM arginine/50 mM Tris and at the same dose SC in phosphate buffered saline vehicle, Blood samples are collected from 0-506 hr (3 weeks) in K2-EDTA tubes and plasma samples are stored at −70° C. until analysis. The samples are analyzed by sandwich ELISA as described above.

Pharmacokinetic parameters are summarized in Table 8. The antibody shows low clearance, low volume of distribution (Vss) approximating blood volume and a terminal half-life of 81 hours (~3 days).

TABLE 8

Pharmacokinetic parameters of 5591-IgG in male beagle dog (N = 3) after single 0.3 mg/kg IV and SC doses.

| Route | Dose (mg/kg) | CLp (mL/hr/kg) | Vss (mL/kg) | AUC (μg · hr) | Cmax (nM) | Tmax (days) | T½ (days) | MRT (days) | F (%) |
|---|---|---|---|---|---|---|---|---|---|
| IV | 0.3 | 0.81 ± 0.01 | 84 ± 15 | 2.5 ± 0.2 | | | 3.0 ± 0.6 | 4.4 ± 1.1 | |
| SC | 0.3 | | | 3.5 ± 0.7 | 9.2 ± 0.8 | 3.3 ± 1.2 | | | 139 |

Example 16

Single Dose IV and SC Pharmacokinetics of Antibodies in Monkey

5591-IgG is dosed at 0.3 mg/kg IV and SC to male cynomolgus monkies (N=3) in phosphate buffered saline vehicle. Blood samples are collected from 0-506 hr (3 weeks) in K2-EDTA tubes and plasma samples were stored at −70° C. until analysis. The samples are analyzed by sandwich ELISA as described above.

Pharmacokinetic parameters are summarized in Table 9. The antibody shows low clearance, low volume of distribution (Vss) slightly higher than the blood volume of 85-90 mL/kg and a terminal half-life of 203 hr (8.5 days). The antibody was slowly and well absorbed after SC dose reaching a peak at about 3 days post dose and the SC bioavailability was 145% and the reasons for greater than 100% bioavailability are currently not known.

TABLE 9

Pharmacokinetic parameters of BI 655,002 in male cynomolgus monkies (N = 3) after single 0.3 mg/kg IV and SC doses.

| Route | Dose (mg/kg) | CLp (mL/hr/kg) | Vss (mL/kg) | AUC (μM · hr) | Cmax (nM) | Tmax (days) | T½ (days) | MRT (days) | F (%) |
|---|---|---|---|---|---|---|---|---|---|
| IV | 0.3 | 0.54 ± 0.02 | 143 ± 12.0 | 3.7 ± 0.2 | | | 8.5 ± 0.6 | 10.9 ± 0.6 | |
| SC | 0.3 | | | 5.4 ± 0.5 | 17.5 ± 1.8 | 2.7 ± 0.6 | | | 145 |

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of pharmacokinetic analyses, recombinant DNA methods, peptide and protein chemistries, nucleic acid chemistry and molecular and cellular biology described herein are those well known and commonly used in the art.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein, including the appended embodiments.

What we claim is:

1. An isolated antibody or antigen-binding portion thereof that selectively binds to an epitope located in an extracellular domain of natriuretic peptide receptor A (NPRA) wherein said epitope forms when said NPRA is bound to atrial natriuretic peptide (ANP), or brain natriuretic peptide (BNP), wherein said antibody or antigen-binding portion thereof is not reactive with the atrial natriuretic peptide (ANP), or brain natriuretic peptide (BNP) binding site of NPRA, wherein said epitope is located in the three dimensional structure of NPRA when NPRA is bound to ANP or BNP, wherein said epitope comprises amino acids within NLTVAVVLPLANTSYP-WSWARV (SEQ ID NO:30), VKDEYALTT (SEQ ID NO:31), TMEDGLVN (SEQ ID NO:32), HDGLLLY (SEQ ID NO:33) and VTDGE (SEQ ID NO:34).

2. The antibody or antigen-binding portion thereof according to claim 1, wherein said antibody or portion thereof binds to the same epitope as an antibody comprising a VH and VL chain, each VH and VL chain comprising hypervariable regions CDR1, CDR2 and CDR3 separated by framework amino acid sequences, the hypervariable regions having amino acid sequences in each VH and VL, wherein VHCDR1 of said antibody has a sequence of SEQ ID NO:3;
VHCDR2 of said antibody has a sequence selected from the group consisting of SEQ ID NO:4 and 10,
VHCDR3 of said antibody has a sequence of SEQ ID NO:13,
VLCDR1 of said antibody has a sequence of SEQ ID NO:14,
VLCDR2 of said antibody has a sequence of SEQ ID NO:15; and
VLCDR3 of said antibody has a sequence selected from the group consisting of SEQ ID NO: 16, 17 and 18.

3. The antibody or antigen-binding portion thereof according to claim 2, wherein the antibody or portion thereof comprises a VH and VL chain, each VH and VL chain comprising hypervariable regions CDR1, CDR2 and CDR3 separated by framework amino acid sequences, the hypervariable regions having amino acid sequences selected from one of the following:

| | VHCDR1 | VHCDR2 | VHCDR3 |
|---|---|---|---|
| 5064: | VHCDR1 (SEQ ID NO: 3) | VHCDR2 (SEQ ID NO: 4) | VHCDR3 (SEQ ID NO: 13) |
| | VLCDR1 (SEQ ID NO: 14) | VLCDR2 (SEQ ID NO: 15) | VLCDR3 (SEQ ID NO: 16) |
| 5502: | VHCDR1 (SEQ ID NO: 3) | VHCDR2 (SEQ ID NO: 4) | VHCDR3 (SEQ ID NO: 13) |
| | VLCDR1 (SEQ ID NO: 14) | VLCDR2 (SEQ ID NO: 15) | VLCDR3 (SEQ ID NO: 17) |
| 5504: | VHCDR1 (SEQ ID NO: 3) | VHCDR2 (SEQ ID NO: 4) | VHCDR3 (SEQ ID NO: 13) |
| | VLCDR1 (SEQ ID NO: 14) | VLCDR2 (SEQ ID NO: 15) | VLCDR3 (SEQ ID NO: 18) |
| 5591: | VHCDR1 (SEQ ID NO: 3) | VHCDR2 (SEQ ID NO: 10) | VHCDR3 (SEQ ID NO: 13) |
| | VLCDR1 (SEQ ID NO: 14) | VLCDR2 (SEQ ID NO: 15) | VLCDR3 (SEQ ID NO: 17), and |
| 5592 | VHCDR1 (SEQ ID NO: 3) | VHCDR2 (SEQ ID NO: 10) | VHCDR3 (SEQ ID NO: 13) |
| | VLCDR1 (SEQ ID NO: 14) | VLCDR2 (SEQ ID NO: 15) | VLCDR3 (SEQ ID NO: 18). |

* * * * *

SEQUENCE LISTING

<160> NUMBER OF SEQ ID NOS: 45

<210> SEQ ID NO 1
<211> LENGTH: 4201
<212> TYPE: DNA
<213> ORGANISM: Artificial Sequence
<220> FEATURE:
<223> OTHER INFORMATION: DNA sequence for NPRA

<400> SEQUENCE: 1

| | | | | | | |
|---|---|---|---|---|---|---|
| acactccctg | gggcaggcgc | tcacgcacgc | tacaaacaca | cactcctctt | tcctccctcg | 60 |
| cgcgccctct | ctcatccttc | ttcacgaagc | gctcactcgc | accctttctc | tctctctctc | 120 |
| tctctctcta | acacgcacgc | acactcccag | ttgttcacac | tcgggtcctc | tccagcccga | 180 |
| cgttctcctg | gcacccacct | gctccgcggc | gccctgcgcg | cccccctcgg | tcgcgccccct | 240 |
| tgcgctctcg | gcccagaccg | tcgcagctac | aggggggcctc | gagccccggg | gtgagcgtcc | 300 |
| ccgtcccgct | cctgctcctt | cccatagggga | gcgcctgat | gcctgggacc | ggccgctgag | 360 |
| cccaaggggga | ccgaggaggc | catggtagga | gcgctcgcct | gctgcggtgc | ccgctgaggc | 420 |
| catgccgggg | ccccggcgcc | ccgctggctc | ccgcctgcgc | ctgctcctgc | tcctgctgct | 480 |
| gccgccgctg | ctgctgctgc | tccggggcag | ccacgcgggc | aacctgacgg | tagccgtggt | 540 |
| actgccgctg | gccaatacct | cgtaccccctg | gtcgtgggcg | cgcgtgggac | ccgccgtgga | 600 |
| gctggccctg | gcccaggtga | aggcgcgccc | cgacttgctg | ccgggctgga | cggtccgcac | 660 |
| ggtgctgggc | agcagcgaaa | acgcgctggg | cgtctgctcc | gacaccgcag | cgccccctggc | 720 |
| cgcggtggac | ctcaagtggg | agcacaaccc | cgctgtgttc | ctgggccccg | gctgcgtgta | 780 |
| cgccgccgcc | ccagtggggc | gcttcaccgc | gcactggcgg | gtcccgctgc | tgaccgccgg | 840 |
| cgccccggcg | ctgggcttcg | gtgtcaagga | cgagtatgcg | ctgaccaccc | gcgcggggcc | 900 |
| cagctacgcc | aagctggggg | acttcgtggc | ggcgctgcac | cgacggctgg | gctgggagcg | 960 |
| ccaagcgctc | atgctctacg | cctaccgcc | gggtgacgaa | gagcactgct | tcttcctcgt | 1020 |
| ggaggggctg | ttcatgcggg | tccgcgaccg | cctcaatatt | acggtggacc | acctggagtt | 1080 |
| cgccgaggac | gacctcagcc | actacaccag | gctgctgcgg | accatgccgc | gcaaaggccg | 1140 |
| agttatctac | atctgcagct | cccctgatgc | cttcagaacc | ctcatgctcc | tggccctgga | 1200 |
| agctggcttg | tgtggggagg | actacgtttt | cttccacctg | gatatctttg | ggcaaagcct | 1260 |
| gcaaggtgga | cagggccctg | ctccccgcag | gccctgggag | agagggggatg | gcaggatgt | 1320 |
| cagtgcccgc | caggcctttc | aggctgccaa | aatcattaca | tataaagacc | cagataatcc | 1380 |
| cgagtacttg | gaattcctga | agcagttaaa | cacctggcc | tatgagcagt | tcaacttcac | 1440 |
| catggaggat | ggcctggtga | acaccatccc | agcatccttc | cacgacgggc | tcctgctcta | 1500 |
| tatccaggca | gtgacggaga | ctctggcaca | tgggggaact | gttactgatg | gggagaacat | 1560 |
| cactcagcgg | atgtggaacc | gaagctttca | aggtgtgaca | ggatacctga | aaattgatag | 1620 |
| cagtggcgat | cgggaaacag | acttctccct | ctgggatatg | gatcccgaga | atggtgcctt | 1680 |
| cagggttgta | ctgaactaca | atgggacttc | ccaagagctg | gtggctgtgt | cggggcgcaa | 1740 |
| actgaactgg | ccctgggggt | acccctcctc | tgacatcccc | aaatgtggct | ttgacaacga | 1800 |
| agacccagca | tgcaaccaag | atcacctttc | caccctggag | gtgctggctt | tggtgggcag | 1860 |
| cctctctcttg | ctcggcattc | tgattgtctc | cttcttcata | tacaggaaga | tgcagctgga | 1920 |
| gaaggaactg | gcctcggagc | tgtggcgggt | gcgctgggag | gacgttgagc | ccagtagcct | 1980 |
| tgagaggcac | ctgcggagtg | caggcagccg | gctgaccctg | agcggagag | gctccaatta | 2040 |

```
cggctccctg ctaaccacag agggccagtt ccaagtcttt gccaagacag catattataa    2100
gggcaacctc gtggctgtga aacgtgtgaa ccgtaaacgc attgagctga cacgaaaagt    2160
cctgtttgaa ctgaagcata tgcgggatgt gcagaatgaa cacctgacca ggtttgtggg    2220
agcctgcacc gaccccccca atatctgcat cctcacagag tactgtcccc gtgggagcct    2280
gcaggacatt ctggagaatg agagcatcac cctggactgg atgttccggt actcactcac    2340
caatgacatc gtcaagggca tgctgtttct acacaatggg gctatctgtt ccatgggaa     2400
cctcaagtca tccaactgcg tggtagatgg gcgctttgtg ctcaagatca ccgactatgg    2460
gctggagagc ttcaggggcc tggacccaga gcaaggacac accgtttatg ccaaaaagct    2520
gtggacggcc cctgagctcc tgcgaatggc ttcacccct gtgcggggct cccaggctgg     2580
tgacgtatac agctttggga tcatccttca ggagattgcc ctgaggagtg ggtcttcca    2640
cgtggaaggt ttggacctga gccccaaaga gatcatcgag cgggtgactc ggggtgagca    2700
gccccccttc cggccctccc tggccctgca gagtcacctg gaggagttgg ggctgctcat    2760
gcagcggtgc tgggctgagg acccacagga gaggccacca ttccagcaga tccgcctgac    2820
gttgcgcaaa tttaacaggg agaacagcag caacatcctg acaacctgc tgtcccgcat     2880
ggagcagtac gcgaacaatc tggaggaact ggtggaggag cggacccagg catacctgga    2940
ggagaagcgc aaggctgagg ccctgctcta ccagatcctg cctcactcag tggctgagca    3000
gctgaagcgt ggggagacgg tgcaggccga agcctttgac agtgttacca tctacttcag    3060
tgacattgtg ggtttcacag cgctgtcggc ggagagcaca cccatgcagg tggtgacccct   3120
gctcaatgac ctgtacactt gctttgatgc tgtcatagac aactttgatg tgtacaaggt    3180
ggagacaatt ggcgatgcct acatggtggt gtcagggctc cctgtgcgga acggcggt     3240
acacgcctgc gaggtagccc gcatggccct ggcactgctg gatgctgtgc gctccttccg    3300
aatccgccac cggccccagg agcagctgcg cttgcgcatt ggcatccaca caggacctgt    3360
gtgtgctgga gtggtggac tgaagatgcc ccgttactgt ctctttgggg atacagtcaa     3420
cacagcctca agaatggagt ctaatgggga agccctgaag atccacttgt cttctgagac    3480
caaggctgtc ctggaggagt ttggtggttt cgagctggag cttcgagggg atgtagaaat    3540
gaagggcaaa ggcaaggttc ggacctactg gctccttggg gagagggga gtagcacccg    3600
aggctgacct gcctcctctc ctatccctcc acacctccct accctgtgcc agaagcaaca    3660
gaggtgccag gcctcagcct cacccacagc agcccatcg ccaaaggatg aagtaattt     3720
gaatagctca ggtgtgctga ccccagtgaa gacaccagat aggacctctg agaggggact    3780
ggcatggggg gatctcagag cttacaggct gagccaagcc cacggccatg cacagggaca    3840
ctcacacagg cacacgcacc tgctctccac ctggactcag gccgggctgg gctgtggatt    3900
cctgatcccc tcccctcccc atgctctcct ccctcagcct tgctaccctg tgacttactg    3960
ggaggagaaa gagtcacctg aaggggaaca tgaaaagaga ctaggtgaag agagggcagg    4020
ggagcccaca tctgggctg gcccacaata cctgctcccc cgaccccctc cacccagcag    4080
tagacacagt gcacagggga gaagaggggt ggcgcagaag ggttgggggc ctgtatgcct    4140
tgcttctacc atgagcagag acaattaaaa tctttattcc agtgaaaaaa aaaaaaaaaa    4200
a                                                                     4201
```

<210> SEQ ID NO 2
<211> LENGTH: 1061
<212> TYPE: PRT

<213> ORGANISM: Artificial Sequence
<220> FEATURE:
<223> OTHER INFORMATION: Amino acid sequence for NPRA

<400> SEQUENCE: 2

```
Met Pro Gly Pro Arg Pro Ala Gly Ser Arg Leu Arg Leu Leu Leu
1               5                   10                  15

Leu Leu Leu Leu Pro Pro Leu Leu Leu Leu Arg Gly Ser His Ala
            20                  25                  30

Gly Asn Leu Thr Val Ala Val Val Leu Pro Leu Ala Asn Thr Ser Tyr
        35                  40                  45

Pro Trp Ser Trp Ala Arg Val Gly Pro Ala Val Glu Leu Ala Leu
    50                  55                  60

Gln Val Lys Ala Arg Pro Asp Leu Leu Pro Gly Trp Thr Val Arg Thr
65                  70                  75                  80

Val Leu Gly Ser Ser Glu Asn Ala Leu Gly Val Cys Ser Asp Thr Ala
                85                  90                  95

Ala Pro Leu Ala Ala Val Asp Leu Lys Trp Glu His Asn Pro Ala Val
            100                 105                 110

Phe Leu Gly Pro Gly Cys Val Tyr Ala Ala Pro Val Gly Arg Phe
    115                 120                 125

Thr Ala His Trp Arg Val Pro Leu Leu Thr Ala Gly Ala Pro Ala Leu
    130                 135                 140

Gly Phe Gly Val Lys Asp Glu Tyr Ala Leu Thr Thr Arg Ala Gly Pro
145                 150                 155                 160

Ser Tyr Ala Lys Leu Gly Asp Phe Val Ala Ala Leu His Arg Arg Leu
                165                 170                 175

Gly Trp Glu Arg Gln Ala Leu Met Leu Tyr Ala Tyr Arg Pro Gly Asp
            180                 185                 190

Glu Glu His Cys Phe Phe Leu Val Glu Gly Leu Phe Met Arg Val Arg
        195                 200                 205

Asp Arg Leu Asn Ile Thr Val Asp His Leu Glu Phe Ala Glu Asp Asp
    210                 215                 220

Leu Ser His Tyr Thr Arg Leu Leu Arg Thr Met Pro Arg Lys Gly Arg
225                 230                 235                 240

Val Ile Tyr Ile Cys Ser Ser Pro Asp Ala Phe Arg Thr Leu Met Leu
                245                 250                 255

Leu Ala Leu Glu Ala Gly Leu Cys Gly Glu Asp Tyr Val Phe Phe His
            260                 265                 270

Leu Asp Ile Phe Gly Gln Ser Leu Gln Gly Gly Gln Gly Pro Ala Pro
        275                 280                 285

Arg Arg Pro Trp Glu Arg Gly Asp Gly Gln Asp Val Ser Ala Arg Gln
    290                 295                 300

Ala Phe Gln Ala Ala Lys Ile Ile Thr Tyr Lys Asp Pro Asp Asn Pro
305                 310                 315                 320

Glu Tyr Leu Glu Phe Leu Lys Gln Leu Lys His Leu Ala Tyr Glu Gln
                325                 330                 335

Phe Asn Phe Thr Met Glu Asp Gly Leu Val Asn Thr Ile Pro Ala Ser
            340                 345                 350

Phe His Asp Gly Leu Leu Leu Tyr Ile Gln Ala Val Thr Glu Thr Leu
        355                 360                 365

Ala His Gly Gly Thr Val Thr Asp Gly Glu Asn Ile Thr Gln Arg Met
    370                 375                 380

Trp Asn Arg Ser Phe Gln Gly Val Thr Gly Tyr Leu Lys Ile Asp Ser
```

-continued

```
385             390             395             400
Ser Gly Asp Arg Glu Thr Asp Phe Ser Leu Trp Asp Met Asp Pro Glu
                    405             410             415

Asn Gly Ala Phe Arg Val Val Leu Asn Tyr Asn Gly Thr Ser Gln Glu
                420             425             430

Leu Val Ala Val Ser Gly Arg Lys Leu Asn Trp Pro Leu Gly Tyr Pro
                435             440             445

Pro Pro Asp Ile Pro Lys Cys Gly Phe Asp Asn Glu Asp Pro Ala Cys
            450             455             460

Asn Gln Asp His Leu Ser Thr Leu Glu Val Leu Ala Leu Val Gly Ser
465             470             475             480

Leu Ser Leu Leu Gly Ile Leu Ile Val Ser Phe Phe Ile Tyr Arg Lys
                    485             490             495

Met Gln Leu Glu Lys Glu Leu Ala Ser Glu Leu Trp Arg Val Arg Trp
                500             505             510

Glu Asp Val Glu Pro Ser Ser Leu Glu Arg His Leu Arg Ser Ala Gly
                515             520             525

Ser Arg Leu Thr Leu Ser Gly Arg Gly Ser Asn Tyr Gly Ser Leu Leu
            530             535             540

Thr Thr Glu Gly Gln Phe Gln Val Phe Ala Lys Thr Ala Tyr Tyr Lys
545             550             555             560

Gly Asn Leu Val Ala Val Lys Arg Val Asn Arg Lys Arg Ile Glu Leu
                565             570             575

Thr Arg Lys Val Leu Phe Glu Leu Lys His Met Arg Asp Val Gln Asn
                580             585             590

Glu His Leu Thr Arg Phe Val Gly Ala Cys Thr Asp Pro Pro Asn Ile
            595             600             605

Cys Ile Leu Thr Glu Tyr Cys Pro Arg Gly Ser Leu Gln Asp Ile Leu
            610             615             620

Glu Asn Glu Ser Ile Thr Leu Asp Trp Met Phe Arg Tyr Ser Leu Thr
625             630             635             640

Asn Asp Ile Val Lys Gly Met Leu Phe Leu His Asn Gly Ala Ile Cys
                645             650             655

Ser His Gly Asn Leu Lys Ser Ser Asn Cys Val Val Asp Gly Arg Phe
                660             665             670

Val Leu Lys Ile Thr Asp Tyr Gly Leu Glu Ser Phe Arg Asp Leu Asp
            675             680             685

Pro Glu Gln Gly His Thr Val Tyr Ala Lys Lys Leu Trp Thr Ala Pro
        690             695             700

Glu Leu Leu Arg Met Ala Ser Pro Pro Val Arg Gly Ser Gln Ala Gly
705             710             715             720

Asp Val Tyr Ser Phe Gly Ile Ile Leu Gln Glu Ile Ala Leu Arg Ser
                    725             730             735

Gly Val Phe His Val Glu Gly Leu Asp Leu Ser Pro Lys Glu Ile Ile
                740             745             750

Glu Arg Val Thr Arg Gly Glu Gln Pro Pro Phe Arg Pro Ser Leu Ala
            755             760             765

Leu Gln Ser His Leu Glu Glu Leu Gly Leu Leu Met Gln Arg Cys Trp
        770             775             780

Ala Glu Asp Pro Gln Glu Arg Pro Pro Phe Gln Gln Ile Arg Leu Thr
785             790             795             800

Leu Arg Lys Phe Asn Arg Glu Asn Ser Ser Asn Ile Leu Asp Asn Leu
                    805             810             815
```

```
Leu Ser Arg Met Glu Gln Tyr Ala Asn Asn Leu Glu Glu Leu Val Glu
            820                 825                 830

Glu Arg Thr Gln Ala Tyr Leu Glu Lys Arg Lys Ala Glu Ala Leu
        835                 840                 845

Leu Tyr Gln Ile Leu Pro His Ser Val Ala Gln Leu Lys Arg Gly
    850                 855                 860

Glu Thr Val Gln Ala Glu Ala Phe Asp Ser Val Thr Ile Tyr Phe Ser
865                 870                 875                 880

Asp Ile Val Gly Phe Thr Ala Leu Ser Ala Glu Ser Thr Pro Met Gln
                885                 890                 895

Val Val Thr Leu Leu Asn Asp Leu Tyr Thr Cys Phe Asp Ala Val Ile
                900                 905                 910

Asp Asn Phe Asp Val Tyr Lys Val Glu Thr Ile Gly Asp Ala Tyr Met
            915                 920                 925

Val Val Ser Gly Leu Pro Val Arg Asn Gly Arg Leu His Ala Cys Glu
    930                 935                 940

Val Ala Arg Met Ala Leu Ala Leu Leu Asp Ala Val Arg Ser Phe Arg
945                 950                 955                 960

Ile Arg His Arg Pro Gln Glu Gln Leu Arg Leu Arg Ile Gly Ile His
                965                 970                 975

Thr Gly Pro Val Cys Ala Gly Val Val Gly Leu Lys Met Pro Arg Tyr
                980                 985                 990

Cys Leu Phe Gly Asp Thr Val Asn Thr Ala Ser Arg Met Glu Ser Asn
            995                 1000                1005

Gly Glu Ala Leu Lys Ile His Leu Ser Ser Glu Thr Lys Ala Val
    1010                1015                1020

Leu Glu Glu Phe Gly Gly Phe Glu Leu Glu Leu Arg Gly Asp Val
    1025                1030                1035

Glu Met Lys Gly Lys Gly Lys Val Arg Thr Tyr Trp Leu Leu Gly
    1040                1045                1050

Glu Arg Gly Ser Ser Thr Arg Gly
    1055                1060

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

Gly Asp Ser Val Ser Ser Arg Ser Ala Ser Trp Ser
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Synthetic

<400> SEQUENCE: 4

Arg Ile Tyr Tyr Arg Ser Lys Trp Tyr Asn Asp Tyr Ala Val Ser Val
1               5                   10                  15

Lys Ser

<210> SEQ ID NO 5
```

```
<211> LENGTH: 18
<212> TYPE: PRT
<213> ORGANISM: Artificial Sequence
<220> FEATURE:
<223> OTHER INFORMATION: Synthetic

<400> SEQUENCE: 5

Arg Thr Tyr Tyr Arg Ser His Trp Tyr Phe Glu Tyr Ala Gly Ser Val
1               5                   10                  15

Lys Ser

<210> SEQ ID NO 6
<211> LENGTH: 18
<212> TYPE: PRT
<213> ORGANISM: Artificial Sequence
<220> FEATURE:
<223> OTHER INFORMATION: Synthetic

<400> SEQUENCE: 6

Arg Thr Tyr Tyr Arg Ser His Trp Tyr Trp Glu Tyr Ala Asp Ser Val
1               5                   10                  15

Lys Ser

<210> SEQ ID NO 7
<211> LENGTH: 18
<212> TYPE: PRT
<213> ORGANISM: Artificial Sequence
<220> FEATURE:
<223> OTHER INFORMATION: Synthetic

<400> SEQUENCE: 7

Arg Thr Tyr Tyr Arg Ser His Trp Tyr Tyr Glu Tyr Ala Arg Ser Val
1               5                   10                  15

Lys Ser

<210> SEQ ID NO 8
<211> LENGTH: 18
<212> TYPE: PRT
<213> ORGANISM: Artificial Sequence
<220> FEATURE:
<223> OTHER INFORMATION: Synthetic

<400> SEQUENCE: 8

Arg Thr Tyr Tyr Arg Ser His Trp Tyr Phe Glu Tyr Ala His Ser Val
1               5                   10                  15

Lys Ser

<210> SEQ ID NO 9
<211> LENGTH: 18
<212> TYPE: PRT
<213> ORGANISM: Artificial Sequence
<220> FEATURE:
<223> OTHER INFORMATION: Synthetic

<400> SEQUENCE: 9

Arg Thr Tyr Tyr Arg Ser His Trp Tyr Tyr Glu Tyr Ala Ala Ser Val
1               5                   10                  15

Lys Ser

<210> SEQ ID NO 10
<211> LENGTH: 18
<212> TYPE: PRT
<213> ORGANISM: Artificial Sequence
<220> FEATURE:
```

<223> OTHER INFORMATION: Synthetic

<400> SEQUENCE: 10

Arg Thr Tyr Tyr Arg Ser His Trp Tyr Tyr Glu Tyr Ala Gln Ser Val
1               5                   10                  15

Lys Ser

<210> SEQ ID NO 11
<211> LENGTH: 18
<212> TYPE: PRT
<213> ORGANISM: Artificial Sequence
<220> FEATURE:
<223> OTHER INFORMATION: Synthetic

<400> SEQUENCE: 11

Arg Thr Tyr Tyr Arg Ser His Trp Tyr Met Glu Tyr Ala His Ser Val
1               5                   10                  15

Lys Ser

<210> SEQ ID NO 12
<211> LENGTH: 18
<212> TYPE: PRT
<213> ORGANISM: Artificial Sequence
<220> FEATURE:
<223> OTHER INFORMATION: Synthetic

<400> SEQUENCE: 12

Arg Thr Tyr Tyr Arg Ser Lys Trp Tyr Glu Tyr Ala His Ser Val
1               5                   10                  15

Lys Ser

<210> SEQ ID NO 13
<211> LENGTH: 18
<212> TYPE: PRT
<213> ORGANISM: Artificial Sequence
<220> FEATURE:
<223> OTHER INFORMATION: Synthetic

<400> SEQUENCE: 13

Arg Ile Tyr Tyr Arg Ser Lys Trp Tyr Asn Asp Tyr Ala Val Ser Val
1               5                   10                  15

Lys Ser

<210> SEQ ID NO 14
<211> LENGTH: 12
<212> TYPE: PRT
<213> ORGANISM: Artificial Sequence
<220> FEATURE:
<223> OTHER INFORMATION: Synthetic

<400> SEQUENCE: 14

Arg Ala Ser Gln Ser Val Arg Ser Asn Tyr Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Gly Ala Ser Asn Arg Ala Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Ile Ser Asn Pro Pro Val Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Gln Gln Ile Ser Asn Ser Pro Pro Thr
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Gln Gln Ile Ser Arg Ala Pro Ala Thr
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Gln Gln Ile Ser Thr Asn Pro Pro Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic

<400> SEQUENCE: 20

Gln Gln Ile Ser Ser Ser Pro Ala Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Gln Gln Ile Ser Ile Ser Pro Pro Thr
1               5

<210> SEQ ID NO 22
<211> LENGTH: 25
<212> TYPE: PRT
<213> ORGANISM: Artificial Sequence
<220> FEATURE:
<223> OTHER INFORMATION: Synthetic

<400> SEQUENCE: 22

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 23
<211> LENGTH: 14
<212> TYPE: PRT
<213> ORGANISM: Artificial Sequence
<220> FEATURE:
<223> OTHER INFORMATION: Synthetic

<400> SEQUENCE: 23

Trp Ile Arg Gln Ser Pro Gly Arg Gly Leu Glu Trp Leu Gly
1               5                   10

<210> SEQ ID NO 24
<211> LENGTH: 32
<212> TYPE: PRT
<213> ORGANISM: Artificial Sequence
<220> FEATURE:
<223> OTHER INFORMATION: Synthetic

<400> SEQUENCE: 24

Arg Ile Thr Ile Asn Pro Asp Thr Ser Lys Asn Gln Phe Ser Leu Gln
1               5                   10                  15

Leu Asn Ser Val Thr Pro Glu Asp Thr Ala Val Tyr Tyr Cys Ala Arg
            20                  25                  30

<210> SEQ ID NO 25
<211> LENGTH: 11
<212> TYPE: PRT
<213> ORGANISM: Artificial Sequence
<220> FEATURE:
<223> OTHER INFORMATION: Synthetic

<400> SEQUENCE: 25

Trp Gly Gln Gly Thr Leu Val Thr Val Ser Ser
1               5                   10

<210> SEQ ID NO 26
<211> LENGTH: 23
<212> TYPE: PRT
<213> ORGANISM: Artificial Sequence
<220> FEATURE:
<223> OTHER INFORMATION: Synthetic

<400> SEQUENCE: 26

Asp Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 27
<211> LENGTH: 15
<212> TYPE: PRT
<213> ORGANISM: Artificial Sequence

```
<220> FEATURE:
<223> OTHER INFORMATION: Synthetic

<400> SEQUENCE: 27

Trp Tyr Gln Gln Lys Pro Gly Gln Ala Pro Arg Leu Leu Ile Tyr
1               5                   10                  15

<210> SEQ ID NO 28
<211> LENGTH: 32
<212> TYPE: PRT
<213> ORGANISM: Artificial Sequence
<220> FEATURE:
<223> OTHER INFORMATION: Synthetic

<400> SEQUENCE: 28

Gly Val Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 29
<211> LENGTH: 12
<212> TYPE: PRT
<213> ORGANISM: Artificial Sequence
<220> FEATURE:
<223> OTHER INFORMATION: Synthetic

<400> SEQUENCE: 29

Phe Gly Gln Gly Thr Lys Val Glu Ile Lys Arg Thr
1               5                   10

<210> SEQ ID NO 30
<211> LENGTH: 22
<212> TYPE: PRT
<213> ORGANISM: Artificial Sequence
<220> FEATURE:
<223> OTHER INFORMATION: Synthetic

<400> SEQUENCE: 30

Asn Leu Thr Val Ala Val Val Leu Pro Leu Ala Asn Thr Ser Tyr Pro
1               5                   10                  15

Trp Ser Trp Ala Arg Val
            20

<210> SEQ ID NO 31
<211> LENGTH: 9
<212> TYPE: PRT
<213> ORGANISM: Artificial Sequence
<220> FEATURE:
<223> OTHER INFORMATION: Synthetic

<400> SEQUENCE: 31

Val Lys Asp Glu Tyr Ala Leu Thr Thr
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

Thr Met Glu Asp Gly Leu Val Asn
1               5
```

<210> SEQ ID NO 33
<211> LENGTH: 7
<212> TYPE: PRT
<213> ORGANISM: Artificial Sequence
<220> FEATURE:
<223> OTHER INFORMATION: Synthetic

<400> SEQUENCE: 33

His Asp Gly Leu Leu Leu Tyr
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic

<400> SEQUENCE: 34

Val Thr Asp Gly Glu
1               5

<210> SEQ ID NO 35
<211> LENGTH: 60
<212> TYPE: PRT
<213> ORGANISM: Artificial Sequence
<220> FEATURE:
<223> OTHER INFORMATION: Synthetic

<400> SEQUENCE: 35

Val Gly Pro Ala Val Glu Leu Ala Leu Ala Gln Val Lys Ala Arg Pro
1               5                   10                  15

Asp Leu Leu Pro Gly Trp Thr Val Arg Thr Val Leu Gly Ser Ser Glu
            20                  25                  30

Asn Ala Leu Gly Val Cys Ser Asp Thr Ala Ala Pro Leu Ala Ala Val
        35                  40                  45

Asp Leu Lys Trp Glu His Asn Pro Ala Val Phe Leu
    50                  55                  60

<210> SEQ ID NO 36
<211> LENGTH: 18
<212> TYPE: PRT
<213> ORGANISM: Artificial Sequence
<220> FEATURE:
<223> OTHER INFORMATION: Synthetic

<400> SEQUENCE: 36

Ala Pro Val Gly Arg Phe Thr Ala His Trp Arg Val Pro Leu Leu Thr
1               5                   10                  15

Ala Gly

<210> SEQ ID NO 37
<211> LENGTH: 9
<212> TYPE: PRT
<213> ORGANISM: Artificial Sequence
<220> FEATURE:
<223> OTHER INFORMATION: Synthetic

<400> SEQUENCE: 37

Pro Glu Tyr Leu Glu Phe Leu Lys Gln
1               5

<210> SEQ ID NO 38
<211> LENGTH: 11

```
<212> TYPE: PRT
<213> ORGANISM: Artificial Sequence
<220> FEATURE:
<223> OTHER INFORMATION: Synthetic

<400> SEQUENCE: 38

Asn Ile Thr Gln Arg Met Trp Asn Arg Ser Phe
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic

<400> SEQUENCE: 39

Gly Asp Ser Val Ser Ser Asn Ser Ala Ala Trp Ser
1               5                   10

<210> SEQ ID NO 40
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa can be any naturally occurring amino acid
      or no amino acid at all

<400> SEQUENCE: 40

Arg Thr Tyr Tyr Arg Xaa Ser His Trp Tyr Phe Glu Tyr Ala Val Ser
1               5                   10                  15

Val Lys Ser

<210> SEQ ID NO 41
<211> LENGTH: 11
<212> TYPE: PRT
<213> ORGANISM: Artificial Sequence
<220> FEATURE:
<223> OTHER INFORMATION: Synthetic

<400> SEQUENCE: 41

Met Asp Val Pro Ser Phe Arg Tyr Phe Asp Val
1               5                   10

<210> SEQ ID NO 42
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(12)
<223> OTHER INFORMATION: Xaa can be any naturally occurring amino acid
      or no amino acid at all

<400> SEQUENCE: 42

Arg Ala Ser Gln Ser Val Arg Ser Xaa Xaa Xaa Xaa Asn Tyr Leu Ala
1               5                   10                  15

<210> SEQ ID NO 43
<211> LENGTH: 7
<212> TYPE: PRT
<213> ORGANISM: Artificial Sequence
```

```
<220> FEATURE:
<223> OTHER INFORMATION: Synthetic

<400> SEQUENCE: 43

Gly Ala Ser Asn Arg Ala Thr
1               5

<210> SEQ ID NO 44
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(9)
<223> OTHER INFORMATION: Xaa can be any naturally occurring amino acid
      or no amino acid at all

<400> SEQUENCE: 44

Gln Gln Ile Ser Asn Pro Pro Xaa Xaa Val
1               5                   10

<210> SEQ ID NO 45
<211> LENGTH: 676
<212> TYPE: PRT
<213> ORGANISM: Artificial Sequence
<220> FEATURE:
<223> OTHER INFORMATION: Synthetic

<400> SEQUENCE: 45
```

Asp Gly Thr Ser Met Gly Asn Leu Thr Val Ala Val Val Leu Pro Leu
1               5                   10                  15

Ala Asn Thr Ser Tyr Pro Trp Ser Trp Ala Arg Val Gly Pro Ala Val
            20                  25                  30

Glu Leu Ala Leu Ala Gln Val Lys Ala Arg Pro Asp Leu Leu Pro Gly
        35                  40                  45

Trp Thr Val Arg Thr Val Leu Gly Ser Ser Glu Asn Ala Leu Gly Val
    50                  55                  60

Cys Ser Asp Thr Ala Ala Pro Leu Ala Ala Val Asp Leu Lys Trp Glu
65                  70                  75                  80

His Asn Pro Ala Val Phe Leu Gly Pro Gly Cys Val Tyr Ala Ala Ala
                85                  90                  95

Pro Val Gly Arg Phe Thr Ala His Trp Arg Val Pro Leu Leu Thr Ala
            100                 105                 110

Gly Ala Pro Ala Leu Gly Phe Gly Val Lys Asp Glu Tyr Ala Leu Thr
        115                 120                 125

Thr Arg Ala Gly Pro Ser Tyr Ala Lys Leu Gly Asp Phe Val Ala Ala
    130                 135                 140

Leu His Arg Arg Leu Gly Trp Glu Arg Gln Ala Leu Met Leu Tyr Ala
145                 150                 155                 160

Tyr Arg Pro Gly Asp Glu Glu His Cys Phe Phe Leu Val Glu Gly Leu
                165                 170                 175

Phe Met Arg Val Arg Asp Arg Leu Asn Ile Thr Val Asp His Leu Glu
            180                 185                 190

Phe Ala Glu Asp Asp Leu Ser His Tyr Thr Arg Leu Leu Arg Thr Met
        195                 200                 205

Pro Arg Lys Gly Arg Val Ile Tyr Ile Cys Ser Ser Pro Asp Ala Phe
    210                 215                 220

Arg Thr Leu Met Leu Leu Ala Leu Glu Ala Gly Leu Cys Gly Glu Asp

```
            225                 230                 235                 240
Tyr Val Phe Phe His Leu Asp Ile Phe Gly Gln Ser Leu Gln Gly Gly
                    245                 250                 255

Gln Gly Pro Ala Pro Arg Arg Pro Trp Glu Arg Gly Asp Gly Gln Asp
            260                 265                 270

Val Ser Ala Arg Gln Ala Phe Gln Ala Ala Lys Ile Thr Tyr Lys
            275                 280                 285

Asp Pro Asp Asn Pro Glu Tyr Leu Glu Phe Leu Lys Gln Leu Lys His
            290                 295                 300

Leu Ala Tyr Glu Gln Phe Asn Phe Thr Met Glu Asp Gly Leu Val Asn
305                 310                 315                 320

Thr Ile Pro Ala Ser Phe His Asp Gly Leu Leu Tyr Ile Gln Ala
                    325                 330                 335

Val Thr Glu Thr Leu Ala His Gly Gly Thr Val Thr Gly Glu Asn
            340                 345                 350

Ile Thr Gln Arg Met Trp Asn Arg Ser Phe Gln Gly Val Thr Gly Tyr
            355                 360                 365

Leu Lys Ile Asp Ser Ser Gly Asp Arg Glu Thr Asp Phe Ser Leu Trp
370                 375                 380

Asp Met Asp Pro Glu Asn Gly Ala Phe Arg Val Val Leu Asn Tyr Asn
385                 390                 395                 400

Gly Thr Ser Gln Glu Leu Val Ala Val Ser Gly Arg Lys Leu Asn Trp
            405                 410                 415

Pro Leu Gly Tyr Pro Pro Asp Ile Pro Lys Cys Gly Phe Asp Asn
            420                 425                 430

Glu Asp Pro Ala Cys Asn Gln Asp His Leu Ser Thr Leu Glu Pro Ile
            435                 440                 445

Gly Gly Gly Ser Gly Gly Gly Pro Ser Val Phe Leu Phe Pro Pro Lys
            450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                    485                 490                 495

Val Asp Gly Val Glu Val His Asn Ala Lys Thr Lys Pro Arg Glu Glu
            500                 505                 510

Gln Tyr Asn Ser Thr Tyr Arg Val Val Ser Val Leu Thr Val Leu His
            515                 520                 525

Gln Asp Trp Leu Asn Gly Lys Glu Tyr Lys Cys Lys Val Ser Asn Lys
            530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Asp Glu Leu
            565                 570                 575

Thr Lys Asn Gln Val Ser Leu Thr Cys Leu Val Lys Gly Phe Tyr Pro
            580                 585                 590

Ser Asp Ile Ala Val Glu Trp Glu Ser Asn Gly Gln Pro Glu Asn Asn
            595                 600                 605

Tyr Lys Thr Thr Pro Pro Val Leu Asp Ser Asp Gly Ser Phe Phe Leu
            610                 615                 620

Tyr Ser Lys Leu Thr Val Asp Lys Ser Arg Trp Gln Gln Gly Asn Val
625                 630                 635                 640

Phe Ser Cys Ser Val Met His Glu Ala Leu His Asn His Tyr Thr Gln
                    645                 650                 655
```

```
Lys Ser Leu Ser Leu Ser Pro Val Asn Asp Glu Arg Pro Leu Glu Ser
            660                 665                 670

Arg Gly Pro Val
        675
```